(12) United States Patent
Walker et al.

(10) Patent No.: US 9,726,647 B2
(45) Date of Patent: Aug. 8, 2017

(54) DETERMINING MECHANICAL PROPERTIES VIA ULTRASOUND-INDUCED RESONANCE

(71) Applicant: HEMOSONICS, LLC, Charlottesville, VA (US)

(72) Inventors: William F. Walker, Charlottesville, VA (US); F. Scott Corey, Jr., Baltimore, MD (US); Andrew Homyk, Charlottesville, VA (US); Tim Higgins, Charlottesville, VA (US); Francesco Viola, Charlottesville, VA (US); Frank Regan, Baltimore, MD (US); Elisa Ferrante, Charlottesville, VA (US)

(73) Assignee: Hemosonics, LLC, Charlottesville, VA (US)

( * ) Notice: Subject to any disclaimer, the term of this patent is extended or adjusted under 35 U.S.C. 154(b) by 159 days.

(21) Appl. No.: 14/660,700

(22) Filed: Mar. 17, 2015

(65) Prior Publication Data

US 2016/0274067 A1    Sep. 22, 2016

(51) Int. Cl.
G01N 29/44    (2006.01)
G01N 29/036    (2006.01)

(52) U.S. Cl.
CPC ....... *G01N 29/4418* (2013.01); *G01N 29/036* (2013.01); *G01N 29/4436* (2013.01);
(Continued)

(58) Field of Classification Search
CPC ........... G01N 29/4418; G01N 29/4436; G01N 29/4472; G01N 29/036; G01N 2291/014;
(Continued)

(56) References Cited

U.S. PATENT DOCUMENTS 3,537,541 A * 11/1970 Moore ................ G01N 29/07
                                                  367/180
3,720,098 A *  3/1973 Dixon ................ G01N 29/07
                                                   73/597
(Continued)

FOREIGN PATENT DOCUMENTS

AU    2011/237383     10/2011
CN    101035479        9/2007
(Continued)

OTHER PUBLICATIONS

Amukele, T.K. et al., "Comparison of Plasma With Whole Blood Prothrombin Time and Fibrinogen on the Same Instrument," American Journal of Clinical Pathology, vol. 133, No. 4, 2010, pp. 550-556.
(Continued)

*Primary Examiner* — J M Saint Surin
(74) *Attorney, Agent, or Firm* — Meunier Carlin & Curfman LLC

(57) ABSTRACT

A device for estimating a mechanical property of a sample is disclosed herein. The device may include a chamber configured to hold the sample; a transmitter configured to transmit a plurality of waveforms, including at least one forcing waveform; and a transducer assembly operatively connected to the transmitter and configured to transform the transmit waveforms into ultrasound waveforms. The transducer assembly can also transmit and receive ultrasound waveforms into and out of the chamber, as well as transform at least two received ultrasound waveforms into received electrical waveforms. The device also includes a data processor that can receive the received electrical waveforms; estimate a difference in the received electrical waveforms that results at least partially from movement of the sample; and estimate a mechanical property of the sample by comparing at least one feature of the estimated difference to at
(Continued)

least one predicted feature, wherein the at least one predicted feature is based on a model of an effect of the chamber wall. Finally, the device can also include a controller configured to control the timing of the ultrasound transmitter and data processor.

30 Claims, 16 Drawing Sheets

(52) U.S. Cl.
CPC ... *G01N 29/4472* (2013.01); *G01N 2291/014* (2013.01); *G01N 2291/02466* (2013.01); *G01N 2291/02818* (2013.01); *G01N 2291/02827* (2013.01)

(58) Field of Classification Search
CPC .......... G01N 2291/02466; G01N 2291/02827; G01N 2291/02818
USPC ......................................................... 73/571
See application file for complete search history.

(56) References Cited

U.S. PATENT DOCUMENTS

| | | | |
|---|---|---|---|
| 3,996,791 A | 12/1976 | Niklas et al. | |
| 3,996,792 A | 12/1976 | Kubota et al. | |
| 4,105,018 A | 8/1978 | Greenleaf et al. | |
| 4,112,740 A | 9/1978 | Brandestini | |
| 4,123,731 A | 10/1978 | Kanbara et al. | |
| 4,238,725 A | 12/1980 | Karplus et al. | |
| 4,248,092 A | 2/1981 | Vasile et al. | |
| 4,292,848 A | 10/1981 | Rainey et al. | |
| 4,293,934 A | 10/1981 | Herolz et al. | |
| 4,305,294 A | 12/1981 | Vasile et al. | |
| 4,406,167 A | 9/1983 | Maeda | |
| 4,435,984 A | 3/1984 | Gruber | |
| 4,484,569 A * | 11/1984 | Driller .................. A61B 8/10 600/439 | |
| 4,522,064 A | 6/1985 | McMillan | |
| 4,558,589 A | 12/1985 | Hemmes et al. | |
| 4,559,827 A | 12/1985 | Kupperman et al. | |
| 4,570,487 A | 2/1986 | Gruber | |
| 4,598,973 A | 7/1986 | Greenleaf | |
| 4,641,531 A | 2/1987 | Reeves et al. | |
| 4,658,649 A | 4/1987 | Brook | |
| 4,658,827 A | 4/1987 | He et al. | |
| 4,679,437 A | 7/1987 | Koike et al. | |
| 4,695,956 A | 9/1987 | Leveen et al. | |
| 4,702,110 A | 10/1987 | Holt | |
| 4,705,756 A | 11/1987 | Spillert et al. | |
| 4,735,096 A | 4/1988 | Dorr | |
| 4,806,070 A | 2/1989 | Poux et al. | |
| 4,814,247 A | 3/1989 | Spillert et al. | |
| 4,829,430 A | 5/1989 | Greenleaf et al. | |
| 4,852,577 A | 8/1989 | Smith et al. | |
| 4,891,587 A | 1/1990 | Squire | |
| 4,900,679 A | 2/1990 | Spillert et al. | |
| 4,947,851 A | 8/1990 | Sarvazyan et al. | |
| 5,007,291 A | 4/1991 | Walters et al. | |
| 5,016,469 A | 5/1991 | Henderson | |
| 5,038,787 A | 8/1991 | Antich et al. | |
| 5,056,357 A | 10/1991 | Dymling et al. | |
| 5,078,013 A | 1/1992 | Kuramochi et al. | |
| 5,081,995 A | 1/1992 | Lu et al. | |
| 5,082,418 A | 1/1992 | Poux et al. | |
| 5,086,775 A * | 2/1992 | Parker .................. G01H 9/008 600/438 | |
| 5,104,975 A | 4/1992 | McCormick et al. | |
| 5,115,808 A | 5/1992 | Popovic et al. | |
| 5,205,159 A | 4/1993 | Carr, Jr. | |
| 5,234,839 A | 8/1993 | McCormick et al. | |
| 5,265,612 A | 11/1993 | Sarvazyan et al. | |
| 5,273,517 A | 12/1993 | Barone et al. | |
| 5,311,908 A | 5/1994 | Barone et al. | |
| 5,331,964 A | 7/1994 | Trahey et al. | |
| 5,408,882 A | 4/1995 | McKinley et al. | |
| 5,431,054 A | 7/1995 | Reeves et al. | |
| 5,439,157 A | 8/1995 | Geier et al. | |
| 5,469,743 A | 11/1995 | Zorn | |
| 5,473,536 A | 12/1995 | Wimmer | |
| 5,474,225 A | 12/1995 | Geier et al. | |
| 5,487,387 A | 1/1996 | Trahey et al. | |
| RE35,171 E | 3/1996 | McCormick et al. | |
| 5,524,636 A | 6/1996 | Sarvazyan et al. | |
| 5,533,402 A | 7/1996 | Sarvazyan et al. | |
| 5,605,154 A | 2/1997 | Ries et al. | |
| 5,606,971 A | 3/1997 | Sarvazyan et al. | |
| 5,614,670 A | 3/1997 | Nazarian et al. | |
| 5,655,535 A | 8/1997 | Friemel et al. | |
| 5,657,760 A | 8/1997 | Ying et al. | |
| 5,659,129 A | 8/1997 | Asoyan et al. | |
| 5,673,699 A | 10/1997 | Trahey et al. | |
| 5,678,565 A | 10/1997 | Sarvazyan | |
| 5,681,996 A | 10/1997 | White | |
| 5,706,815 A | 1/1998 | Sarvazyan et al. | |
| 5,714,688 A | 2/1998 | Buttram et al. | |
| 5,720,708 A | 2/1998 | Lu et al. | |
| 5,744,898 A | 4/1998 | Smith et al. | |
| 5,777,229 A | 7/1998 | Geier et al. | |
| 5,785,663 A | 7/1998 | Sarvazyan | |
| 5,800,781 A | 9/1998 | Gavin et al. | |
| 5,804,698 A | 9/1998 | Belonenko et al. | |
| 5,810,731 A | 9/1998 | Sarvazyan et al. | |
| 5,836,894 A | 11/1998 | Sarvazyan | |
| 5,854,423 A | 12/1998 | Venegas | |
| 5,860,934 A | 1/1999 | Sarvazyan | |
| 5,899,861 A | 5/1999 | Friemel et al. | |
| 5,903,516 A | 5/1999 | Greenleaf et al. | |
| 5,921,928 A | 7/1999 | Greenleaf et al. | |
| 5,922,018 A | 7/1999 | Sarvazyan | |
| 5,952,578 A | 9/1999 | White | |
| 5,991,239 A | 11/1999 | Fatemi-Booshehri et al. | |
| 6,016,701 A | 1/2000 | McClelland et al. | |
| 6,039,691 A | 3/2000 | Walker et al. | |
| 6,068,597 A | 5/2000 | Lin | |
| 6,070,466 A | 6/2000 | Taran et al. | |
| 6,083,159 A | 7/2000 | Driscoll, Jr. et al. | |
| 6,105,431 A | 8/2000 | Duffill et al. | |
| 6,114,135 A | 9/2000 | Goldstein | |
| 6,117,081 A | 9/2000 | Jago et al. | |
| 6,142,959 A | 11/2000 | Sarvazyan et al. | |
| 6,148,224 A | 11/2000 | Jensen | |
| 6,155,117 A | 12/2000 | Stevens et al. | |
| 6,213,950 B1 | 4/2001 | Cespedes et al. | |
| 6,225,126 B1 | 5/2001 | Cohen et al. | |
| 6,246,895 B1 | 6/2001 | Plewes | |
| 6,264,609 B1 | 7/2001 | Herrington et al. | |
| 6,270,459 B1 | 8/2001 | Konofagou et al. | |
| 6,277,074 B1 | 8/2001 | Chaturvedi et al. | |
| 6,283,917 B1 | 9/2001 | Jago et al. | |
| 6,288,542 B1 | 9/2001 | Proksa et al. | |
| 6,293,156 B1 | 9/2001 | Shen et al. | |
| 6,306,095 B1 * | 10/2001 | Holley .................. A61B 8/481 600/458 | |
| 6,360,610 B1 | 3/2002 | Jarzynski et al. | |
| 6,371,912 B1 | 4/2002 | Nightingale et al. | |
| 6,385,474 B1 | 5/2002 | Rather et al. | |
| 6,402,704 B1 | 6/2002 | McMorrow | |
| 6,412,344 B1 | 7/2002 | Danicich et al. | |
| 6,432,236 B1 | 8/2002 | Leemon et al. | |
| 6,454,714 B1 | 9/2002 | Ng et al. | |
| 6,486,669 B1 | 11/2002 | Sinkus et al. | |
| 6,488,626 B1 * | 12/2002 | Lizzi .................. A61B 8/0858 600/437 | |
| 6,494,834 B2 | 12/2002 | Konofagou et al. | |
| 6,508,768 B1 | 1/2003 | Hall et al. | |
| 6,511,427 B1 | 1/2003 | Sliwa, Jr. et al. | |
| 6,511,429 B1 | 1/2003 | Fatemi et al. | |
| 6,514,204 B2 | 2/2003 | Alam et al. | |
| 6,520,913 B1 | 2/2003 | Pesavento | |
| 6,535,835 B1 | 3/2003 | Rubin et al. | |
| 6,537,819 B2 | 3/2003 | Cohen et al. | |

(56) References Cited

U.S. PATENT DOCUMENTS

| | | |
|---|---|---|
| 6,546,278 B2 | 4/2003 | Walsh |
| 6,561,981 B2 | 5/2003 | Bonnefous |
| 6,569,108 B2 | 5/2003 | Sarvazyan et al. |
| 6,573,104 B2 | 6/2003 | Carr, Jr. et al. |
| 6,613,573 B1 | 9/2003 | Cohen |
| 6,620,115 B2 | 9/2003 | Sarvazyan et al. |
| 6,626,049 B1 | 9/2003 | Ao |
| 6,632,678 B2 | 10/2003 | Aiken et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,705,993 B2 | 3/2004 | Ebbini et al. |
| 6,709,407 B2 | 3/2004 | Fatemi |
| 6,716,168 B2 | 4/2004 | Nock et al. |
| 6,726,629 B1 | 4/2004 | Frinking et al. |
| 6,728,567 B2 | 4/2004 | Rather et al. |
| 6,758,815 B2 | 7/2004 | Bernardi |
| 6,763,698 B2 | 7/2004 | Greenwood |
| 6,764,448 B2 | 7/2004 | Trahey |
| 6,770,033 B1 | 8/2004 | Fink et al. |
| 6,787,363 B2 | 9/2004 | Cohen et al. |
| 6,797,519 B2 | 9/2004 | Cohen et al. |
| 6,824,516 B2 | 11/2004 | Batten et al. |
| 6,833,703 B2 | 12/2004 | Sinkus et al. |
| 6,837,109 B2 | 1/2005 | Okuno et al. |
| 6,837,854 B2 | 1/2005 | Moore et al. |
| 6,851,319 B2 | 2/2005 | Ziola et al. |
| 6,875,176 B2 | 4/2005 | Mourad et al. |
| 6,890,299 B2 | 5/2005 | Cohen et al. |
| 6,899,680 B2 | 5/2005 | Hoff et al. |
| 6,926,672 B2 | 8/2005 | Moore et al. |
| 6,937,886 B2 | 8/2005 | Zavislan |
| 6,939,298 B2 | 9/2005 | Brown et al. |
| 6,949,074 B2 | 9/2005 | Fatemi |
| 6,951,540 B2 | 10/2005 | Ebbini et al. |
| 6,951,544 B2 | 10/2005 | Trahey et al. |
| 6,964,640 B2 | 11/2005 | Zumeris et al. |
| 6,984,208 B2 | 1/2006 | Cheng |
| 6,984,209 B2 | 1/2006 | Hynynen et al. |
| 6,984,210 B2 | 1/2006 | Chambers et al. |
| 6,984,211 B2 | 1/2006 | Hao et al. |
| 7,001,335 B2 | 2/2006 | Adachi et al. |
| 7,016,725 B2 | 3/2006 | Palti |
| 7,022,077 B2 | 4/2006 | Mourad et al. |
| 7,025,253 B2 | 4/2006 | Sinkus et al. |
| 7,034,534 B2 | 4/2006 | Ehman et al. |
| 7,042,218 B2 | 5/2006 | Sellers |
| 7,089,054 B2 | 8/2006 | Palti |
| 7,114,373 B2 | 10/2006 | Hazelden et al. |
| 7,136,699 B2 | 11/2006 | Palti |
| 7,146,210 B2 | 12/2006 | Palti |
| 7,175,599 B2 | 2/2007 | Hynynen et al. |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |
| 7,207,939 B2 | 4/2007 | Husher |
| 7,225,010 B1 | 5/2007 | Zavislan |
| 7,240,556 B2 | 7/2007 | Georgeson et al. |
| 7,252,004 B2 | 8/2007 | Fink et al. |
| 7,261,861 B2 | 8/2007 | Kautzky |
| 7,268,548 B2 | 9/2007 | Sellers |
| 7,272,431 B2 | 9/2007 | McGrath |
| 7,275,439 B2 | 10/2007 | Zagzebski et al. |
| 7,285,092 B2 | 10/2007 | Duric et al. |
| 7,291,109 B1 | 11/2007 | Sarvazyan |
| 7,307,423 B2 | 12/2007 | Ehman et al. |
| 7,333,852 B2 | 2/2008 | Palti |
| 7,344,509 B2 | 3/2008 | Hynynen et al. |
| 7,367,948 B2 | 5/2008 | O'Donnell et al. |
| 7,370,534 B2 | 5/2008 | Lasser et al. |
| 7,374,538 B2 | 5/2008 | Nightingale et al. |
| 7,399,637 B2 | 7/2008 | Wright et al. |
| 7,422,905 B2 | 9/2008 | Clague et al. |
| 7,439,069 B2 | 10/2008 | Nippoldt et al. |
| 7,439,736 B2 | 10/2008 | Meaney et al. |
| 7,444,875 B1 | 11/2008 | Wu et al. |
| 7,467,011 B2 | 12/2008 | Palti |
| 7,519,420 B2 | 4/2009 | Palti |
| 7,520,172 B2 | 4/2009 | Gifford et al. |
| 7,520,855 B2 | 4/2009 | Tamano et al. |
| 7,524,670 B2 | 4/2009 | Cohen et al. |
| 7,547,283 B2 | 6/2009 | Mourad et al. |
| 7,549,985 B2 | 6/2009 | O'Donnell |
| 7,553,283 B2 | 6/2009 | Sandrin et al. |
| 7,565,205 B2 | 7/2009 | Palti |
| 7,565,206 B2 | 7/2009 | Palti |
| 7,597,665 B2 | 10/2009 | Wilk et al. |
| 7,599,745 B2 | 10/2009 | Palti |
| 7,599,746 B2 | 10/2009 | Palti |
| 7,611,465 B2 | 11/2009 | Antich et al. |
| 7,650,795 B2 | 1/2010 | Abousleiman et al. |
| 7,669,477 B2 | 3/2010 | Georgeson et al. |
| 7,706,890 B2 | 4/2010 | Palti |
| 7,713,201 B2 | 5/2010 | Chen et al. |
| 7,715,921 B2 | 5/2010 | Palti |
| 7,731,661 B2 | 6/2010 | Salcudean et al. |
| 7,732,213 B2 | 6/2010 | Cohen et al. |
| 7,740,051 B2 | 6/2010 | Iizuka et al. |
| 7,744,537 B2 | 6/2010 | Kanai et al. |
| 7,753,847 B2 | 7/2010 | Greenleaf et al. |
| 7,785,259 B2 | 8/2010 | Zheng et al. |
| 7,804,595 B2 | 9/2010 | Matula et al. |
| 7,805,201 B2 | 9/2010 | Palti |
| 7,806,823 B2 | 10/2010 | Sakai et al. |
| 7,811,234 B2 | 10/2010 | McGrath |
| 7,815,574 B2 | 10/2010 | Mourad et al. |
| 7,819,824 B2 | 10/2010 | Sarvazyan et al. |
| 7,822,243 B2 | 10/2010 | Demharter |
| 7,841,983 B2 | 11/2010 | Harada et al. |
| 7,857,766 B2 | 12/2010 | Lasater et al. |
| 7,871,379 B2 | 1/2011 | Ohtsuka |
| 7,871,406 B2 | 1/2011 | Nields et al. |
| 7,890,183 B2 | 2/2011 | Palti et al. |
| 7,892,188 B2 | 2/2011 | Walker et al. |
| 7,901,355 B2 | 3/2011 | Querleux et al. |
| 7,905,148 B2 | 3/2011 | Righetti et al. |
| 7,912,540 B2 | 3/2011 | Palti |
| 7,912,661 B2 | 3/2011 | Zeng |
| 7,917,227 B2 | 3/2011 | Palti |
| 7,922,674 B2 | 4/2011 | Sarvazyan et al. |
| 7,927,279 B2 | 4/2011 | Kubota et al. |
| 7,935,058 B2 | 5/2011 | Dupps, Jr. et al. |
| 7,938,778 B2 | 5/2011 | Sakai |
| 7,949,498 B2 | 5/2011 | Walker et al. |
| 7,955,278 B1 | 6/2011 | Sarvazyan |
| 7,966,882 B2 | 6/2011 | Greenwood |
| 7,971,630 B2 | 7/2011 | Iizuka et al. |
| 7,972,271 B2 | 7/2011 | Johnson et al. |
| 7,975,555 B2 | 7/2011 | Zhuang et al. |
| 7,987,718 B2 | 8/2011 | Huber et al. |
| 7,993,271 B2 | 8/2011 | Liu et al. |
| 7,999,945 B2 | 8/2011 | Zara |
| 8,019,414 B2 | 9/2011 | Palti |
| 8,027,738 B2 | 9/2011 | Palti |
| 8,052,602 B2 | 11/2011 | Sunagawa et al. |
| 8,052,622 B2 | 11/2011 | Egorov et al. |
| 8,058,023 B2 | 11/2011 | Gurbel |
| 8,066,644 B2 | 11/2011 | Sarkar et al. |
| 8,100,831 B2 | 1/2012 | Hiltawsky et al. |
| 8,107,694 B2 | 1/2012 | Hamilton et al. |
| 8,118,744 B2 | 2/2012 | Palmeri et al. |
| 8,121,670 B2 | 2/2012 | Zavislan |
| 8,137,275 B2 | 3/2012 | Fan et al. |
| 8,147,410 B2 | 4/2012 | Zheng |
| 8,150,128 B2 | 4/2012 | Konofagou et al. |
| 8,155,416 B2 | 4/2012 | Nields et al. |
| 8,155,725 B2 | 4/2012 | Pernot et al. |
| 8,170,684 B2 | 5/2012 | Palti |
| 8,175,698 B2 | 5/2012 | Palti et al. |
| 8,184,351 B2 | 5/2012 | Mills et al. |
| 8,187,187 B2 | 5/2012 | Fan et al. |
| 8,187,208 B2 | 5/2012 | Egorov et al. |
| 8,197,408 B2 | 6/2012 | Fan et al. |
| 8,207,733 B2 | 6/2012 | Meaney et al. |

(56) References Cited

U.S. PATENT DOCUMENTS

| | | |
|---|---|---|
| 8,225,666 B2 | 7/2012 | Mcaleavey |
| 8,244,345 B2 | 8/2012 | Palti |
| 8,249,691 B2 | 8/2012 | Chase et al. |
| 8,267,865 B2 | 9/2012 | Hoyt et al. |
| 8,281,663 B2 | 10/2012 | Ehman et al. |
| 8,286,467 B2 | 10/2012 | Fatemi et al. |
| 8,287,455 B2 | 10/2012 | Phung |
| 8,305,076 B2 | 11/2012 | Sack et al. |
| 8,306,293 B2 | 11/2012 | Walker |
| 8,323,199 B2 | 12/2012 | Salcudean et al. |
| 8,325,877 B2 | 12/2012 | Abenaim |
| 8,347,692 B2 | 1/2013 | Sinkus et al. |
| 8,353,096 B2 | 1/2013 | Ladabaum |
| 8,376,946 B2 | 2/2013 | Littrup et al. |
| 8,398,549 B2 | 3/2013 | Palmeri et al. |
| 8,398,550 B2 | 3/2013 | Insana et al. |
| 8,403,850 B2 | 3/2013 | Varghese et al. |
| 8,406,870 B2 | 3/2013 | Palti |
| 8,409,099 B2 | 4/2013 | Vitek et al. |
| 8,419,642 B2 | 4/2013 | Sandrin et al. |
| 8,419,659 B2 | 4/2013 | Egorov et al. |
| 8,425,424 B2 | 4/2013 | Zadicario et al. |
| 8,428,687 B2 | 4/2013 | Konofagou et al. |
| 8,447,395 B2 | 5/2013 | Palti et al. |
| 8,447,396 B2 | 5/2013 | Palti et al. |
| 8,465,533 B2 | 6/2013 | Palti |
| 8,469,891 B2 | 6/2013 | Maleke et al. |
| 8,494,791 B2 | 7/2013 | Hazard et al. |
| 8,500,639 B2 | 8/2013 | Yao |
| 8,523,787 B2 | 9/2013 | Ludwin et al. |
| 8,545,407 B2 | 10/2013 | Bercoff et al. |
| 8,545,410 B2 | 10/2013 | Hope Simpson et al. |
| 8,548,759 B2 | 10/2013 | Walker et al. |
| 8,556,888 B2 | 10/2013 | Nields et al. |
| 8,602,994 B2 | 12/2013 | Zheng et al. |
| 8,606,343 B2 | 12/2013 | Zavislan |
| 8,608,672 B2 | 12/2013 | Vortman et al. |
| 8,615,285 B2 | 12/2013 | Ehman et al. |
| 8,617,073 B2 | 12/2013 | Prus et al. |
| 8,647,276 B2 * | 2/2014 | Tabaru ............... A61B 8/08 600/437 |
| 8,685,636 B2 | 4/2014 | Braun et al. |
| 8,697,449 B2 | 4/2014 | Gregor et al. |
| 8,726,734 B1 * | 5/2014 | Lin ............... B06B 1/0622 73/626 |
| 8,740,818 B2 | 6/2014 | Walker et al. |
| 8,809,007 B2 | 8/2014 | Christ et al. |
| 8,889,370 B2 | 11/2014 | Kappel et al. |
| 8,932,826 B2 | 1/2015 | Zander |
| 8,945,825 B2 | 2/2015 | Dekevic et al. |
| 2001/0031934 A1 | 10/2001 | Sarvazyan et al. |
| 2001/0037074 A1 | 11/2001 | Sarvazyan et al. |
| 2001/0053384 A1 | 12/2001 | Greenleaf et al. |
| 2002/0004630 A1 | 1/2002 | Sarvazyan et al. |
| 2002/0013530 A1 | 1/2002 | Cespedes et al. |
| 2002/0040187 A1 | 4/2002 | Alam et al. |
| 2002/0081741 A1 | 6/2002 | Braun et al. |
| 2002/0143275 A1 | 10/2002 | Sarvazyan et al. |
| 2003/0013958 A1 | 1/2003 | Govari et al. |
| 2003/0073244 A1 | 4/2003 | Cohen et al. |
| 2003/0078227 A1 | 4/2003 | Greenleaf et al. |
| 2003/0083595 A1 | 5/2003 | Fatemi |
| 2003/0105398 A1 | 6/2003 | Vitek |
| 2003/0113929 A1 | 6/2003 | Baugh et al. |
| 2003/0128033 A1 | 7/2003 | Sinkus et al. |
| 2003/0153850 A1 | 8/2003 | Davis et al. |
| 2003/0170883 A1 | 9/2003 | Martin et al. |
| 2003/0171676 A1 | 9/2003 | Trahey et al. |
| 2003/0204141 A1 | 10/2003 | Nock et al. |
| 2003/0236635 A1 | 12/2003 | Priev et al. |
| 2004/0065143 A1 | 4/2004 | Husher |
| 2004/0068184 A1 | 4/2004 | Trahey et al. |
| 2004/0076546 A1 | 4/2004 | Bissett |
| 2004/0123671 A1 | 7/2004 | Priev et al. |
| 2004/0133103 A1 | 7/2004 | Adachi et al. |
| 2004/0162504 A1 | 8/2004 | Fatemi |
| 2004/0167403 A1 | 8/2004 | Nightingale et al. |
| 2004/0199077 A1 | 10/2004 | Hao et al. |
| 2004/0214337 A1 | 10/2004 | Kautzky |
| 2004/0225215 A1 | 11/2004 | Querleux et al. |
| 2004/0254503 A1 | 12/2004 | Sarvazyan et al. |
| 2004/0267121 A1 | 12/2004 | Sarvazyan et al. |
| 2004/0267165 A1 | 12/2004 | Sarvazyan et al. |
| 2005/0004463 A1 | 1/2005 | Chen et al. |
| 2005/0015001 A1 | 1/2005 | Lec et al. |
| 2005/0053305 A1 | 3/2005 | Li et al. |
| 2005/0104588 A1 | 5/2005 | Sinkus et al. |
| 2005/0148899 A1 | 7/2005 | Walker et al. |
| 2005/0165306 A1 | 7/2005 | Zheng et al. |
| 2005/0215899 A1 | 9/2005 | Trahey et al. |
| 2005/0252295 A1 | 11/2005 | Fink et al. |
| 2006/0024746 A1 | 2/2006 | Sarvazyan |
| 2006/0207343 A1 | 9/2006 | Clifton et al. |
| 2006/0238763 A1 | 10/2006 | Sarvazyan et al. |
| 2006/0258934 A1 | 11/2006 | Zenge et al. |
| 2007/0016022 A1 | 1/2007 | Blalock et al. |
| 2007/0038095 A1 | 2/2007 | Greenleaf et al. |
| 2007/0038152 A1 | 2/2007 | Sarvazyan et al. |
| 2007/0059840 A1 | 3/2007 | Cohen et al. |
| 2007/0184508 A1 | 8/2007 | Cohen et al. |
| 2007/0276236 A1 | 11/2007 | Jong |
| 2008/0038828 A1 | 2/2008 | Cohen et al. |
| 2008/0076099 A1 | 3/2008 | Sarvazyan et al. |
| 2008/0097211 A1 | 4/2008 | Sarvazyan et al. |
| 2008/0154154 A1 | 6/2008 | Sarvazyan et al. |
| 2008/0194967 A1 | 8/2008 | Sliwa et al. |
| 2008/0221484 A1 | 9/2008 | Sarvazyan et al. |
| 2008/0249408 A1 | 10/2008 | Palmeri et al. |
| 2008/0261261 A1 | 10/2008 | Grimes et al. |
| 2008/0297169 A1 | 12/2008 | Greenquist et al. |
| 2008/0302187 A1 | 12/2008 | Huber et al. |
| 2009/0005707 A1 | 1/2009 | Sarvazyan et al. |
| 2009/0052272 A1 | 2/2009 | Sarvazyan |
| 2009/0052273 A1 | 2/2009 | Sarvazyan |
| 2009/0053688 A1 | 2/2009 | Bystryak et al. |
| 2009/0056453 A1 | 3/2009 | McAleavey |
| 2009/0093724 A1 | 4/2009 | Pernot et al. |
| 2009/0099485 A1 | 4/2009 | Sarvazyan et al. |
| 2009/0112483 A1 | 4/2009 | Cohen |
| 2009/0114019 A1 | 5/2009 | Fatemi et al. |
| 2009/0124901 A1 | 5/2009 | Fink et al. |
| 2009/0216128 A1 | 8/2009 | Sarvazyan |
| 2010/0010346 A1 | 1/2010 | Greenleaf et al. |
| 2010/0143241 A1 | 6/2010 | Johnson et al. |
| 2010/0170342 A1 | 7/2010 | Sinkus et al. |
| 2010/0191110 A1 | 7/2010 | Insana et al. |
| 2010/0204643 A1 | 8/2010 | Sarvazyan |
| 2010/0222678 A1 | 9/2010 | Bercoff et al. |
| 2010/0241001 A1 | 9/2010 | Palmeri et al. |
| 2010/0274130 A1 | 10/2010 | Anand et al. |
| 2011/0015547 A1 | 1/2011 | Sarvazyan et al. |
| 2011/0028838 A1 | 2/2011 | Pernot et al. |
| 2011/0034805 A1 | 2/2011 | Walker et al. |
| 2011/0054357 A1 | 3/2011 | Egorov et al. |
| 2011/0063950 A1 | 3/2011 | Greenleaf et al. |
| 2011/0065989 A1 | 3/2011 | Sarvazyan et al. |
| 2011/0065991 A1 | 3/2011 | Sarvazyan et al. |
| 2011/0066078 A1 | 3/2011 | Sarvazyan et al. |
| 2011/0092818 A1 | 4/2011 | Sarvazyan |
| 2011/0130660 A1 | 6/2011 | Cloutier et al. |
| 2011/0130683 A1 | 6/2011 | Sarvazyan |
| 2011/0130685 A1 | 6/2011 | Sarvazyan et al. |
| 2011/0144493 A1 | 6/2011 | Sarvazyan |
| 2011/0151491 A1 | 6/2011 | Dennis et al. |
| 2011/0166442 A1 | 7/2011 | Sarvazyan |
| 2011/0184287 A1 | 7/2011 | McAleavey |
| 2011/0196263 A1 | 8/2011 | Egorov et al. |
| 2011/0201931 A1 | 8/2011 | Palmeri et al. |
| 2011/0252352 A1 | 10/2011 | Viola et al. |
| 2011/0263978 A1 | 10/2011 | Chen et al. |
| 2011/0301465 A1 | 12/2011 | Waki |
| 2011/0319756 A1 | 12/2011 | Zheng et al. |
| 2012/0029286 A1 | 2/2012 | Sarvazyan et al. |
| 2012/0053450 A1 | 3/2012 | Salcudean et al. |

(56) References Cited

U.S. PATENT DOCUMENTS

| | | |
|---|---|---|
| 2012/0130248 A1 | 5/2012 | Fatemi |
| 2012/0143042 A1 | 6/2012 | Palmeri et al. |
| 2012/0203306 A1 | 8/2012 | Sarvazyan |
| 2012/0226158 A1 | 9/2012 | Greenleaf et al. |
| 2012/0232803 A1 | 9/2012 | Viola et al. |
| 2012/0252127 A1 | 10/2012 | Bansil |
| 2012/0259247 A1 | 10/2012 | Egorov et al. |
| 2012/0277632 A1 | 11/2012 | Sarvazyan et al. |
| 2012/0294767 A1 | 11/2012 | Viola et al. |
| 2012/0329082 A1 | 12/2012 | Viola et al. |
| 2013/0031981 A1 | 2/2013 | Montaldo et al. |
| 2013/0058195 A1 | 3/2013 | Cloutier et al. |
| 2013/0079645 A1 | 3/2013 | Amirana et al. |
| 2013/0102862 A1 | 4/2013 | Mercader et al. |
| 2013/0131754 A1 | 5/2013 | Sarvazyan |
| 2013/0144191 A1 | 6/2013 | Egorov et al. |
| 2013/0165778 A1 | 6/2013 | McAleavey |
| 2013/0190584 A1 | 7/2013 | Walker et al. |
| 2013/0237807 A1 | 9/2013 | Maitre et al. |
| 2013/0237821 A1 | 9/2013 | Amador et al. |
| 2013/0245442 A1 | 9/2013 | Hazard et al. |
| 2014/0154706 A1 | 6/2014 | Zheng et al. |
| 2014/0242621 A1 | 8/2014 | Patzke et al. |
| 2014/0328732 A1 | 11/2014 | Delmenico et al. |
| 2015/0216507 A1* | 8/2015 | Greenleaf ............ A61B 8/4494 600/438 |

FOREIGN PATENT DOCUMENTS

| | | |
|---|---|---|
| CN | 103649751 | 3/2014 |
| DE | 202014002289 | 10/2014 |
| EP | 2555704 | 2/2013 |
| EP | 2676136 | 12/2013 |
| EP | 2676143 | 12/2013 |
| EP | 2690437 | 1/2014 |
| EP | 1618375 | 5/2014 |
| EP | 2772762 | 9/2014 |
| EP | 2484776 | 12/2014 |
| EP | 2634584 | 12/2014 |
| EP | 2513647 | 4/2015 |
| JP | 2005279250 A | 10/2005 |
| JP | 5401062 | 1/2014 |
| JP | 5563470 | 6/2014 |
| JP | 5655091 | 1/2015 |
| WO | 2011/035162 | 3/2011 |
| WO | 2011/127436 | 10/2011 |
| WO | 2012/159021 | 11/2012 |
| WO | 2013/105986 | 7/2013 |
| WO | 2013/105987 | 7/2013 |
| WO | 2014/088987 | 6/2014 |
| WO | 2014/138533 | 9/2014 |
| WO | 2014/144259 | 9/2014 |
| WO | 2014/186411 | 11/2014 |
| WO | 2015/017535 | 2/2015 |
| WO | 2015/034646 | 3/2015 |

OTHER PUBLICATIONS

Anderson, M.E., "Multi-Dimensional Velocity Estimation with Ultrasound Using Spatial Quadrature," IEEE Transactions on Ultrasonics, Ferroelectrics, and Frequency Control, vol. 45, No. 3, 1998, pp. 852-861.

Anderson, Jr., F.A. et al., "Preventing Deep Vein Thrombosis and Pulmonary Embolism," Center for Outcomes Research, U Mass Med Center, 1998, 23 pages.

Becker, R.C., "Cell-Based Models of Coagulation: A Paradigm in Evolution," Journal of Thrombosis and Thrombolysis, vol. 20, No. 1, pp. 65-68.

Beer, A.E., "Thrombophilia: Inherited and Acquired," Center for Reproductive Immunology & Genetics, http://repro-med.net/papers/thromb.php, 2004, 6 pages.

Bell, C.R.W. et al., "Thrombelastographic evaluation of coagulation in transurethral prostatectomy," British Journal of Urology, vol. 78, No. 5, 1996, pp. 737-741.

Bercoff, J. et al., "In vivo Breast Tumor Detection Using Transient Elastography," Ultrasound in Medicine & Biology, vol. 29, No. 10, 2003, pp. 1387-1396.

Bercoff, J. et al., "Supersonic Shear Imaging: A New Technique for Soft Tissue Elasticity Mapping," IEEE Transactions on Ultrasonics, Ferroelectrics, and Frequency Control, vol. 51, No. 4, 2004, pp. 396-409.

Bilgen, M. et al., "Error analysis in acoustic elastography. II. Strain estimation and SNR analysis", Journal of the Acoustical Society of America, vol. 101, 1997, pp. 1147-1154.

Bohs, L.N. et al., "A Real Time System for Quantifying and Displaying Two-Dimensional Velocities Using Ultrasound," Ultrasound in Medicine & Biology, vol. 19, No. 9, 1993, pp. 751-761.

Bombeli, T. et al., "Updates in perioperative coagulation: physiology and management of thromboembolism and haemorrhage," British Journal of Anaesthesia; vol. 93, No. 2, 2004, pp. 275-287.

Bonnefous, O. et al., "Time Domain Formulation of Pulse-Doppler Ultrasound and Blood Velocity Estimation by Cross Correlation," Ultrasonic Imaging 8, 1986, pp. 73-85.

Brock, T.K. et al., "Assessing Thrombin Generation at the Point of Care," Clinical Chemistry, vol. 55, No. 3, 2009, pp. 389-399.

Carr, Jr., M.E., "In Vitro Assessment of Platelet Function," Transfusion of Medicine Reviews, vol. 11, No. 2, 1997, pp. 106-115.

Carroll, R.C. et al., "Measurement of functional fibrinogen levels using the Thrombelastograph," Journal of Clinical Anesthesia, vol. 20, No. 3, 2008, pp. 186-190.

Carter, G.C., "Coherence and Time Delay Estimation," Proceedings of the IEEE, vol. 75, No. 2, 1987, pp. 236-255.

Chakroun, T. et al., "The influence of fibrin polymerization and platelet-mediated contractile forces on citrated whole blood thromboelastography profile," Thrombosis and Haemostasis, vol. 95, No. 5, 2006, pp. 822-828.

Chandler, W.L. et al., "Development of a rapid emergency hemorrhage panel," Transfusion, vol. 50, No. 12, 2010, pp. 2547-2552.

Chandler, W.L. et al., "Estimating the rate of thrombin and fibrin generation in vivo during cardiopulmonary bypass," Blood, vol. 101, No. 11, 2003, pp. 4355-4362.

Chaturvedi, P. et al., "Testing the Limitations of 2-D Companding for Strain Imaging Using Phantoms," IEEE Transactions on Ultrasonics, Ferroelectrics, and Frequency Control, vol. 45, No. 4, 1998, pp. 1022-1031.

Chavez, J.J., "A Novel Thrombelastograph Tissue Factor/Kaolin Assay of Activated Clotting Times for Monitoring Heparin Anticoagulation During Cardiopulmonary Bypass," Anesthesia and Analgesia; vol. 99, No. 5, 2004, pp. 1290-1294.

Chonavel, T. et al., "Fast adaptive eigenvalue decomposition: a maximum likelihood approach," Signal Processing, vol. 83, 2003, pp. 307-324.

Cohn, N.A. et al., "An Elasticity Microscope. Part I: Methods," IEEE Transactions on Ultrasonics, Ferroelectrics, and Frequency Control, vol. 44, No. 6, 1997, pp. 1304-1319.

Cohn, N.A. et al., "An Elasticity Microscope. Part II: Experimental Results," IEEE Transactions on Ultrasonics, Ferroelectrics, and Frequency Control, vol. 44, No. 6, 1997, pp. 1320-1331.

Craft, R.M. et al., "A novel modification of the Thrombelastograph assay, isolating platelet function, correlates with optical platelet aggregation," The Journal of Laboratory and Clinical Medicine, vol. 143, No. 5, 2004, pp. 301-309.

Curry, A. et al., "Convention and near-patient tests of coagulation," British Journal of Anaesthesia, vol. 7, No. 2, Apr. 2007, pp. 45-50.

Dahlbäck, B., "Blood coagulation," The Lancet, Haematology, vol. 355, 2000, pp. 1627-1632.

Despotis, G.J. et al., "Monitoring of hemostasis in cardiac surgical patients: impact of point-of-care testing on blood loss and transfusion outcomes," Clinical Chemistry, vol. 43, No. 9, 1997, pp. 1684-1696.

Embree, P.M. et al., "Volumetric Blood Flow via Time-Domain Correlation: Experimental Verification," IEEE Transactions on Ultrasonics, Ferroelectrics, and Frequency Control, vol. 37, No. 2, 1990, pp. 176-189.

(56) References Cited

OTHER PUBLICATIONS

Emelianov, S.Y. et al., "Ultrasound Elasticity Imaging of Deep Venous Thrombosis," IEEE Ultrasonics Symposium, 2000, pp. 1791-1794.
Evans, P.A. et al., "Rheometry and associated techniques for blood coagulation studies," Medical Engineering and Physics, 2007, pp. 671-679.
Fatemi, M. et al., "Application of Radiation Force in Noncontact Measurement of the Elastic Parameters," Ultrasonic Imaging, vol. 21, No. 2, 1999, pp. 147-154.
Fatemi, M. et al., "C-Scan Imaging by Radiation Force Stimulated Acoustic Emission Method," IEEE Ultrasonics Symposium, 1996, pp. 1459-1462.
Fatemi, M. et al., "Ultrasound-Stimulated Vibro-Acoustic Spectography," Science, vol. 280, 1998, pp. 82-85.
Ferraris, V.A. et al., "2011 Update to the Society of Thoracic Surgeons and the Society of Cardiovascular Anesthesiologists Blood Conservation Clinical Practice Guidelines," Annals of Thoracic Surgery, vol. 91, 2011, pp. 944-982.
Fertner, A. et al., "Comparison of Various Time Delay Estimation Methods by Computer Simulation," IEEE Transactions on Acoustics, Speech, and Signal Processing, vol. ASSP-34, No. 5, 1986, pp. 1329-1330.
Flax, S.W. et al., "Phase-Aberration Correction Using Signals From Point Reflectors and Diffuse Scatterers: Basic Principles," IEEE Transactions on Ultrasonics, Ferroelectrics, and Frequency Control, vol. 35, No. 6, 1988, pp. 758-767.
Freedman, K.B. et al., "A Meta-Analysis of Thromboembolic Prophylaxis Following Elective Total Hip Arthroplasty," The Journal of Bone and Joint Surgery, vol. 82-A, No. 7, 2000, pp. 929-938.
Gaetano, G. de et al., "Effect of Platelets on Clot Structuration, a Thrombelastographic Study," Thrombosis Research, vol. 3, 1973, pp. 425-435.
Gallippi, C.M. et al., "Adaptive Clutter Filtering Via Blind Source," Ultrasonic Imaging, vol. 24, No. 4, 2002, pp. 193-214.
Gallippi, C.M. et al., "BSS-Based Filtering of Physiological and ARFI-Induced Tissue and Blood Motion," Ultrasound in Medicine and Biology, vol. 29, No. 11, 2003, pp. 1583-1592.
Gallippi, C.M. et al., "Complex Blind Source Separation for Acoustic Radiation Force Impulse Imaging in the Peripheral Vasculature, In Vivo," IEEE Ultrasonics Symposium, vol. 1, 2004, pp. 596-601.
Ganter, M.T. et al., "Active, Personalized, and Balanced Coagulation Management Saves Lives in Patients with Massive Bleeding," Anesthesiology, vol. 113, No. 5, 2010, pp. 1016-1018.
Ganter, M.T. et al., "Coagulation Monitoring: Current Techniques and Clinical Use of Viscoelastic Point-of-Care Coagulation Devices," Anesthesia and Analgesia, vol. 106, No. 5, 2008, pp. 1366-1375.
Gauss, R.C. et al., "Adaptive Imaging in the Thyroid Using Fundamental and Harmonic Echo Data," IEEE Ultrasonics Symposium, 1999, pp. 1515-1519.
Gauss, R.C. et al., "Wavefront Estimation in the Human Breast," Ultrasonic Imaging and Signal Processing, Proceedings of SPIE Medical Imaging, 2001, pp. 172-180.
Giunta, G. et al., "Estimation of Global Motion Parameters by Complex Linear Regression," IEEE Transactions on Image Processing, vol. 8, No. 11, 1999, pp. 1652-1657.
Glidden, P.F. et al., "Thromboelastograph Assay for Measuring the Mechanical Strength of Fibrin Sealant Clots," Clinical and Applied Thombosis/Hemostasis, vol. 6, No. 4, 2000, pp. 226-233.
Gottumukkala, V.N.R. et al., "Assessing Platelet and Fibrinogen Contribution to Clot Strength Using Modified Thromboelastography in Pregnant Women," Anesthiology and Analgesia, vol. 89, 1999, pp. 1453-1455.
Greilich, P.E. et al., "A Modified Thromboelastographic Method for Monitoring c7E3 Fab in Heparinized Patients," Anesthesia & Analgesia, vol. 84, 1997, pp. 31-38.
Greilich, P.E. et al., "Near-Site Monitoring of the Antiplatelet Drug Abciximad Using the Hemodyne Analyzer and Modified Thrombelastograph," Journal of Cardiothoracic and Vascular Anesthesia, vol. 13, No. 1, Feb. 1999, pp. 58-64.
Gurbel, P.A. et al., "Platelet Function Monitoring in Patients With Coronary Artery Disease," Journal of the American College of Cardiology, vol. 50, No. 19, 2007, pp. 1822-1834.
Harris, J.M. et al., "Evaluation of Recurrent Thrombosis and Hypercoagulability," American Family Physicians, vol. 56, No. 6, 1997, 6 pages.
Hartley, C.J., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.
Hartley, C.J, "Doppler Measurement of Acoustic Streaming," IEEE Ultrasonics Symposium, 1995, pp. 1537-1540.
Hett, D.A. et al., "Sonoclot Analysis," British Journal of Anaesthesia, vol. 75, 1995, pp. 771-776.
Hirsh, J. et al., "How we diagnose and treat deep vein thrombosis," Blood, vol. 99, No. 9, 2002, pp. 3102-3110.
Hirsh, J. et al., "Management of Deep Vein Thrombosis and Pulmonary Embolism," Circulation, American Heart Association, vol. 93, 1996, pp. 2212-2245.
Hoffman, M. et al., "A Cell-based Model of Hemostasis," Thrombosis and Haemostasis, vol. 85, 2001, pp. 958-965.
Huang, C-C et al., "Characterization of Blood Properties from Coagulating Blood of Different Hematocrits Using Ultrasonic Backscatter and Attenuation," Japanese Journal of Applied Physics, vol. 45, No. 9A, 2006, pp. 7191-7196.
Huang, C-C et al., "Detection of Blood Coagulation and Clot Formation Using Quantitative Ultrasonic Parameters," Ultrasound in Medicine and Biology, vol. 31, No. 11, 2005, pp. 1567-1573.
Ickx, B., "Point-of-Care Monitoring of Haemostasis in the OR and the ICU," European Society of Anaesthesiologists, 2004, pp. 79-83.
Ivandic, B.T. et al., "Determination of Clopidogrel Resistance by Whole Blood Platelet Aggregometry and Inhibitors of the $P2Y_{12}$ Receptor," Clinical Chemistry, vol. 52, No. 3, 2006, pp. 383-388.
Jacovitti, G. et al., "Discrete Time Techniques for Time Delay Estimation," IEEE Transactions on Signal Processing, vol. 41, No. 2, 1993, pp. 525-533.
Jensen, J.A. et al., "A New Method for Estimation of Velocity Vectors," IEEE Transactions on Ultrasonics, Ferroelectrics, and Frequency Control, vol. 45, No. 3, 1998, pp. 837-851.
Jensen, J.A. et al., "Calculation of Pressure Fields from Arbitrarily Shaped, Apodized, and Excited Ultrasound Transducers," IEEE Transactions on Ultrasonics, Ferroelectrics, and Frequency Control, vol. 39, No. 2, 1992, pp. 262-267.
Jensen, J.A., "Color flow mapping using phase shift estimation," Estimation of Blood Velocities Using Ultrasound: A Signal Processing Approach, 1996, pp. 195-225.
Jolliffe, I.T., "Principal Component Analysis," Second Edition, Springer Series in Statistics, Springer, New York, 2002, 40 pages.
Kadi, A.P. et al., "On the Performance of Regression and Step-Initialized IIR Clutter Filters for Color Doppler Systems in Diagnostic Medical Ultrasound," IEEE Transactions on Ultrasonics, Ferroelectrics, and Frequency Control, vol. 42, No. 5, 1995, pp. 927-937.
Kasai, C. et al., "Real-Time Two-Dimensional Blood Flow Imaging Using an Autocorrelation Technique," IEEE Transactions on Sonics and Ultrasonics, vol. SU-32, No. 3, 1985, pp. 458-464.
Katori, N. et al., "The Effects of Platelet Count on Clot Retraction and Tissue Plasminogen Activator-Induced Fibrinolysis on Thrombelastography," Anesthesia and Analgesia, vol. 100, No. 6, 2005, pp. 1781-1785.
Keresztes, P.A. et al., "The PFA-100: Analysis and Interpretation of a Platelet Function Measurement," The Journal of Cardiovascular Nursing, vol. 20, No. 6, 2005, pp. 405-407.
Kettner, S.C. et al., "Use of abciximab-Modified Thrombelatography in Patients Undergoing Cardiac Surgery," Anesthesia & Analgesia, vol. 89, 1999, pp. 580-584.
Khurana, S. et al., "Monitoring Platelet Glycoprotein IIb/IIa-fibrin Interaction with tissue factor-activated thromboelastography," Journal of Laboratory and Clinical Medicine, vol. 130, No. 4, 1997, pp. 401-411.

(56) References Cited

OTHER PUBLICATIONS

Khurana, S., "Thromboelastography Can Rapidly Bioassay Fibrinogen," Anesthesiology, vol. 85, No. 3A, 1996, 1 page.
Koepke, J., "Point-of-Care Coagulation Testing," Laboratory Medicine, vol. 31, No. 6, 2000, pp. 343-346.
Kruse, D.E. et al., "A New High Resolution Color Flow System Using an Eigendecomposition-Based Adaptive Filter for Clutter Rejection," IEEE Transactions on Ultrasonics, Ferroelectrics, and Frequency Control, vol. 49, No. 10, 2002, pp. 1384-1399.
Ledoux, L.A.F. et al., "Reduction of the Clutter Component in Doppler Ultrasound Signals Based on Singular Value Decomposition: a Simulation Study," Ultrasonic Imaging, vol. 19, No. 1, 1997, pp. 1-18.
Lerner, R.M. et al., "Sono-Elasticity: Medical Elasticity Images Derived from Ultrasound Signals in Mechanically Vibrated Targets," Ultrasound in Medicine & Biology, vol. 16, 1998, pp. 317-327.
Libgot, R. et al., "High frequency ultrasound characterization of the blood clotting process: intra- and inter-individual variations," IEEE Ultrasonics Symposium, pp. 2259-2262.
Loupas, T. et al., "An Axial Velocity Estimator for Ultrasound Blood Flow Imaging, Based on a Full Evaluation of the Doppler Equation by Means of a Two-Dimensional Autocorrelation Approach," IEEE Transactions on Ultrasonics, Ferroelectrics, and Frequency Control, vol. 42, No. 4, 1995, pp. 672-688.
Lubinski, M.A. et al., "Adaptive Strain Estimation Using Retrospective Processing," IEEE Transactions on Ultrasonics, Ferroelectrics, and Frequency Control, vol. 46, No. 1, 1999, pp. 97-107.
Mahla, E. et al., "Thromboelastography for Monitoring Prolonged Hypercoagulability After Major Abdominal Surgery," Anesthesia and Analgesia, vol. 92, No. 3, 2001, pp. 572-577.
Malinin, A. et al., "Validation of a VerifyNow-P2Y12® Cartridge for Monitoring Platelet Inhibition with Clopidogrel," Methods and Findings in Experimental and Clinical Pharmacology, vol. 28, No. 5, 2006, pp. 315-322.
Mauldin, Jr., F.W. et al., "Adaptive Force Sonorheometry for Assessment of Whole Blood Coagulation," Clinica Chimica Acta, vol. 411, Issues 9-10, 2010, pp. 638-644.
Mauldin, Jr., F.W. et al., "Robust Principal Component Analysis and Clustering Methods for Automated Classification of Tissue Response to ARFI Excitation," Ultrasound in Medicine & Biology, vol. 34, No. 2, 2008, pp. 309-325.
McAleavey, S.A. et al., "Estimates of Echo Correlation and Measurement Bias in Acoustic Radiation Force Impulse Imaging," IEEE Transactions on Ultrasonics, Ferroelectrics, and Frequency Control, vol. 50, No. 6, 2003, pp. 631-641.
Ng, G.C. et al., "A Comparative Evaluation of Several Algorithms for Phase Aberration Correction," IEEE Transactions on Ultrasonics, Ferroelectrics, and Frequency Control, vol. 41, No. 5, 1994, pp. 631-643.
Nielson, V.G. et al., "Effects of coagulation factor deficiency on plasma coagulation kinetics determined via thrombelastography®: critical roles of fibrinogen and factors II, VII, X and XII," Acta Anesthesiologica Scandanavia, vol. 49, No. 2, 2005, pp. 222-231.
Nightingale, K. et al., "Acoustic Radiation Force Impulse Imaging: In Vivo Demonstration of Clinical Feasibility," Ultrasound in Medicine & Biology, vol. 28, 2002, pp. 227-235.
Nightingale, K. et al., "Acoustic Remote Palpation: Initial In Vivo Results," IEEE Ultrasonics Symposium, 2000, pp. 1553-1558.
Nightingale, K. et al., "Shear-Wave Generation Using Acoustic Radiation Force: In Vivo and Ex Vivo Results," Ultrasound in Medicine & Biology, vol. 29, No. 12, 2003, pp. 1715-1723.
O'Donnell, M. et al., "Internal Displacement and Strain Imaging using Ultrasonic Speckle Tracking," IEEE Transactions on Ultrasonics, Ferroelectrics, and Frequency Control, vol. 41, No. 3, 1994, pp. 314-325.
O'Donnell, J. et al., "Role of the Thrombelastograph as an adjunctive test in thrombophilia screening," Blood Coagulation and Fibrinolysis, vol. 15, No. 3, 2004, pp. 207-211.
Oberhardt, B.J. et al., "Dry Reagent Technology for Rapid, Convenient Measurements of Blood Coagulation and Fibrinolysis," Clinical Chemistry, vol. 37, No. 4, 1991, pp. 520-526.
Ophir, J. et al., "Elastography: A Quantitative Method for Imaging the Elasticity of Biological Tissues," Ultrasonic Imaging, vol. 13, 1991, pp. 111-134.
Packham, M.A., "Role of platelets in thrombosis and hemostasis," Canadian Journal of Physiology and Pharmacology, vol. 72, No. 3, 1994, pp. 278-284.
Palmeri, M.L. et al., "Ultrasonic Tracking of Acoustic Radiation Force-Induced Displacements in Homogeneous Media," IEEE Transactions on Ultrasonics, Ferroelectrics, and Frequency Control, vol. 53, No. 7, 2006, pp. 1300-1313.
Parsons, R.E. et al., "Age determination of experimental venous thrombi by ultrasonic tissue characterization," Journal of Vascular Surgery, vol. 17, No. 3, 1993, 470-478.
Patil, A.V. et al., "3D prostate elastography: algorithm, simulations and experiments," Physics in Medicine & Biology, vol. 52, 2007, pp. 3643-3663.
Perry, D.J. et al., "Point-of-care testing in haemostasis," British Journal of Haematology, vol. 150, 2010, pp. 501-514.
Pivalizza, E.G. et al., "Perioperative thromboelastography and sonoclot analysis in morbidly obese patients," Canadian Journal of Anaesthesia, vol. 44, No. 9, 1997, pp. 942-945.
Rao, G., "Need for a Point-of-Care Assay for Monitoring Antiplatelet and Antithrombotic Therapies," Stroke, vol. 40, 2009, pp. 2271-2272.
Rubin, J.M. et al., "Clinical Application of Sonographic Elasticity Imaging for Aging of Deep Venous Thrombosis: Preliminary Findings," Journal of Ultrasound in Medicine, vol. 22, 2003, pp. 443-448.
Sakharov, D.V. et al., "Acceleration of Fibrinolysis by High-frequency Ultrasound: The Contribution of Acoustic Streaming and Temperature Rise," Thrombosis Research, vol. 100, 2000, pp. 333-340.
Sarvazyan, A.P. et al., "Shear Wave Elasticity Imagining: A New Ultrasonic Technology of Medical Diagnostics," Ultrasound in Medicine and Biology, vol. 24, No. 9, 1998, pp. 1419-1436.
Schmitt, C. et al., "Characterization of blood clot viscoelasticity by dynamic ultrasound elastography and modeling of the rheological behavior," Journal of Biomechanics, vol. 44, 2011, pp. 622-629.
Shi, X. et al., "Color Doppler Detection of Acoustic Streaming in a Hematoma Model," Ultrasound in Medicine and Biology, vol. 27, No. 9, 2001, pp. 1255-1264.
Shi, X. et al., "Color Doppler imaging of acoustic streaming in blood and clot," IEEE Ultrasonics Symposium, vol. 2, 1999, pp. 1315-1318.
Shi et al., "Experimental Investigation and Finite Element Simulation of Streaming in Blood in Cylindrical Models," IEEE Ultrasonics Symposium, vol. 2, 2000, pp. 1509-1512.
Shi, X. et al., "Quantitative investigation of acoustic streaming in blood," Journal of the Acoustical Society of America, vol. 111, No. 2, 2002, pp. 1110-1121.
Shih, C-C et al., "In Vitro Assessments of Viscoelastic Properties of Fibrin Clot by Using Acoustic Radiation Force on a Solid Sphere," IEEE Proceedings of the International Ultrasonics Symposium, 2010, pp. 479-482.
Shung, K.K. et al., "Ultrasonic Characterization of Blood During Coagulation," Journal of Clinical Ultrasound, vol. 12, 1984, pp. 147-153.
Skovoroda, A.R. et al., "Tissue Elasticity Reconstruction Based on Ultrasonic Displacement and Strain Images," IEEE Transactions on Ultrasonics, Ferroelectrics, and Frequency Control, vol. 42, No. 4, 1995, pp. 747-765.
Srinivasan, S. et al., "Elastographic Imaging Using Staggered Strain Estimates," Ultrasonic Imaging, vol. 24, 2002, pp. 229-245.
Strobach, P., "Low-Rank Adaptive Filters," IEEE Transactions on Signal Processing, vol. 44, No. 12, 1996, pp. 2932-2947.
Sugimoto, T. et al., "Tissue Hardness Measurement Using the Radiation Force of Focused Ultrasound," Proceedings of the IEEE Ultrasonic Symposium, 1990, pp. 1377-1380.

(56) References Cited

OTHER PUBLICATIONS

Sumino, Y. et al., "Measurements of ultrasonic pulse arrival time differences produced by abdominal wall specimens," Journal of the Acoustical Society of America, vol. 90, No. 6, 1991, pp. 2924-2930.
Thuerlemann, C. et al., "Monitoring Thrombin Generation by Electrochemistry: Development of an Amperometric Biosensor Screening Test for Plasma and Whole Blood," Clinical Chemistry, vol. 55, No. 3, 2009, pp. 505-512.
Toner, M. et al., "Blood-On-A-Chip," Annual Review of Biomedical Engineering, vol. 7, 2005, pp. 77-103.
Torr, G.R., "The Acoustic Radiation Force," American Journal of Physics, vol. 52, No. 5, 1984, pp. 402-408.
Trahey, G.E. et al., "Synthetic Receive Aperture Imaging with Phase Correction for Motion and for Tissue Inhomogeneities—Part II: Effects of and Correction for Motion," IEEE Transactions on Ultrasonics, Ferroelectrics, and Frequency Control, vol. 39, No. 4, 1992, pp. 496-501.
Traverso, C.I. et al., "Prospective assessment of the risk of deep vein thrombosis in elective abdominal surgery. Predictive role of Thromboelastography," Thrombotics and Haemorrhagic Disorders, vol. 7, No. 1, 1993, pp. 9-15.
Vig, S. et al., "Thromboelastography: a reliable test?," Blood Coagulation and Fibrinolysis, vol. 12, 2001, pp. 555-561.
Viola, F. et al., "A Comparison Between Spline-Based and Phase-Domain Time-Delay Estimators," IEEE Transactions on Ultrasonics, Ferroelectrics, and Frequency Control, vol. 53, No. 3, 2006, pp. 515-517.
Viola, F. et al., "A Comparison of the Performance of Time-Delay Estimators in Medical Ultrasound," IEEE Transactions on Ultrasonics, Ferroelectrics, and Frequency Control, vol. 50, No. 4, 2003, pp. 392-401.
Viola, F. et al., "A Novel Ultrasound-Based Method to Evaluate Hemostatic Function of Whole Blood," Clinica Chimica Acta, vol. 411, Nos. 1-2, 2010, pp. 106-113.
Viola, F. et al., "A Spline-Based Algorithm for Continuous Time-Delay Estimation Using Sampled Data," IEEE Transactions on Ultrasonics, Ferroelectrics, and Frequency Control, vol. 52, No. 1, 2005, pp. 80-93.
Viola, F. et al., "Analysis of Clot Formation with Acoustic Radiation Force," SPIE Proceedings, vol. 4687, 2002, pp. 235-242.
Viola, F. et al., "Comparison of Time Delay Estimators in Medical Ultrasound," IEEE Ultrasonics Symposium, vol. 2, 2001, pp. 1485-1488.
Viola, F. et al., "Efficient and Accurate Spline-Based Time Delay Estimation," IEEE Ultrasonics Symposium, vol. 2, 2004, pp. 870-873.
Viola, F. et al., "Imaging Viscoelastic Properties of the Vitreous," IEEE Ultrasonics Symposium, vol. 2, 2001, pp. 1623-1626.
Viola, F. et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, F. et al., "Sonorheometry: A new Method for Assessing Coagulation Potential," IEEE Ultrasonics Symposium, vol. 1, 2007, pp. 1001-1004.
Viola, F. et al., "Sonorheometry: A Noncontact Method for the Dynamic Assessment of Thrombosis," Annals of Biomedical Engineering, vol. 32, No. 5, 2004, pp. 696-705.
Viola, F. et al., "Ultrasound Echo Decorrelation Due to Acoustic Radiation Force," Proceedings of the IEEE Ultrasonics Symposium, vol. 2, 2002, pp. 1903-1906.
Voleišis, A. et al., "Ultrasonic method for the whole blood coagulation analysis," Ultrasonics, vol. 40, 2002, pp. 101-107.
Walker, W.F. et al., "A Fundamental Limit on Delay Estimation Using Partially Correlated Speckle Signals," IEEE Transactions on Ultrasonics, Ferroelectrics, and Frequency Control, vol. 42, No. 2, 1995, pp. 301-308.
Walker, W.F. et al., "A Fundamental Limit on the Accuracy of Speckle Signal Alignment," Proceedings of the IEEE Ultrasonics Symposium, vol. 3, 1994, pp. 1787-1791.
Walker, W.F. et al., "A method of imagining viscoelastic parameters with acoustic radiation force," Physics in Medicine and Biology, vol. 45, No. 6, 2000, pp. 1437-1447.
Walker, W.F. et al., "Application of Acoustic Radiation Force in Ophthalmic Ultrasound," Proceedings of the IEEE Ultrasonic Symposium, vol. 2, 1997, pp. 1291-1295.
Walker, W.F. et al., "Real-Time Imaging of Tissue Vibration Using a Two-Dimensional Speckle Tracking System," IEEE Ultrasonic Symposium, 1993, pp. 873-877.
Walker, W.F., "The Significance of Correlation in Ultrasound Signal Processing," SPIE Proceedings, vol. 4325, 2001, pp. 159-171.
Webster, "Medical Instrumentation: Application and Design," New York: John Wiley & Sons, 1998, 6 pages.
Westbrook, A.J. et al., "Protocol Based on Thromboelastograph (TEG) Out-Performs Physician Preference Using Laboratory Coagulation Tests to Guide Blood Replacement During and After Cardiac Surgery: A Pilot Study," Heart, Lung and Circulation, vol. 18, No. 4, 2009, pp. 277-288.
Whitten, C.W. et al., "Thromboelastography: Past, Present, and Future," Anesthesiology, vol. 92, No. 5, 2000, pp. 1223-1225.
Yu, A.C.H. et al., "Single-Ensemble-Based Eigen-Processing Methods for Color Flow Imaging—Part II. The Matrix Pencil Estimator," IEEE Transactions on Ultrasonics, Ferroelectrics, and Frequency Controls, vol. 55, No. 3, 2008, pp. 573-587.
Zieliński, T.P. et al., "Frequency and Damping Estimation Methods—An Overview," Metrology and Measurement Systems, vol. 18, No. 4, 2011, pp. 505-528.
International Preliminary Report on Patentability and Written Opinion, dated Oct. 8, 2013, in connection with International Application No. PCT/US2012/025270.
International Search Report, dated Sep. 30, 2013, in connection with International Application No. PCT/US2012/025270.
International Preliminary Report on Patentability and Written Opinion, dated Aug. 27, 2013, in connection with International Application No. PCT/US2012/025278.
International Search Report, dated Aug. 20, 2013, in connection with International Application No. PCT/US2012/025278.
International Preliminary Report on Patentability and Written Opinion, dated Oct. 9, 2012, in connection with International Application No. PCT/US2011/031832.
International Search Report, dated Dec. 15, 2011, in connection with International Application No. PCT/US2011/031832.
International Preliminary Report on Patentability and Written Opinion, dated Nov. 19, 2013, in connection with International Application No. PCT/US2012/038553.
International Search Report, dated Jan. 2, 2013, in connection with International Application No. PCT/US2012/038553.
International Preliminary Report on Patentability and Written Opinion, dated Mar. 20, 2012, in connection with International Application No. PCT/US2010/049342.
International Search Report, dated Nov. 16, 2010, in connection with International Application No. PCT/US2010/049342.
International Search Report and Written Opinion mailed Jun. 27, 2016 for Application No. PCT/US2016/022844.

* cited by examiner

DETERMINING MECHANICAL PROPERTIES VIA ULTRASOUND-INDUCED RESONANCE

BACKGROUND

Hemostasis is the physiological process that stops bleeding. Functional hemostasis requires the balanced engagement of plasma coagulation factors to initiate clotting, adequate fibrinogen to form the fibrin mesh, platelets to modulate factor function and to mechanically stiffen the fibrin mesh, and fibrinolytic enzymes to dissolve the clot when its useful life is over. Perturbation of any of these subsystems can disrupt hemostasis; either by impeding the cessation bleeding or by initiating clotting when it is unneeded. Disruptions of hemostasis contribute significantly to morbidity and mortality in patients suffering from heart disease, stroke, traumatic injury, cancer, and sepsis.

While hemostatic dysfunction impacts a broad range of medical conditions, it has been studied with particular intensity in cardiac surgery. Cardiac bypass surgery is associated with significant post-operative bleeding. This is caused by a combination of platelet damage by the bypass pump, factor and fibrinogen consumption associated with surgical trauma, and the occasional presence of residual anti-coagulant. A number of strategies are currently used to manage this dysfunction. The crudest strategy is a "shotgun therapy" approach; transfusing varying combinations of fresh frozen plasma, cryoprecipitate or fibrinogen concentrate, and platelet concentrate. This approach is often successful in controlling bleeding, however unnecessary transfusion carries a significant financial cost and increases patient morbidity and mortality. Recognition of the risks associated with excessive transfusion have led to increasingly specific and detailed guidelines to manage transfusion. These guidelines call for transfusion to be guided by point-of-care tests that assess hemostatic function in a timely and accurate manner.

A broad range of approaches have been proposed to fill the need for point-of-care hemostasis testing. These technologies can be separated into broad categories: clot-time assays, platelet-only tests, and viscoelastic tests. Clot-time assays can be implemented in simple systems, however a rapidly forming clot may not be a physiologically useful clot, so clot-time results may have limited clinical value. Moreover, clot-time assays generally operate on plasma, rather than whole blood, and therefore typically neglect the important interactions between plasma coagulation factors and platelets. Platelet-only tests provide useful information, but are also limited in that they neglect interactions between platelets and plasma coagulation factors. Viscoelastic tests have been shown to provide highly useful data. However, their operational complexity has traditionally limited their point-of-care utility. None of the currently available point-of-care tests adequately assess hemostatic function in a timely and accurate manner. A fast, accurate test is therefore still needed to fill this gap.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

SUMMARY

A device for estimating a mechanical property of a sample is disclosed herein. The device may include a chamber configured to hold the sample; a transmitter configured to transmit a plurality of waveforms, including at least one forcing waveform; and a transducer assembly operatively connected to the transmitter and configured to transform the transmit waveforms into ultrasound waveforms. The transducer assembly can also transmit and receive ultrasound waveforms into and out of the chamber, as well as transform at least two received ultrasound waveforms into received electrical waveforms. The device also includes a data processor that can receive the received electrical waveforms; estimate a difference in the received electrical waveforms that results at least partially from movement of the sample; and estimate a mechanical property of the sample by comparing at least one feature of the estimated difference to at least one predicted feature, wherein the at least one predicted feature is based on a model of an effect of the chamber wall. Finally, the device can also include a controller configured to control the timing of the ultrasound transmitter and data processor.

In one implementation, the at least one predicted feature predicted by the data processor is based on a model of an aspect of the induced movement that is caused at least in part by a boundary effect of the chamber wall.

In another implementation, the at least one predicted feature predicted by the data processor is based on a model of an aspect of the induced movement that is caused at least in part by resonance within the chamber.

In yet another implementation, the at least one predicted feature predicted by the data processor is based on a model of an aspect of the induced movement that is caused at least in part by reflection of an induced shear wave from the chamber wall.

Also disclosed is a device for estimating a mechanical property of a sample. The device may include a chamber configured to hold the sample; a transmitter configured to transmit a plurality of waveforms, including at least one forcing waveform; and a transducer assembly operatively connected to the transmitter and configured to transform the transmit waveforms into ultrasound waveforms. The transducer assembly can also transmit and receive ultrasound waveforms into and out of the chamber, as well as transform at least two received ultrasound waveforms into received electrical waveforms. The device also includes a data processor that can receive the received electrical waveforms; estimate a difference in the received electrical waveforms that results at least partially from resonance of the sample; and characterize a mechanical property of the sample from at least one feature of the estimated difference. Finally, the device can also include a controller configured to control the timing of the ultrasound transmitter and data processor.

Additional embodiments, implementations, and/or examples are provided below as well.

BRIEF DESCRIPTION OF THE DRAWINGS

The following detailed description will be better understood when read in conjunction with the appended drawings, in which there is shown one or more of the multiple embodiments of the present disclosure. It should be understood, however, that the various embodiments of the present disclosure are not limited to the precise arrangements and instrumentalities shown in the drawings.

DETAILED DESCRIPTION

Assessing hemostatic function in a timely and accurate manner may be accomplished by measuring mechanical properties of a blood sample as it clots. For example, the shear modulus of a blood sample may be measured over time during the process of coagulation. Throughout this application, "shear modulus" is referred to as "modulus" interchangeably. The terms "stiff" and "stiffness" are likewise indicative of modulus.

In embodiments described in the current disclosure, a forcing ultrasound waveform is applied to a sample within a test chamber. This forcing waveform applies acoustic radiation force to the sample, thus inducing motion. This motion is impacted by the presence of the test chamber walls. Ultrasound sensing pulses are applied to the sample and differences in their echoes provide information about movement of the sample. Such differences may include phase changes or time shifts, either of which can be related to displacement. Finally, the features of these differences, such as the period of oscillation of sample motion, are compared to analytical or computational models to estimate mechanical properties of the sample.

Figure 1:
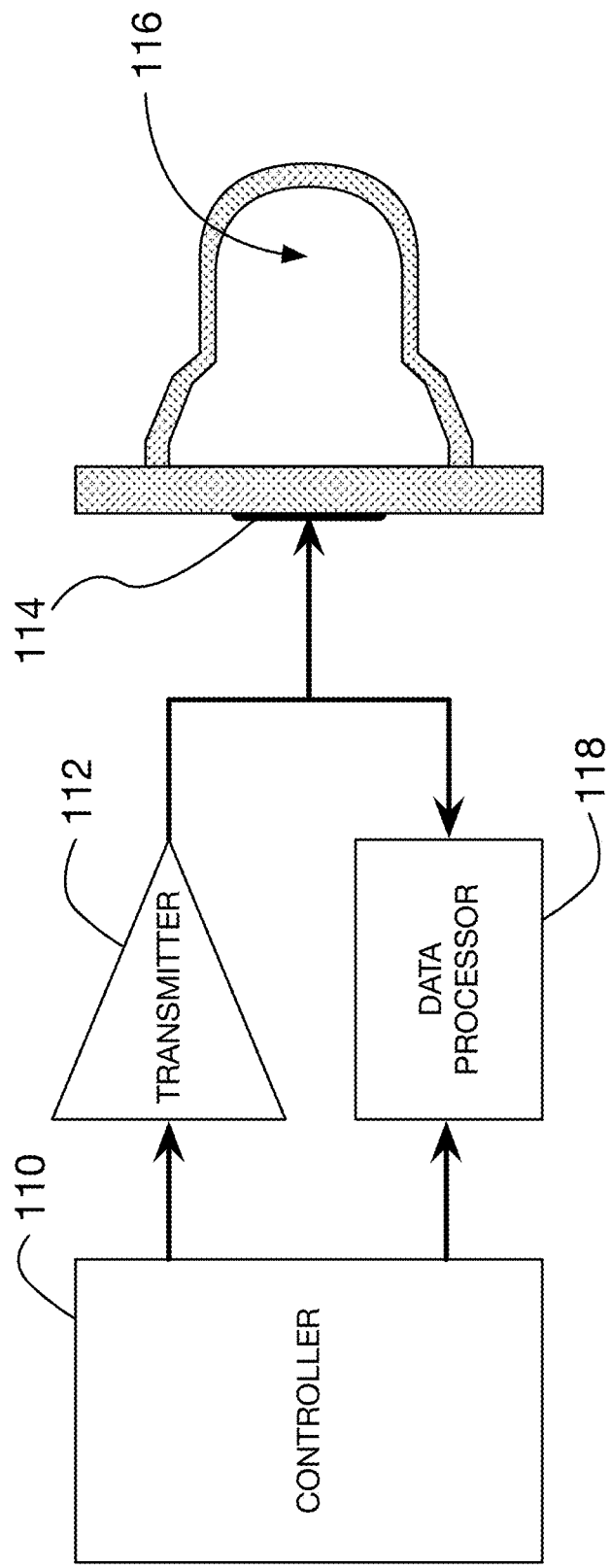
FIG. 1 is an example schematic of a device for measuring a mechanical property of a sample.

Embodiments described in this disclosure may comprise elements shown in FIG. 1. A transmitter 112 emits electrical waveforms including at least one forcing waveform. These electrical waveforms are converted by transducer assembly 114 into ultrasound waveforms. The forcing waveform induces sample motion within test chamber 116. Returned ultrasound echoes are converted to electrical waveforms by transducer assembly 114. These electrical waveforms are analyzed by data processor 118 to estimate sample mechanical properties. The details of implementation of this and other embodiments may be understood through the detailed description that follows. The timing of transmission, reception, and data processing are controlled by the controller 110.

The present disclosure makes use of the phenomena of ultrasound radiation force, which may sometimes be referred to as acoustic radiation force. Ultrasound radiation force is a body force that acts in the same direction as the direction of propagation of the ultrasound wave. It is the result of a transfer of momentum that occurs as the travelling ultrasound wave is absorbed or reflected. Ultrasound radiation force is localized to the ultrasound beam; with the force magnitude proportional to the intensity of the ultrasound beam. Thus a focused ultrasound beam may be used to apply a localized acoustic radiation force field. In the present disclosure the applied radiation force field is generally smaller than the test chamber to which it is applied. The sample motion induced by the radiation force field will initially be localized to the region of the force field. Over time however the displacement field will propagate outward from the region of force application.

In embodiments described in the current disclosure, ultrasound radiation force is used to generate a shear wave within a blood sample. A shear wave is a mechanical wave in which the direction of particle displacement is perpendicular to the direction of wave motion. The shear wave of the present disclosure may be generated by directing an ultrasonic waveform of sufficient magnitude into the sample via a "forcing waveform." The forcing waveform carries sufficient energy so that its absorption and reflection within the test sample generates acoustic radiation force. Acoustic radiation force is induced along the direction of ultrasound wave propagation and can be considered a body force acting upon some volume of the medium constrained by the dimensions of the ultrasound beam.

The induced shear wave will travel within the test chamber, reflecting from one or more of the walls. In some embodiments a single reflected shear wave may be detected and its arrival time at the ultrasound sensing beam may form the basis for estimating the modulus of the sample. For some combinations of chamber geometry and sample mechanical properties, it may not be possible to detect a reflected shear wave. For example the viscosity of the sample may be so high that the shear wave, while generated, has no easily discernable features and therefore no shear wave reflection from the wall can be readily measured. Nonetheless the sample motion resulting from acoustic radiation force will exhibit disturbances that result from the interaction of an induced shear wave with the chamber wall. The characteristics of this sample motion may form the basis for estimating the mechanical properties of the sample, even when the shear wave itself is not clearly resolved in the induced sample motion. In yet other cases the shear wave may reflect repeatedly within the chamber, generating a resonance that can form the basis for estimating the modulus of the sample.

Throughout this specification the terms test chamber, resonant chamber, resonance chamber, and chamber are used interchangeably with no loss in generality.

In the present disclosure the terms forcing waveform and forcing pulse will be used interchangeably with no loss in generality. Likewise the terms sensing pulse and sensing waveform will be used interchangeably with no loss in generality.

The motion of the induced shear wave, including its perturbations associated with reflections and/or reverberation, can be estimated by considering differences in the echoes from sensing waveforms. Said differences are not intended to imply a subtraction; instead, the term is used in a broad sense to mean any aspects that are not identical between waveforms. The term sensing waveform is used here to indicate an ultrasound waveform which has a magnitude too small to generate significant acoustic radiation force, and therefore too small to induce significant shear waves, but large enough to return ultrasound echoes for difference analysis. In an alternative embodiment the same waveform(s) may be used for forcing and sensing.

Shear modulus can be related to other measures of mechanical properties such as Young's modulus and Lame constants. Thus while the present disclosure is focused on the measurement of shear modulus, these estimates can be transformed to provide estimates of other mechanical properties.

In one embodiment, a device is provided for emitting a forcing waveform and a plurality of sensing waveforms into a sample within a resonant chamber, and processing echoes returned from the sensing waveforms. The device discerns mechanical characteristics of the sample from the characteristics of the resonance. For example, such a device may include at least a controller, a transmitter, a transducer assembly, a resonant chamber, and a data processor.

FIG. 1 shows a high-level block diagram of an example embodiment of the present disclosure. In this embodiment, a controller 110 is provided to manage the timing of various aspects of the testing procedure. For example, controller 110 may control the timing of transmission data digitization and data processing. Controller 110 may be a general purpose computer. In other embodiments, controller 110 may be a dedicated controller such as, for example, a field programmable gate array (FPGA). In one particular embodiment, a Xilinx Spartan 6 FPGA may be utilized. Alternatively an embedded processor or DSP chip might be used as the controller.

Controller 110 may control the timing of, among other things, a transmitter 112. Transmitter 112 may be used to transmit voltage waveforms. The controller 110 can direct the transmitter 112 to connect and disconnect from power supplies to the transducer assembly at specific time intervals. In one example embodiment, the transmitter 112 may transmit desired waveforms comprising positive, negative, and/or neutral voltages with specific time intervals for the transmissions between voltage levels. In other embodiments the transmitter may be capable of multiple voltage amplitude levels, enabling generation of a broader range of waveform shapes. In one embodiment, transmitter 112 comprises a Supertex MD1810 level shifter to control Supertex TC6320 MOSFETs to switch+/−100V supplies, and Supertex TC2320 to clamp transmit waveforms to ground. Various hardware devices, firmware, and/or software, or combinations thereof, may be used as well. The input signals to transmitter 112 may originate from the controller 110.

In the embodiment of FIG. 1, transmitter 112 transmits voltage waveforms to the transducer assembly 114. In this embodiment, the transducer assembly 114 is an ultrasound transducer. The transducer assembly 114 can convert transmit voltage waveforms into ultrasound waveforms and converts ultrasound echoes into receive voltage waveforms. In one example embodiment, the ultrasound transducer is a single-element composite piston transducer. However, other types of ultrasound transducers may be used, and may include hardware, firmware, and/or software, or combinations thereof. In alternative implementations the transducer may include a piezoelectric material (including single crystal materials), CMUT (capacitive micro-machined ultrasound transducer), a relaxor-ferroelectric transducer, thermoacoustic sources, or voice coils, other transducer technologies. In another alternative embodiment ultrasound transmission is performed using a thermoacoustic method where rapid heating causes thermal expansion that in turn generates an ultrasound wave. Transducer assembly 114 may further comprise an active transducer element—for example, a piezoelectric material—mounted to a single acoustic matching layer, which in turn may be mounted to a polymeric standoff. In one embodiment the transducer is air backed to enhance electro-mechanical efficiency. In one example embodiment, the transducer element of transducer assembly 114 is broad bandwidth and has sensitivity between approximately 5 and 12 MHz. In some embodiments, a series matching inductor is placed between the transducer assembly 114 and the transmitter 112 to tune out an imaginary component of the electrical impedance of the transducer. Other electrical circuits may prove advantageous for matching the electrical impedance of the transmitter, transducer, and receiver.

In an example embodiment, a test sample is placed within chamber 116 for testing. The transducer assembly 114 directs ultrasound energy through the test sample held within chamber 116. In some embodiments, chamber 116 is axisymmetric and has a major axis that is co-linear with the propagation vector of the ultrasound beam. In an alternative embodiment only a portion of the chamber 116 is axisymmetric, while other portions have arbitrary geometries as needed to support filling of the sample and to avoid blocking the ultrasound beam.

In some embodiments chamber 116 is fabricated from a material that is substantially stiffer (higher in shear modulus) than the material being characterized. Thus a resonant chamber fabricated of polystyrene, or similarly rigid material, can be effectively considered infinitely rigid for the purposes of analyzing blood clots. For example, chamber 116 may be several thousand, several hundred thousand, or even over a million times stiffer than the sample within chamber 116. For example, blood clots typically have a shear modulus of a few kiloPascals. Thermoplastics such as polystyrene have a shear modulus of roughly one gigaPascal.

In some embodiments, a "forcing waveform" and a "sensing waveform" may be directed into the test sample in chamber 116. The forcing waveform may be an ultrasonic waveform capable of inducing shear waves in the sample via acoustic radiation force, while the sensing waveform may be a lower energy waveform used to sense various aspects of the sample at a given point in time. These waveforms and their uses are described in more detail below. The modulus of the sample can be estimated by analyzing the resonance of ultrasound-induced shear waves within chamber 116.

In some embodiments the data processor 118 incorporates a number of functions to enable analysis of received echoes. For example, data processor 118 may incorporate a receiver and a digitizer that together provide digital data to a general purpose processor for data analysis. In this embodiment the receiver of the data processor 118 receives and amplifies electrical signals corresponding to ultrasound echoes within chamber 116. The receiver would be operatively coupled to the transducer in this embodiment. The receiver may also include a protection circuit that prevents high-voltage waveforms from overwhelming the one or more amplifiers of the receiver. An example of such a protection circuit is the Supertex MD0100. In some embodiments the input to the protection circuit is tied to the transducer while the output of the protection circuit is coupled to a low-noise amplifier and then to a variable-gain amplifier. Filtering stages also may be interposed to eliminate out-of-band noise. For example, in one embodiment the Analog Devices AD8334 LNA/VGA combination is utilized to amplify the incoming signal.

In one embodiment the receiver may be operatively coupled to a digitizer. Specifically the output of the amplifier might form the input to a digitizer. The digitizer transforms an analog signal to a digital signal. In one example embodiment, a 12-bit analog-digital converter (ADC) such as the Analog Devices AD9238 is utilized.

In the example embodiment of FIG. 1, receive echo data may be stored in a memory within data processor 118. Such a memory could capture digital output from the digitizer. Data processor 118 may include an FPGA, a general purpose processor, a dedicated DSP processor, or some combination of these items. For example, data processor 118 may include an FPGA storage unit in which echo data is temporarily buffered before it is transferred to an embedded processor. In that case the data is again buffered in the embedded processor before being transferred to an embedded PC for processing and modulus estimation. In an example embodiment, the data processor 118 estimates modulus through two distinct and interconnected steps. First, data processor 118 analyzes incoming echo signals to determine the displacement between the echoes returned from various sensing waveforms. In the second step the data processor 118 compares features of the measured displacements to the predicted features of either analytical or computer model predictions for the given chamber 116 geometry to estimate the modulus of the sample within the chamber 116.

Figure 2:
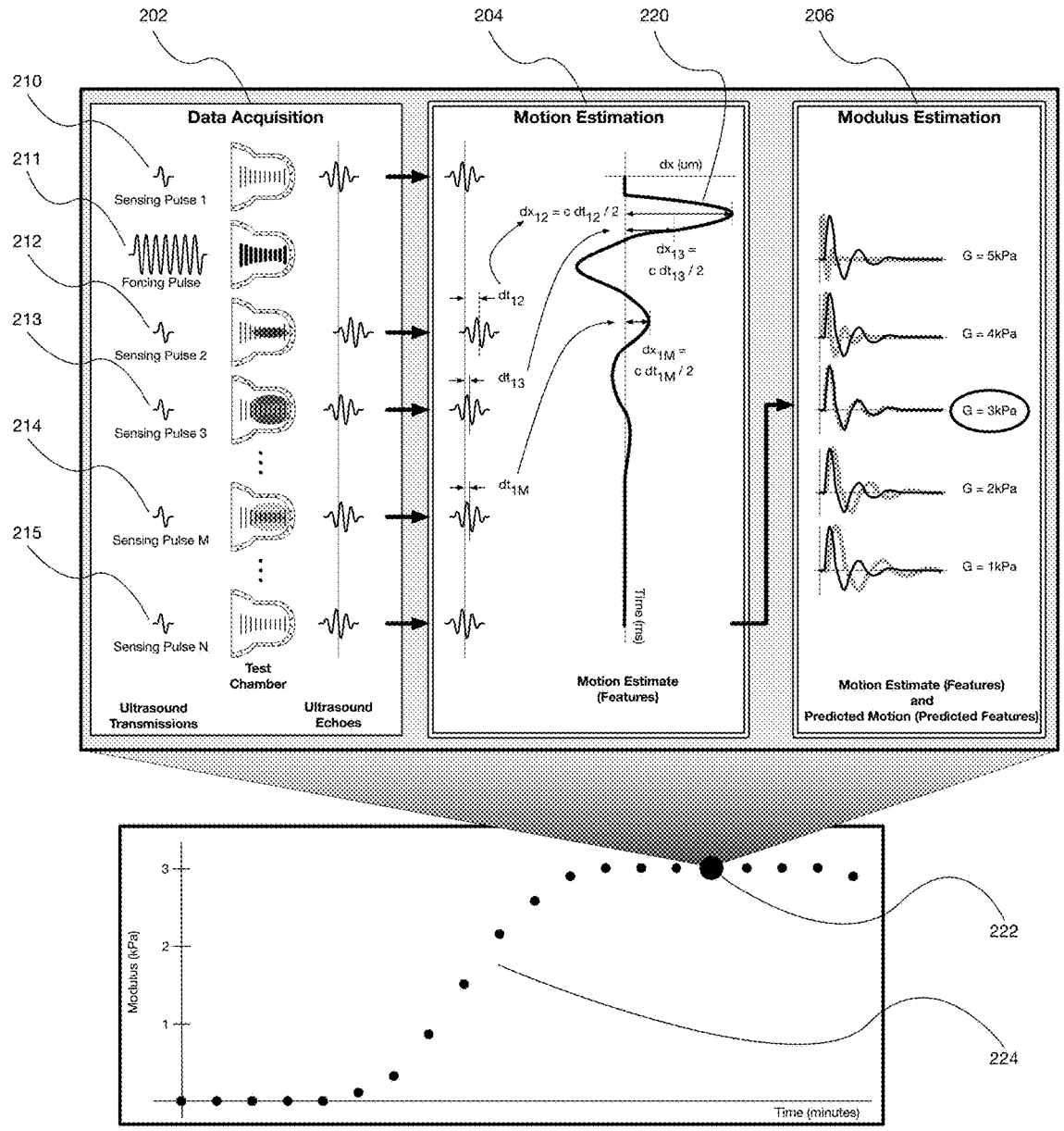
FIG. 2 is an example schematic of the signal processing and data acquisition process using the implementation of FIG. 1.

FIG. 2 depicts an example of an estimation process, including a data acquisition step 202, a motion estimation step 204, and a modulus estimation step 206. FIG. 2 also shows a plot 224 of modulus over time, including data point 222, the estimation of which is represented in more detail in panels 202, 204, and 206. The data acquisition panel 202 shows the data acquisition process. A series of ultrasound transmission are transmitted into the test chamber. The series of ultrasound waveforms are: (1) sensing pulse 210, (2) forcing pulse 211, (3) sensing pulse 212, (4) sensing pulse 213, (5) sensing pulse 214, and (6) sensing pulse 215. These waveforms are merely examples and the disclosure is not limited to the particular number or order of waveforms shown.

In some example embodiments, the sensing pulses are designed to impart minimal acoustic radiation force on the sample while returning echoes with high signal-to-noise ratio and bandwidth. Sensing pulse 210 may be used to establish a baseline echo for the sample before application of a forcing waveform. The forcing pulse 211, on the other hand, is designed to impart a substantial acoustic radiation force field. Following forcing pulse 211, a series of low intensity sensing pulses (212-215) are transmitted into the sample. The timing between the various sensing pulses is controlled to maintain precision in downstream signal processing steps.

In an alternate embodiment all of the waveforms are of sufficient energy to impart acoustic radiation force. In this particular embodiment these forcing waveforms also act effectively as sensing waveforms. The received echoes from any or all of these waveforms may be processed to estimate modulus using the methods and devices of the present disclosure. The present disclosure is further anticipated to incorporate arbitrary combinations of forcing waveforms, sensing waveforms, and combined use forcing/sensing waveforms.

Undisturbed coagulation of a healthy blood sample leads to the formation of a stiff clot. If however that same sample is mechanically stressed during coagulation then the forming fibrin mesh may be damaged, leading to a soft clot. Any measurement of mechanical properties during coagulation that applies significant mechanical thus has the potential to corrupt the evolution of the mechanical properties being measured. This biasing effect of viscoelastic clot measurement is particularly likely to corrupt the measurement of soft clots formed from the blood of patients with dysfunctional hemostasis. This problem has been previously addressed by the adaptive force measurement method disclosed in Patent Application PCT/US2010/049342. This application discloses a coagulation measurement system wherein the magnitude of the applied force is adjusted to constrain the magnitude of the induced displacement. In times where the clot is soft, the applied force is reduced to avoid damaging the clot. In times where the clot is stiff, the applied force is increased to maximize the sensitivity of the mechanical property estimation. This adaptive force approach is equally applicable to the present disclosure and combination with it is anticipated.

In one example embodiment, sensing waveforms are transmitted at an interval of approximately 122 microseconds, providing a sampling frequency of about 8.2 kHz. Other interrogation frequencies may be used as well. Generally speaking, the interrogation of stiffer materials requires higher interrogation frequency because the shear wave resonance has a high frequency (assuming a constant resonant chamber geometry). More accurate results may be achieved in softer materials by using a lower interrogation frequency so as to minimize the accumulated radiation force from the sensing waveforms and so as to enable the acquisition of data over a longer period of time for a fixed data memory size. With respect to blood samples, suitable interrogation frequencies range from about 2 kHz to about 16 kHz, for example.

A grouping of a single forcing waveform and a plurality of sensing waveforms may be referred to as an "ensemble." In one embodiment, an ensemble comprises about 500 sensing waveforms. In other embodiments, however, the ensemble may comprise between about 16 and about 2048 sensing waveforms. Other ensemble sizes may be used for measuring materials having higher or lower stiffnesses. One ensemble is processed to yield a single modulus estimate.

In some embodiments, the acquisition time for a single ensemble is approximately 62 milliseconds. However, the acquisition time may be lower or higher. For example, accurate results may be obtained by using an acquisition time of approximately 20-30 milliseconds for a single ensemble. Even lower acquisition times, such as 10 milliseconds, for example, may be used as well. A longer ensemble time period enables accurate measurement of a broader range of moduli. In some embodiments, ensembles may be repeated at a rate of approximately 16 Hz to measure rapidly changing moduli. In other embodiments the physical process under examination (coagulation) is slow enough that ensembles may be repeated at a rate of only once every six seconds and still provide data that accurately reflects the changes in modulus.

In some embodiments it may be advantageous to limit the range of mechanical properties being considered in a given ensemble based upon previously measured mechanical properties for the same test chamber. During coagulation, for example, it is expected that the shear modulus will vary smoothly with time, assuming that measurements are made at a small enough time interval. If, for example, the modulus is 1.0 kPa in a given measurement, then it may be advantageous to limit the range of possible moduli in successive measurements to a range between 0.5 kPa and 2.0 kPa. Even in cases where the modulus range is not explicitly limited, it may be advantageous to smooth modulus estimates across time by either linear filtering (convolution with a filter kernel) or non-linear filtering methods such as median filtering or combinations of both.

Each of the transmitted waveforms travels from left to right along an hourglass beam shape as shown by the series of vertical lines within the test chambers of panel 202 of FIG. 2. The sample is at rest when interrogated by sensing waveform 210. The sample remains at rest when impacted by the forcing waveform 211 because of the inertia of the sample material. Immediately after the forcing waveform passes however, the acoustic radiation force imparted by the forcing waveform 211 causes the sample material along the beam to move in the direction of propagation of the forcing waveform 211. In the embodiment of FIG. 2, this motion is first visible when the sample is interrogated by sensing waveform 212. This movement is shown in the figure as a shaded region lying under the ultrasound beam.

As sensing waveform 213 is transmitted, the radiation-force-induced displacement is beginning to propagate outward from the acoustic beam towards the test chamber wall. This displacement propagates predominantly in the form of a shear wave. Over time, the shear wave reflects from the wall, travels back through the acoustic beam, and reflects from the wall again. This repeated reflection represents resonance of the shear wave within the test chamber. Reverberation eventually settles down as the viscous losses within the sample and other losses damp out the propagating shear wave. Note that for some combinations of modulus, viscosity, and resonant chamber velocity the induced shear wave may reach the chamber wall so quickly that an observer would not see it propagate. Rather it would seem that the entire contents chamber were oscillating in time. Although qualitatively different than a propagating shear wave, this standing wave pattern is nonetheless an example of resonance and is anticipated by the current disclosure. In yet other combinations of modulus, viscosity, and chamber geometry, the excited shear wave might be quite discrete in time and space, and the shear wave reflected from the wall is a waveform that is discrete in space and time. Measurement of modulus by examining the arrival times of such a distinct pulse is one possible embodiment of the present disclosure. In this embodiment the shear wave echo reflection arrival time is an aspect of the differences in the received waveforms that is compared to the same aspect (shear wave reflection arrival time) of the modeled differences.

In yet other implementations, the chamber 116 is so small relative to the shear wavelength that no true shear wave can be generated. In this case it can be said that resonance does not exist for this combination of modulus and chamber geometry. It is still true however that the induced displacement is impacted by the presence of the chamber wall. This boundary effect will act to alter the induced displacement, compared to what would be expected if the same force were applied to an infinite or semi-infinite medium. This variation may take the form of a change in the time dependent displacement from that predicted for a semi-infinite medium. This variation is an aspect of the estimated time-displacement that is caused at least in part by a boundary effect of the chamber wall. In such a case the time course of the induced displacement can be considered in combination with the chamber geometry to estimate the sample modulus. In one embodiment this modulus estimation is performed by comparing the measured displacements to those predicted by a series of computer models, as described in more detail below.

The presence or absence of resonance may be determined by analyzing the differences in received echoes in general or by analyzing estimated time-displacements specifically. In one embodiment the time-displacement curve is analyzed for the presence of a trough (negative peak displacement). If such trough is found then it may be concluded that resonance is occurring. Should no trough (negative peak) in time displacement be observed then it may be concluded that resonance is not present. This conclusion about the presence or absence of resonance may be represented as a parameter indicating the strength of resonance. In this simple example the parameter would hold a value of 1 when a time-displacement trough is detected and a value of 0 when no such trough is detected. This concept can be extended further by considering whether a displacement peak is detected in conjunction with a displacement trough, as this would indicate even stronger resonance. An alternative parameter indicating the strength of resonance would be the mean value of the time-displacement curve. When resonance is absent, the time-displacement curve will be primarily unipolar and will therefore have a high mean value. Alternatively, when resonance is strong, the time-displacement curve will exhibit a strong oscillation around zero and will therefore have a low mean value. An alternative parameter indicating strength of resonance is the ratio of the mean displacement to the peak displacement over the measurement ensemble. A high value of this parameter indicates weak resonance. Other parameters can be computed to indicate the strength of resonance.

Each of the sensing waveforms returns an echo from inhomogeneities (acoustic scatterers) within the sample. In the case of whole blood, these inhomogeneities are primarily red blood cells. The present disclosure can also be used to measure homogenous materials, such as blood plasma, by the addition of polystyrene microspheres, or other agents, which act as acoustic scatterers.

As acoustic scatterers move away from the ultrasound transducer, the acoustic path length between the transducer and the scatterers lengthens. Assuming that the speed of sound is constant, this causes the echoes to arrive at a later time when the targets are pushed farther away by the resonating shear waves. Likewise, the echoes will arrive earlier in cases where the scatterers have moved closer to the ultrasound transducer. These changes in echo arrival time are differences between these waveforms that are indicative of underlying movement of the sample. If the speed of ultrasound propagation (speed of sound c) is known in the sample, or can be measured, then the measured time delays can be related to the underlying physical displacement through the well known relation $dx = c\, dt/2$.

In the preceding expression dt is the measured time shift between echoes, c is the speed of sound (ultrasound, not shear waves) and dx is the estimated relative displacement. Note however that the present disclosure does not require knowledge of the speed of sound as the displacement characteristics used to estimate modulus do not necessarily include absolute displacements. In one embodiment of the present disclosure, phase shifts are measured between the various sensing waveform echoes. These phase shifts are differences in the received waveforms that result from the underlying movement of the sample. For a resonating sample these phase shifts will exhibit the feature of oscillation with a frequency related to the modulus of the sample. The observed feature (oscillation frequency) can be compared to a predicted feature (oscillation frequency predicted by theory) to estimate the modulus of the sample.

It is well known that the speed of sound in blood changes as it clots. This evolving speed of sound has little or no effect upon the current measurement, however, for at least two reasons. First, as stated above, many of the algorithms used to relate measured displacement to modulus do not need to know the true displacement; relative displacements are all that are needed. Second, the speed of sound change occurs over a matter of minutes, while the measurement ensembles described herein occur over a matter of milliseconds. Thus the slowly evolving speed of sound has an imperceptible impact on the time-delay estimates from any single ensemble.

The echo data from the ensemble is processed to find differences in the received waveforms that are indicative of motion of targets along the ultrasound beam. One process of analyzing these waveform differences is known as "motion estimation," a process shown conceptually in the motion estimation panel 204 of FIG. 2. Each echo produced by, for example, sensing pulses 212-215, is compared to the reference echo produced by sensing pulse 210 in order to find the time delay between them. By using a measured or assumed speed of sound, the time delays between various echoes can be converted to displacements. All of the displacement estimates from a single ensemble are combined to form a time-displacement curve 220, as shown vertically on the right of motion estimation panel 204. This time-displacement curve is a feature indicative of the modulus of the sample. Note that the example time-displacement curve depicts oscillations associated with shear-wave resonance and a decay of those oscillations associated with the chamber geometry and the intrinsic viscous damping of the medium.

The motion estimation algorithm used to calculate differences in the receive waveforms may be an algorithm known in the art. Example algorithms include those presented by Kasai (C. Kasai, K. Namekawa, A. Koyano, and R. Omoto, "Real-Time Two-Dimensional Blood Flow Imaging Using an Autocorrelation Technique" IEEE Trans. Sonics Ultras., vol. SU-32, pp. 458-464, 1985), Loupas (Loupas et al., "Experimental evaluation of velocity and power estimation for ultrasound blood flow imaging, by means of a two-dimensional autocorrelation approach", IEEE Trans Ultrason Ferroelect Freq Contr. 42:689-699, 1995), and Walker (U.S. Pat. No. 8,306,293).

Alternatively, waveform differences may be analyzed to estimate motion by finding the time-delay corresponding to the peak of the correlation function between different various received echo signals. Direct measurement of time delays can be extended to the measurement of the delay envelope of the waveform after demodulation. As another alternative, relative phase shifts between various received echo waveforms are differences representative of motion in the sample. These phase shifts can be computed digitally by comparing the complex Hilbert Transform of the waveforms associated with different transmissions. As yet another alternative, the receive waveforms can be sampled digitally at an interval approximately ¼ of a period apart so as to approximate In-phase and Quadrature (IQ) signals. This so-called Direct Sampled In-phase and Quadrature (DSIQ) sampling scheme has previously been used to simplify ultrasound beamformer design (US20070016022 A1) and can be applied to calculate waveform differences representative of motion in the present disclosure. In another embodiment the received ultrasound waveforms are processed via quadrature demodulation to yield a complex waveform with an angle between its real and imaginary components indicating the phase of the received signal. This phase is a difference indicative of motion of the sample.

Figure 3:
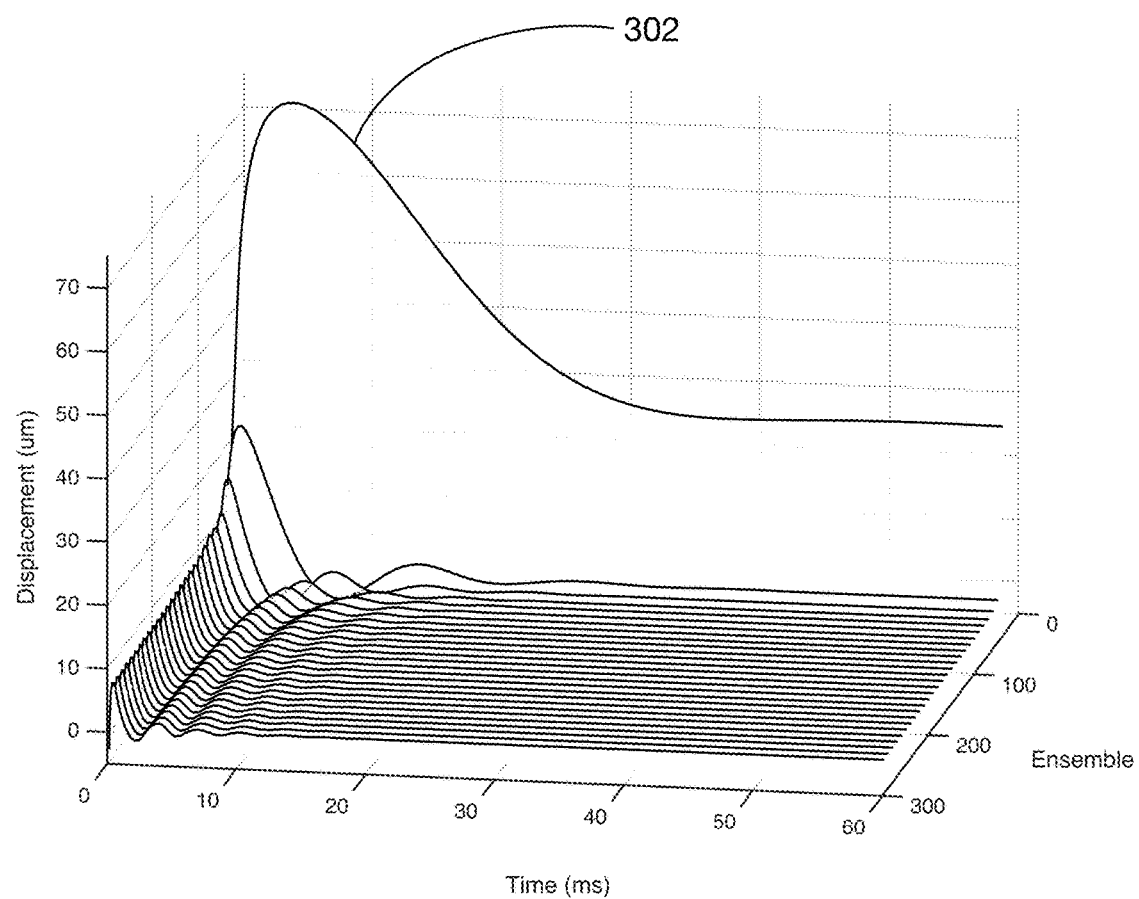
FIG. 3 shows representative experimental time-displacement curves from clotting human blood.

FIG. 3 shows experimental time-displacement curves obtained by the present disclosure. Waveform differences were analyzed to yield displacement estimates over a series of 300 ensembles. Each ensemble consisted of a single forcing waveform and 512 sensing waveforms transmitted at a pulse repetition frequency of 8,206 Hz. Larger displacements and lower frequency oscillations are seen earlier in the clotting process. The first time-displacement curve 302 shows no oscillation, while oscillations become clearer as the clot formed higher modulus. A simple algorithm based upon only the frequency of mechanical resonance would fail with the data of curve 302. This curve corresponds to a modulus for which this chamber geometry cannot support resonance. The present disclosure, however, can estimate the modulus even when no clear oscillation is visible, such as for time-displacement curve 302. Modulus in this case can be estimated by comparing the measured displacements (features) to computer or analytical models of the dynamic sample motion induced by the forcing waveform (predicted features).

The modulus estimation panel 206 of FIG. 2 depicts an example process of estimating the shear modulus of the sample from the experimentally determined time-displacement curve 220. The shape of time-displacement curve 220 is a feature of the estimated displacements that can, in turn, be described as waveform differences. In one example embodiment, a computer model has been used to generate a set of reference models, where each reference model is the predicted time-displacement curve for a given shear modulus and viscosity for the specific test-chamber geometry. These reference models incorporate predicted features associated with the modulus of the computer model. Such a computer model may make use of the Finite Difference Time Domain method, as described below. Alternatively finite element or boundary element computational models might be used. The processor searches through a library of reference models (predicted features) to find the one that most closely matches the experimentally measured time-displacement curve 220 (feature). In this embodiment the library of reference models can be formed offline using a Finite Difference Time-Domain (FDTD) model, as discussed below. Alternatively the reference models may be computed using a finite element or boundary element model. The reference models (predicted features) are shown in modulus estimation panel 206 as gray curves that each correspond to a different shear modulus. Each reference model of modulus estimation panel 206 shows the time-displacement curve 220 (features) overlaid in black. In this particular example embodiment, the reference model for 3 kPa shear modulus most closely matches the time-displacement curve 220. The modulus and viscosity used to form this reference model are the estimate of the modulus and viscosity of the sample. In other embodiments, the computer model calculates a range of models corresponding to potential modulus and viscosities for a given time-displacement curve immediately after the time-displacement curve is generated. However, this dynamic modeling approach may be excessively computationally burdensome relative to searching through predefined reference models. Improvements in computer power or reductions in algorithm complexity will enable dynamic computation of reference models. Such an approach would allow more precise estimation of modulus and/or viscosity. Such an approach could also be coupled with a coarsely sampled (in the modulus dimension) library of reference models to trade-off between computational complexity and storage requirements.

Note that the term "analytical model" may refer to a something as simple as an expression that relates resonant frequency to modulus, or as complex as a full time-displacement waveform predicted by an analytical expression. In cases where a full time-displacement waveform is used as a model it may be advantageous to evaluate that analytical expression and build a set of reference models, analogous to the approach described above for computational models.

In an alternative embodiment, no explicit reference curves are used to estimate modulus. Rather a feature of the time displacement curve, such as its period of oscillation, is computed and used with the period of oscillation predicted by an analytical model (predicted feature) to estimate the modulus. An example analytical model is derived below. That model shows that the resonant frequency (inverse of period) is related to the resonant chamber radius and material modulus and density through the following expression:

$$f = \frac{2.4048}{2\pi R} \frac{\sqrt{G}}{\sqrt{\rho}}$$

This expression can be rearranged so that the modulus can be estimated directly from the measured period:

$$G = \rho \left( \frac{2\pi R}{2.4048T} \right)^2$$

where T is the period of resonance. Thus the period of oscillation is a feature that can be compared to a predicated feature (the period of oscillation of an analytical model) to estimate modulus. Likewise, the period of oscillation is an aspect of induced movement that is caused at least in part by resonance within the chamber. Note that in the case of an analytical model it is not necessary to test a series of model predictions, rather the step of comparing predicted and experimental features can be accomplished through a simple mathematical expression. Such an approach is anticipated by the current disclosure. Alternatively resonant frequency could be used with the above expression to estimate modulus.

In some applications it may not be necessary to estimate a mechanical property. Rather, it may prove useful to instead characterize a mechanical property. In this context we intend the concept "estimating a mechanical property" to refer to making a quantified estimate of a well-known mechanical property such as shear modulus. Alternatively we consider the concept of "characterizing a mechanical property" to refer to determining something about the mechanical property, but not necessarily putting a unit on it or even determining it in a directly proportional way. For example, estimating the resonant frequency of a sample characterizes a mechanical property of that sample without taking the extra step of referencing to the true modulus. Rather than producing a graph of modulus versus time, it might be useful to produce a graph of "resonant frequency" versus time.

While "resonant frequency" is not identical to modulus, nor even proportional, tracking resonant frequency would allow one to obtain significant information about coagulation. We thus recognize the utility of such characterization without the need to connect it to a fundamental mechanical property such as shear modulus.

The period of resonance is a feature that can be used as a basis for estimating mechanical properties or characterizing mechanical properties. Given that period is simply the inverse of frequency, estimation of period is equivalent to estimation of frequency, and vice versa. The period of resonance can be estimated in a variety of ways from differences between received waveforms. For the purpose of this discussion we will restrict our consideration of differences between received waveforms to motion estimates made from received waveforms, although other approaches are envisioned particularly including phase changes estimated from the received waveforms. We begin by considering a time-displacement curve, like one of those depicted in FIG. 3. The period of oscillation of such a curve may be estimated by taking a Fast Fourier Transform (FFT) and estimating the frequency at which the energy is at its peak. Alternatively one could subtract the mean from the time-displacement curve and then utilize Burg's method for autoregressive power spectral density estimation. The frequency of peak energy corresponds to the frequency of oscillation. The ROOT-MUSIC algorithm can also be applied to estimate the frequency of oscillation. Other spectral estimation techniques could similarly be employed.

The frequency of oscillation may also be estimated through other means. Specific algorithms are known for estimating the frequency of a decaying sinusoid. One such algorithm is described in the paper "Parameter estimation of exponentially damped sinusoids using a higher order correlation-based approach," by D. P Ruiz et. al. and published in *IEEE Transactions on Signal Processing*, vo. 43, no. 11, November 1995. A review of algorithms dedicated to this problem is presented in the paper "Frequency and damping estimation methods—an overview" by T. P. Zieliński and K. Duda and published in *Metrology and Measurement Systems*, vol. 18, no. 4, 2011. Other approaches are also available.

The period of oscillation may be estimated directly from the time-displacement signal. In one approach, the time of the first trough in displacement (maximum negative displacement) is used as an estimate of ½ of the oscillation period. Since the time-displacement signal is discretely sampled in time but the period can take on continuous values, it is advantageous to apply interpolation. In one embodiment the time-displacement signal is directly interpolated to a higher sampling frequency prior to locating the time of the trough. Such interpolation may be performed by resampling via FFT, piecewise cubic spline interpolation, or other known methods. Alternatively the discrete sample at which the trough occurs can be identified and the true location of the trough found via an analytical interpolation scheme. In one embodiment a parabola is fit to the discrete trough value and its two nearest neighbors, and the time of minimum of that parabola is used as the estimated time of the trough. Higher order functions including piecewise cubic splines can alternatively be used for such interpolation.

The period of displacement oscillation may be estimated through other means as well. In an alternative approach the locations of the first trough and the second peak are determined and the time interval between them is the estimate of ½ of the oscillation frequency. Note that the use of the second peak is generally preferred as the timing of the first peak is distorted by the application of the forcing pulse. This peak-finding strategy can be extended further by estimating the locations of multiple positive and negative peaks and combining those locations to estimate the period. In one embodiment the first and second troughs, and the second and third peaks are identified. Consider the time of the first trough as $t_{n1}$, the time of the second peak as $t_{p2}$, the time of the second trough as $t_{n2}$, and the time of the third peak as as $t_{p3}$. In this case the period can be related to each of the peaks and troughs as follows:

$$t_{n1}=T/2+e_1$$

$$t_{p2}=T+e_2$$

$$t_{n2}=3T/2+e_3$$

$$t_{p3}=2T+e_4$$

where $e_1$, $e_2$, $e_3$, and $e_4$ represent error terms resulting from noise in the peak/trough location estimates. The period of oscillation may be measured directly from the estimated times of these peaks and troughs through the following expression:

$$\hat{T}=(2t_{n1}+t_{p2}+2/3t_{n2}+1/2t_{p3})/4$$

This expression has the advantage of reducing the weighting of later peaks and troughs that will have lower relative amplitude and therefore will be more susceptible to noise. Alternatively the period may be estimated from the same peak and trough times through the following expression:

$$\hat{T}=(t_{n2}-t_{n1}+t_{p3}-t_{p2})/2$$

The present disclosure anticipates other variants of this approach including more or fewer peaks and troughs and alternative expressions for estimating the period from the times of the peaks and troughs.

The period of oscillation may alternatively be estimated from locations of the zero-crossings of the time-displacement curves. While the peak to trough time interval is ½ period, the zero-crossing interval is approximately half as long at ¼ period. The above described methods of combining peak and trough times to estimate oscillation period may be readily modified to combine zero-crossing times to estimate oscillation period. Numerous algorithms for estimating the time of a zero crossing are known. One approach fits a line to the data points near the zero crossing and the finds the time at which the fit line equals zero. Higher order approaches using polynomials or splines are also envisioned.

In some embodiments, the shear-modulus estimate for each ensemble is plotted as a single point of a curve, as shown in FIG. 2. In this particular embodiment, the example calculations represented by panels 202, 204, and 206 result in data point 222. Repeated calculations, for a plurality of ensembles over a period of time, result in the shear-modulus curve 224.

Figure 4:
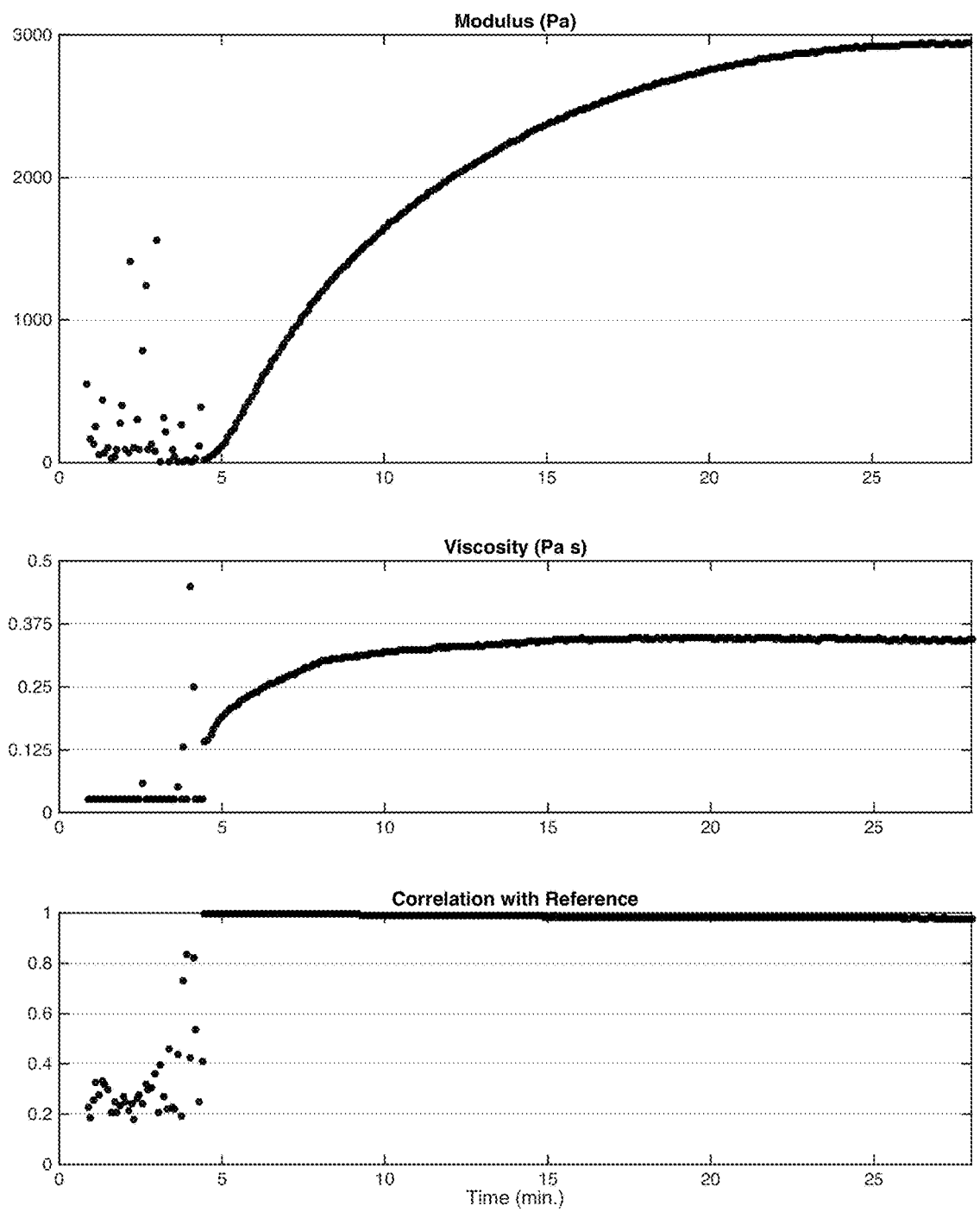
FIG. 4 shows representative time-modulus and time-viscosity curves estimated utilizing a computer model.

In one example embodiment, the similarity between reference models and the experimentally determined time-displacement curve 220 is quantified using a normalized correlation coefficient. A normalized correlation coefficient between two different signals a[n] and b[n] is given by the following equation:

$$\rho_{ab} = \frac{\sum_{i=1}^{N}(a[i]-\bar{a})(b[i]-\bar{b})}{\sqrt{\sum_{i=1}^{N}(a[i]-\bar{a})^2 \sum_{i=1}^{N}(b[i]-\bar{b})^2}}$$

where $\bar{a} = \frac{1}{N}\sum_{i=1}^{N} a[i]$ and $\bar{b} = \frac{1}{N}\sum_{i=1}^{N} b[i]$ FIG. 4 depicts the results of modulus estimation by the present disclosure as applied to clotting human blood. A small amount of kaolin was added to a sample of human whole blood. The top panel shows the modulus estimated over time, with the reagent (kaolin) added to the blood sample at time zero. The middle panel depicts the estimated viscosity over time. The lowest panel depicts the normalized correlation between the experimental time-displacement curves and those predicted by the Finite Difference Time Domain model described below. The model used for this figure considered moduli between 10 and 10,000 Pa and viscosities between 0.025 and 0.8 Pa s. A total of 16,032 combinations of modulus and viscosity were modeled. All models assumed a density of 1.06 g/cm$^3$. The geometry of our experimental test chamber was modeled on a spatial grid sampled at 100 um in each dimension. The resonant portion of the test chamber consisted of a cylindrical region 4.2 mm in diameter and approximately 1.5 mm in length with a hemispherical cap the same radius as the cylinder. The first 18 time-modulus estimates were removed from the experimental data and the models prior to computing the correlation between them. A best-fit line was removed from both the experimental time-displacements and computer model time-displacement predictions prior to computing the correlation. The erroneous modulus estimates in the early stages of clot formation occur because the model fails to allow for the low modulus of liquid blood or blood in the very earliest stages of clot formation.

The results shown in FIG. 4 are notable, in part, because of the relatively high correlation between the experimentally determined time-displacement curves and the predictions of the FDTD model. We see from the bottom panel of FIG. 4 that for a well formed clot the correlation between the FDTD model and the experimentally measured time-displacement curves is well over 0.95. This provides a strong indication that the computation model is an appropriate one for these experimental conditions. The correlation between the model and the experimental data is much worse for the liquid blood phase. This is not surprising given that the softest model in that case corresponds to a modulus of 10 Pa, which is far from the liquid state, which has a modulus of zero. Similar correlation tests were performed with time-displacement waveforms formed by numerical evaluation of the analytical model derived below. Although not shown, these results also correlated well with experiment; confirming the utility of the analytical model. The correlations for the analytical model were somewhat worse that the FDTD model. This is likely because the analytical model assumes an infinitely long cylinder, while the FDTD assumes a capped cylinder like the real experimental test chamber.

Figure 5:
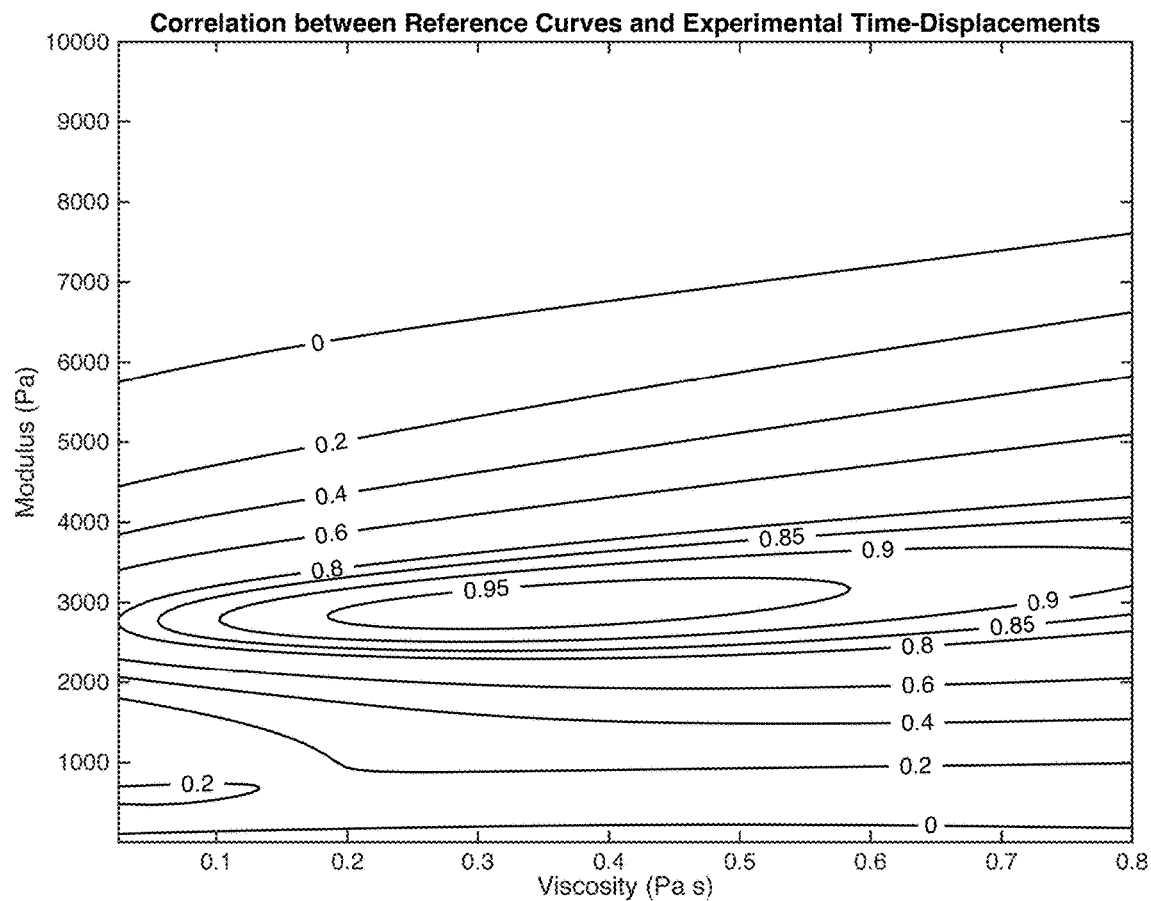
FIG. 5 shows an example contour plot of correlations between experimental time-displacement data and computer models across a range of moduli and viscosities.

The correlation between an experimental time-displacement curve and a range of reference models can be plotted as a two-dimensional function of modulus and viscosity, as shown in the contour plot of FIG. 5. This figure depicts the normalized correlation between the experimental time-displacement curves and those predicted by the Finite Difference Time Domain computational model described below. The model used for this figure considered moduli between 10 and 10,000 Pa and viscosities between 0.025 and 0.8 Pa s. A best-fit line was removed from both the experimental time-displacements and computer model time-displacement predictions prior to computing the correlation. The peak correlation lies within the smallest ellipse labeled 0.95 in this figure. The location of the peak corresponds to the estimated modulus and viscosity for a particular example ensemble. The smallest ellipse (highest correlation) is oblong, spread across a large range of viscosities and smaller range of moduli. Small amounts of noise may cause successive estimates to wander around the peak correlation, although it will likely stay confined to the high correlation contour. The shape of the 0.95 correlation contour indicates that the estimates of viscosity may include significant variability, as evidenced by the breadth of the contour in the viscosity dimension. The variability of modulus estimates will be relatively smaller as a result of the narrower contour in this dimension. However, the correlation function is not separable in the viscosity and modulus dimensions. Rather, an error that shifts the viscosity must also shift the modulus. This observation suggests that, in cases where the viscosity can be assumed to hold a certain value, we can fix that parameter and obtain more precise and repeatable estimates of shear modulus. This approach of fixing the viscosity has the added bonus of limiting what was a two-dimensional search (modulus and viscosity) to a one-dimensional search (modulus), which improves computational efficiency.

Figure 6:
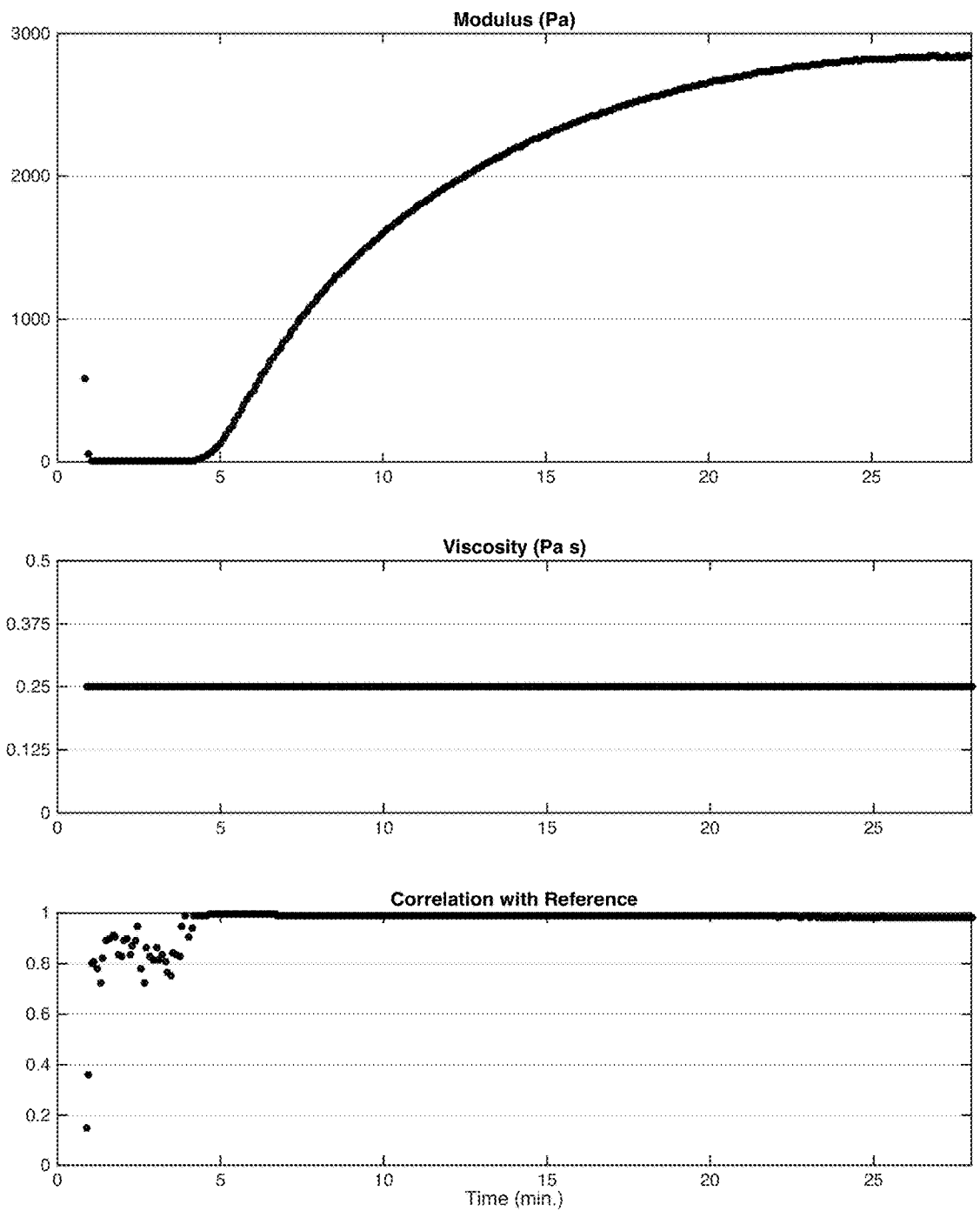
FIG. 6 shows a representative time-modulus curves estimated utilizing a computer model with the viscosity held constant.

FIG. 6 depicts the result of modulus estimation with the viscosity held constant. The top panel shows the modulus estimates. The middle panel shows the viscosity, which was fixed at a value of 0.25 Pa s. The bottom panel shows the correlation between the model and the experimental time-displacements. The model used for these estimates was in many ways identical to that used to obtain the results of FIG. 4. There were two notable differences. First, the modulus varied between 0.01 and 10,000 Pa. Second, the viscosity was held constant at a value of 0.25 Pa s. A total of 1,167 models were created. The results of FIG. 6 show a significant improvement in modulus estimates before a firm clot has formed. Although the correlations for these early estimates are fairly low, they are significantly higher than they were for FIG. 4. This result is encouraging as it shows that adjusting the range of the model to incorporate lower moduli yields a closer estimate of mechanical properties when the modulus of the sample is lower. This is another confirmation of the validity of the computational model. The results of FIG. 6 required less than $1/10^{th}$ the computation of the results in FIG. 4, with no loss in the quality of the result.

The computational and analytical models described in the present disclosure have a number of adjustable parameters that might be estimated or alternatively held constant, depending upon the specific sample and chamber geometry. In the preceding example it was show to be advantageous to hold the sample viscosity and density constant and evaluate the model for a range of shear moduli. In human blood it is reasonable to hold density at a constant value as the variation among individuals is quite low. While viscosity can vary somewhat more, the advantage of limiting that degree of freedom in estimation may outweigh any absolute error in viscosity. For different samples it may be advantageous to hold modulus constant while allowing either viscosity or density to vary. In yet other embodiments the chamber geometry may not be known precisely and models may allow variation of certain aspects of the chamber geometry among models.

In some embodiments, the value of the normalized correlation coefficient can be used to reject modulus and viscosity estimates that are unreliable and are unlikely to be correct. For example, the normalized correlation coefficient can be used to reject modulus and viscosity estimates where a bubble in the acoustic path corrupts the underlying ultrasound echoes. Processing this corrupted echo data will yield a time-displacement curve that is also excessively noisy. While a typical correlation between the best reference model and the experimental time-displacement curve may be 0.98, the correlation for the corrupted time-displacement data might fall to 0.40, for example. This significant reduction in correlation would clearly indicate that such a measurement is not reliable and should be rejected. This process of rejecting estimates with low correlation may be referred to as "masking" The appropriate threshold value can be determined empirically from experimental trials, however a reasonable threshold may be around 0.9.

The masking of shear-modulus estimates according to their peak correlation with the reference models is particularly valuable for cleaning up noisy estimates formed before the blood has begun to coagulate. For liquid blood, the time-displacement estimates show very large displacements that are often irregular. The irregular nature of these curves makes it possible for them to fit almost any reference model, although this fit is merely coincidence rather than an actual match. Moreover, the reference model may not actually be applicable until coagulation begins forming a solid "clot." For example a model based upon a viscoelastic solid is inappropriate for a liquid sample. In these cases, while there is a fit, the quality of match and therefore correlation coefficient is quite low. By simply removing modulus estimates for which the peak correlation is below a reasonable threshold, it is straightforward to remove erroneous modulus estimates associated with liquid blood.

Figure 7:
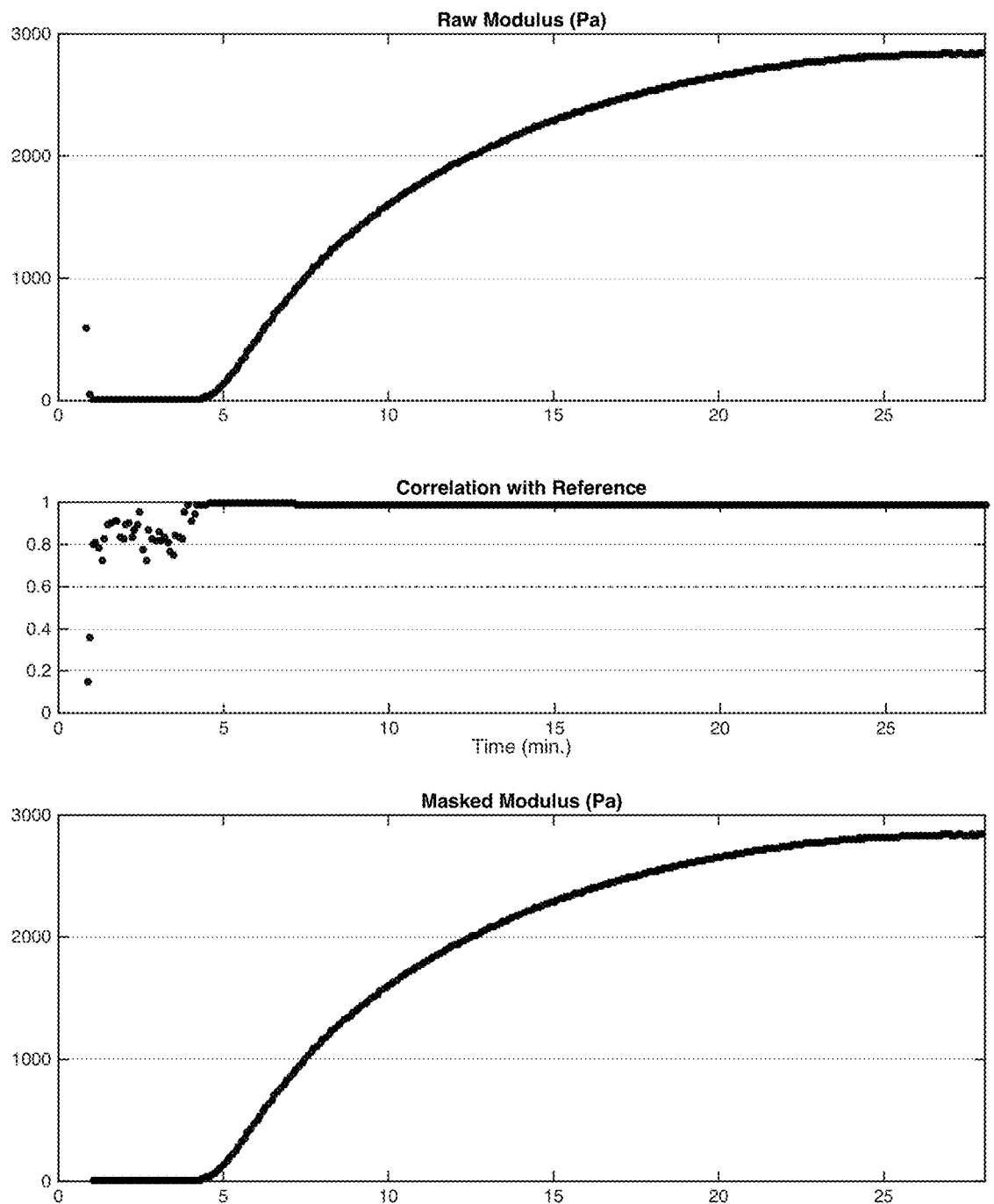
FIG. 7 shows an example of the use of correlation masking to remove outlying modulus estimates.

The concept of "correlation masking" was applied to the experimental results of FIG. 6, with the results shown in FIG. 7. The top panel shows the raw modulus estimates; including two data points at the beginning of the measurement. These data points are clearly in error. The central panel shows the correlation between the experimental data and the best-fit models. We select a correlation threshold of 0.6, which was selected to remove clearly erroneous data points. The lowest panel of FIG. 7 shows the remaining modulus estimates after the removal of the moduli with correlation below 0.6. The two erroneous modulus estimates have been eliminated.

The correlation between a model and experimental time-displacement estimates may also be used for other purposes. In one alternative embodiment, multiple different models are formed with variations in both mechanical properties and in underlying assumptions. For example, one family of models could be developed in which the sample is assumed to be a viscoelastic solid, while a second family of models assumes a liquid sample. Within each family the mechanical properties are allowed to vary. In this embodiment the data processor would test the correlation between each model in both of the two families against the estimated time-displacement curve. The specific model with the best correlation to the time-displacement curve would indicate both the value of the mechanical properties and the type of material that best describes the sample. In this specific example the material type would be either a viscoelastic solid or a liquid.

The library of reference models necessarily contains a finite number of reference models. In some embodiments, the modulus estimate may fall between reference models. This limitation can be overcome with little computational cost by interpolating the correlation coefficient around the measured peak to locate the shear modulus corresponding to the best correlation, whether a reference model was computed for that modulus or not. In the simplest case, where the viscosity is held constant and the modulus alone is allowed to vary, the modulus estimate can be determined by locating the peak of a parabola fit through the correlation of the best fit reference model and the correlations of its two nearest neighbors. Other interpolation schemes, including spline based and higher order polynomials, may yield even more precise results. Further, the interpolation described here can be applied to two-dimensional (modulus-viscosity) estimates by using a two-dimensional interpolation scheme. The experimental results presented here all made use of interpolation to form modulus estimates.

The experimentally determined time-displacement curve may be corrupted by a variety of physical and electronic effects. For a finite-volume test chamber, a forcing waveform may generate significant reverberant ultrasound echoes that may extend into the acquisition periods of the following sensing waveforms. In one example embodiment, the impact of such reverberation may be mitigated by designing the frequencies of the forcing waveform and the sensing waveform to lie within different frequency bands, and then using analog or digital filtering so suppress the reverberation associated with the forcing waveform. In an alternate embodiment, sensing waveforms sent shortly after a forcing waveform can be removed from the time-displacement estimation curve prior to searching the reference models for a best fit. This approach of rejecting erroneous time-displacement estimates can either be performed statically (e.g., the first 6 estimates from every time-displacement curve are assumed erroneous) or performed dynamically (e.g., a quality metric is computed to for the time-displacement estimates and estimates with a quality metric below a certain threshold are discarded).

Figure 16:
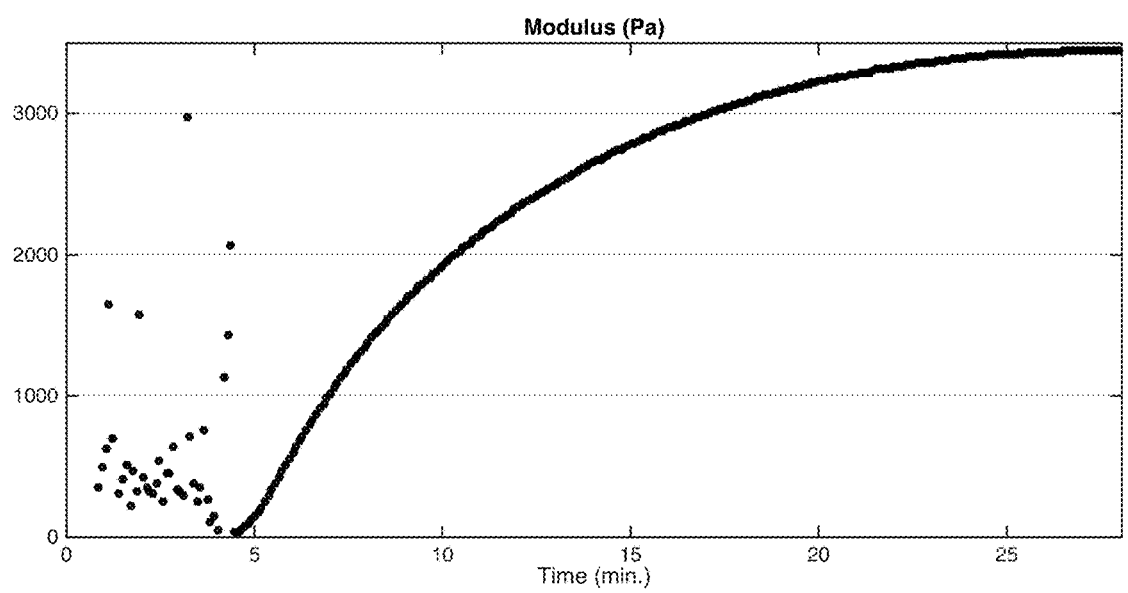
FIG. 16 shows a representative time-modulus curve estimated utilizing an analytical model.

FIG. 16 depicts an experimentally determined time-modulus curve using an analytical expression to relate the measured period of displacement oscillation to the shear modulus. This approach used equation 58 to relate resonant frequency to modulus. The period of resonance was estimated from the time difference between the first trough in displacement to the second peak of displacement. This approach yields a robust estimate of clot modulus, although it is challenged by the early liquid phase before coagulation begins. As described elsewhere in this disclosure, such erroneous estimates could be masked depending upon a parameter indicative of the strength of resonance. This analytical estimate of modulus is quantitatively different from the estimated based on the computational model. This is likely due to the different geometric assumptions of the two approaches. The analytical model assumes an infinitely long cylinder while the computational model assumes a capped cylinder like the experimental test chamber.

The present disclosure anticipates estimating mechanical properties based upon at least three different but interrelated modes of mechanical behavior. In the first mode a forcing pulse is applied to the chamber and has the potential to excite a mechanical resonance of the sample, which is bound by the test chamber. In one embodiment, the frequency of resonance is the basis for estimating the shear modulus of the sample. Note however that for some combinations of modulus, viscosity, density, and chamber geometry, it may not be possible to induce true resonance. For example, if the sample viscosity is high relative to the modulus then the system will be under-damped and no resonance will occur. As the clot stiffens, however, the modulus will increase while the viscosity remains relatively constant. Thus as the clot stiffens, an example device disclosed herein will be able to detect the initiation of resonance. Such a transition might offer a useful and simple indicator of clot formation.

In another embodiment, the viscosity of the sample is low enough relative to the modulus that a well-defined (in space and time) shear wave can be initiated within the sample. In cases where the shear wave is constrained in time and space its reflection from the chamber walls will be clear and easily detected from the differences between echoes received from scatterers within the sample. Knowledge of the chamber geometry (shear wave path length) enables direct estimation of shear wave velocity (and therefore modulus) from the arrival time of shear wave echoes from the chamber wall. As with the prior example of resonance, there are certain combinations of mechanical properties and geometries for which clearly measurable shear waves cannot be generated. As with the resonance example, a transition between states where clearly detectable shear waves cannot be generated to a state where they can be might offer a good proxy for the transition from liquid blood to a formed clot. The timing of such a transition might therefore present a useful measure of clot formation time.

In a third embodiment, neither clear resonance nor propagating shear waves are readily measured. That does not, however, preclude estimation of mechanical properties within the test chamber. For any sample within a finite chamber, the walls of the chamber will change the apparent mechanical impedance of the sample. In this context mechanical impedance describes the relationship between and applied force and the resultant displacement. A very soft sample within a very large test chamber will exhibit a mechanical impedance much like that sample would in an infinitely large test chamber. Alternatively, a stiff sample within a small test chamber will exhibit a mechanical impedance quite different from that observed in a larger test chamber. In the context of dynamic force application, the magnitude of the sample viscosity will further impact the perceived mechanical impedance. The present disclosure anticipates comparing models of the sample within test chamber to experimental measurements to estimate the mechanical properties of the sample. In this embodiment the impact of the wall (boundary effect) is explicitly considered. Since the impact of the boundary (wall) for a given chamber geometry varies depending upon the mechanical properties of the sample, a transformation from the boundary effect being insignificant to it being significant can be a proxy for the transition from a liquid blood sample to a formed clot.

Figure 8:
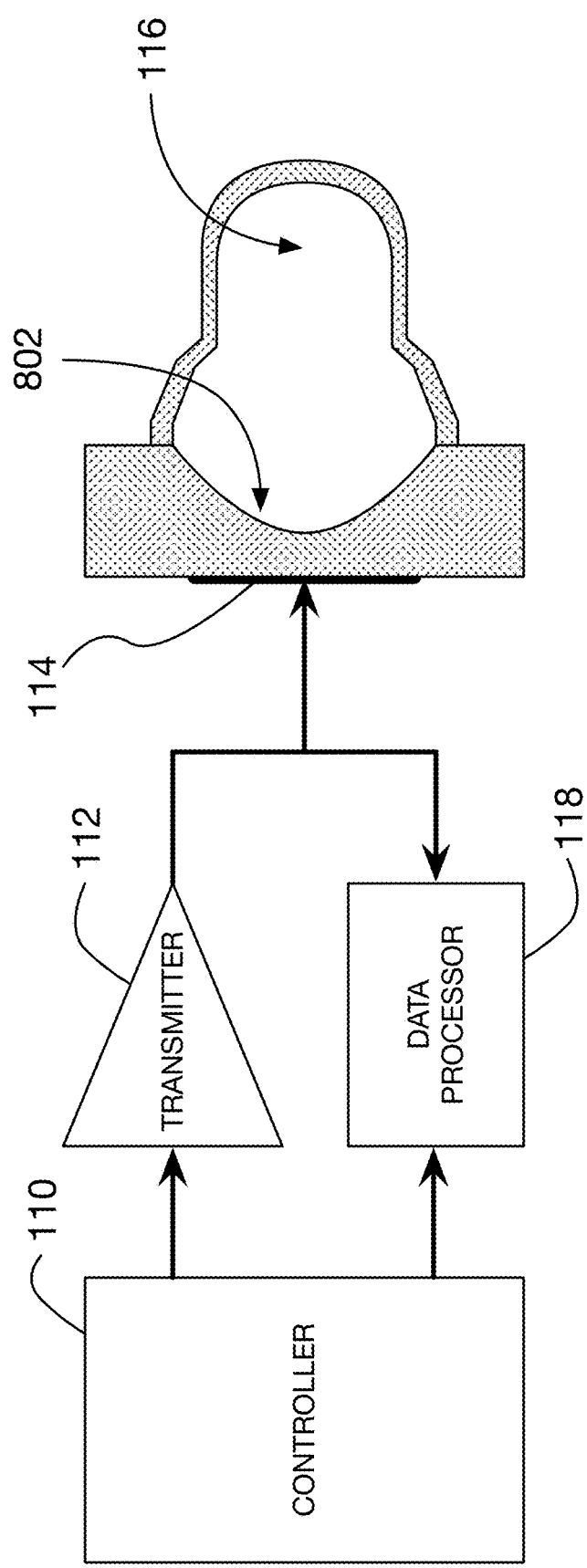
FIG. 8 depicts an example embodiment of the present disclosure wherein a focusing element is associated with the transducer assembly

In another embodiment, shown in FIG. 8, the transducer assembly 114 of FIG. 1 incorporates a focusing element 802. The addition of a focusing element increases the intensity of the applied forcing waveform and increases the strength of the received echoes. In addition the use of the focusing element 802 enables use of a larger transducer element within transducer assembly 114. The substitution of such a device is wholly contemplated herein by Applicant.

Figure 9:
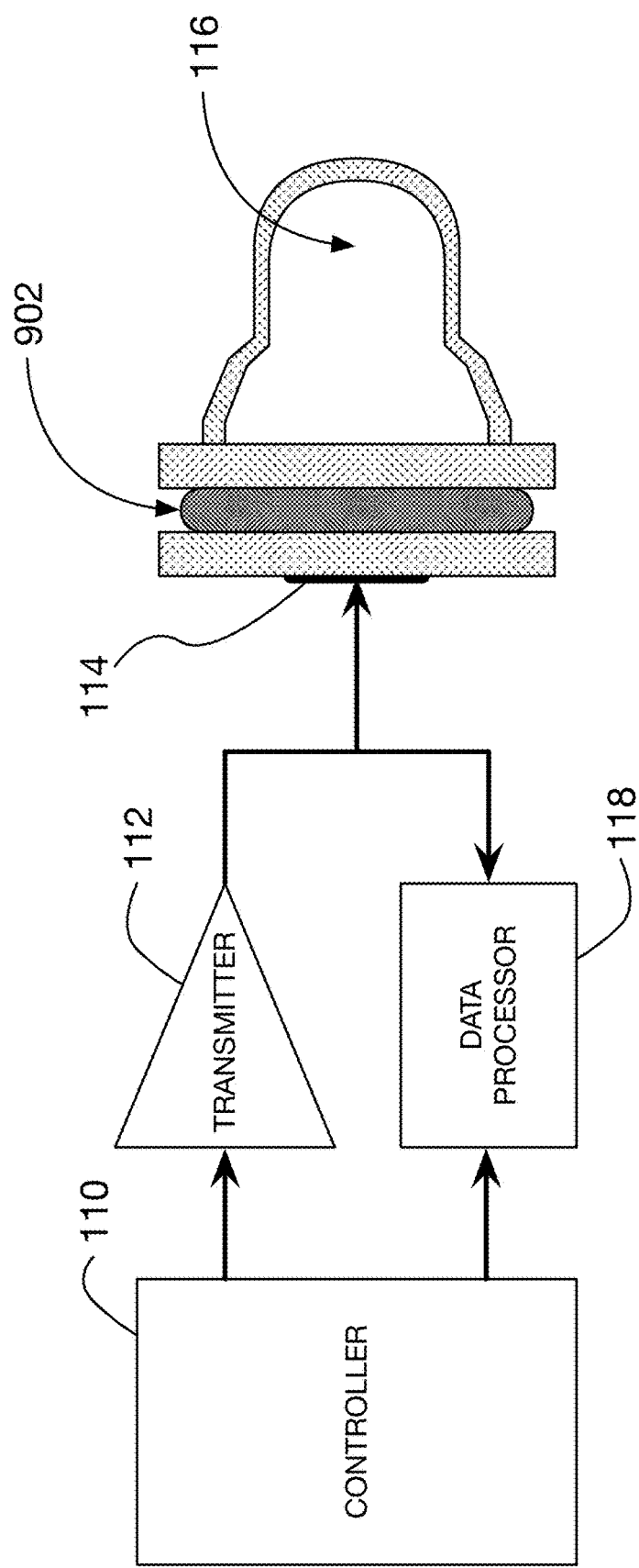
FIG. 9 depicts an example embodiment of the present disclosure wherein an acoustic couplant is interposed between the transducer assembly and the test chamber.
Figure 10:
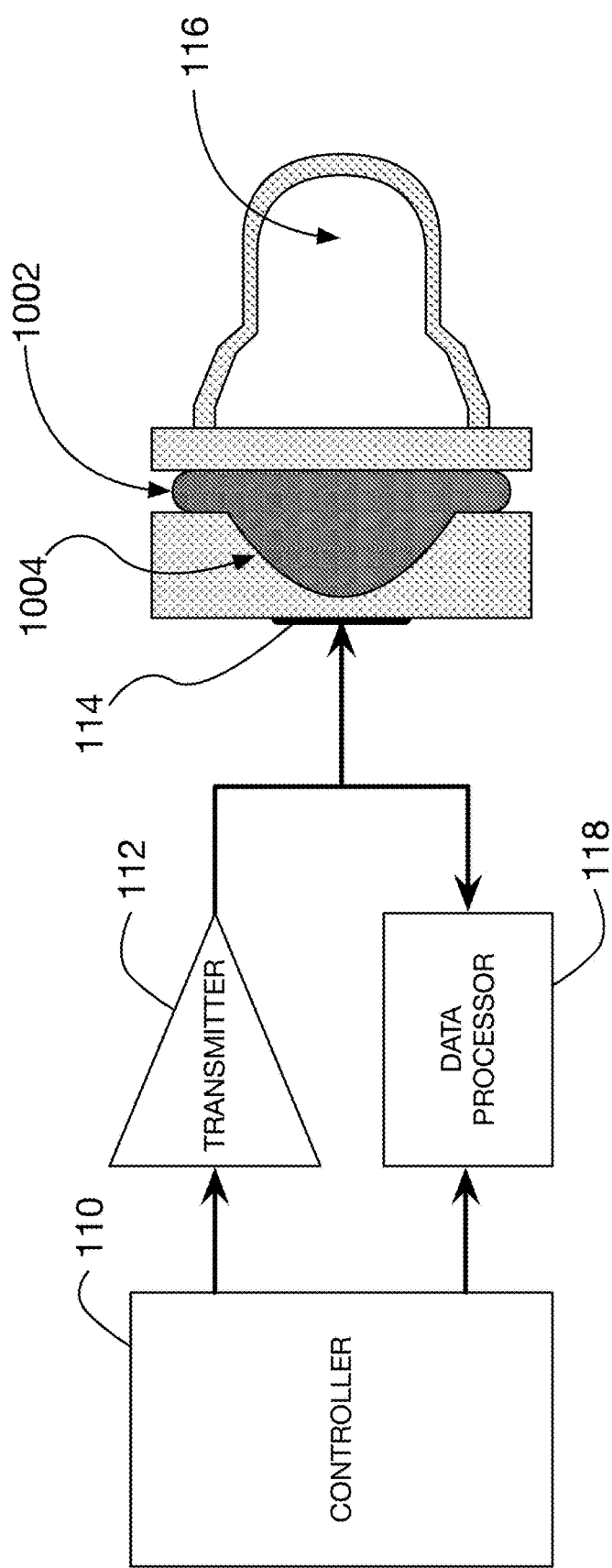
FIG. 10 depicts an example embodiment of the present disclosure wherein a focusing element is associated with the transducer assembly and an acoustic couplant is interposed between the transducer assembly and the test chamber.
Figure 11:
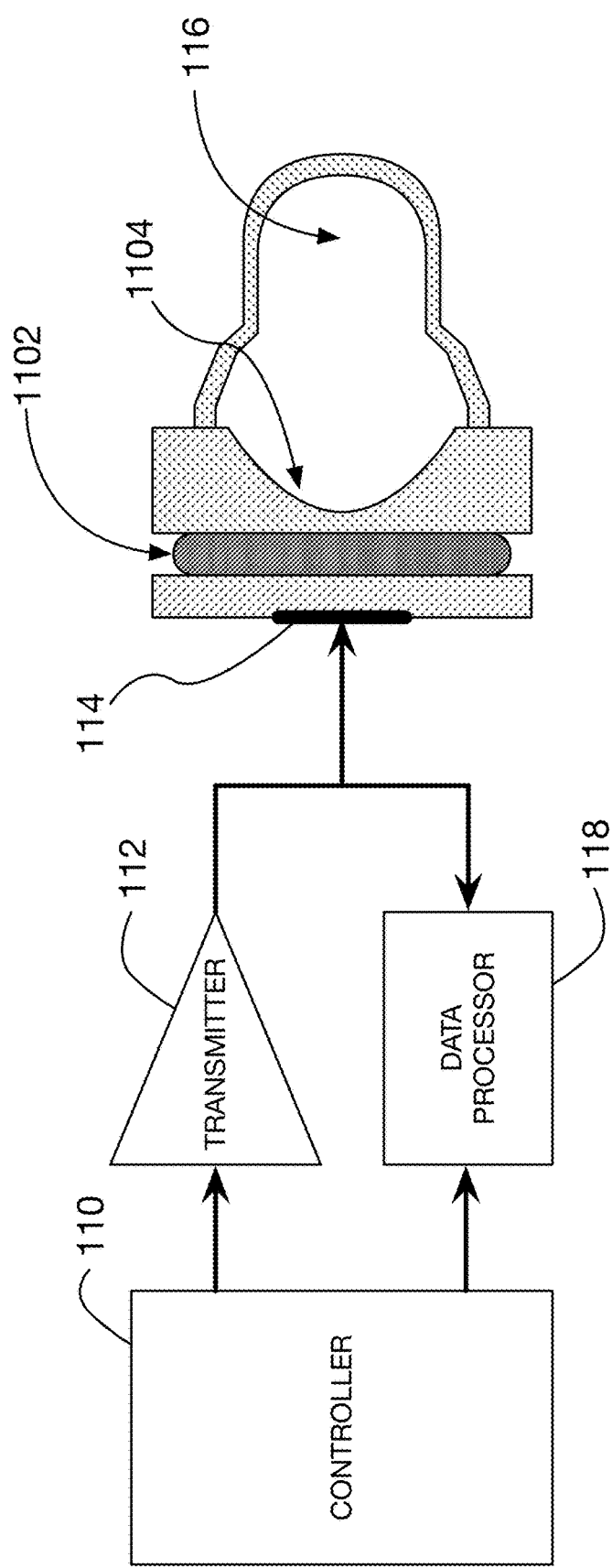
FIG. 11 depicts an example embodiment of the present disclosure wherein a focusing element is associated with the test chamber and an acoustic couplant is interposed between the transducer assembly and the test chamber.

In an example embodiment, shown in FIG. 9, a separable test chamber 116 is provided with a couplant 902. In many commercial applications, the separable test chamber will be particularly useful as a consumable component. Throughout this application we refer to the separable test chamber as "consumable," while recognizing that it could be a reusable component. In the context of this embodiment, we describe an acoustic path comprising of a transducer assembly 114 (instrument), a couplant 902 (consumable), and test chamber 116 (consumable). Additionally, a focusing element can be interposed between the transducer assembly and couplant, or between the couplant and test chamber. In one alternative embodiment (shown in FIG. 10) the focusing element 1004 is combined with the instrument, and a couplant 1002 is associated with either the instrument or the consumable. The acoustic path from the transducer assembly outward is: transducer assembly 114 (instrument), focusing element 1004 (instrument), couplant 1002 (instrument or consumable), and test chamber 116 (consumable). In yet another alternative embodiment the focusing element is incorporated with the consumable, as shown in FIG. 11. In this embodiment the couplant 1102 can be associated with either the instrument or the consumable, while the focusing element 1104 is associated with the consumable.

In the example embodiment of FIG. 11, the ultrasound waveform travels from couplant 1102 to focusing element 1104. Focusing element 1104 may be shaped such that it refracts incoming ultrasound energy and focuses it within the resonant test chamber as desired. In some embodiments focusing unit 1104 is a thermoplastic, although other suitable materials may be used instead of, or in addition to, a thermoplastic. In one possible embodiment the couplant 1102 may comprise a liquid such as water. In another possible embodiment the couplant 1102 may comprise a water-based or oil-based gel such as that commonly used for ultrasound imaging.

Focusing element 1104 focuses ultrasound energy into chamber 116. Chamber 116 may also be described interchangeably as a resonant chamber, resonance chamber, or testing chamber. The focusing element 1104 is designed so that its curvature and speed of sound act to refract the transmitted ultrasound waves into a focused beam. The focusing element 1104 may be designed to form a sharp or broadly focused beam. A sharp focus will tend to impart a higher magnitude of radiation force, however the sharp focus may make the overall system more sensitive to minor errors in aligning the ultrasound beam and the resonant chamber 116. Alternative the focusing element 1104 may be designed to more broadly focus the ultrasound beam. This may generate a lower magnitude of radiation force, but will make the system less sensitive to errors in the alignment of the ultrasound beam with the resonant chamber 116.

Figure 12:
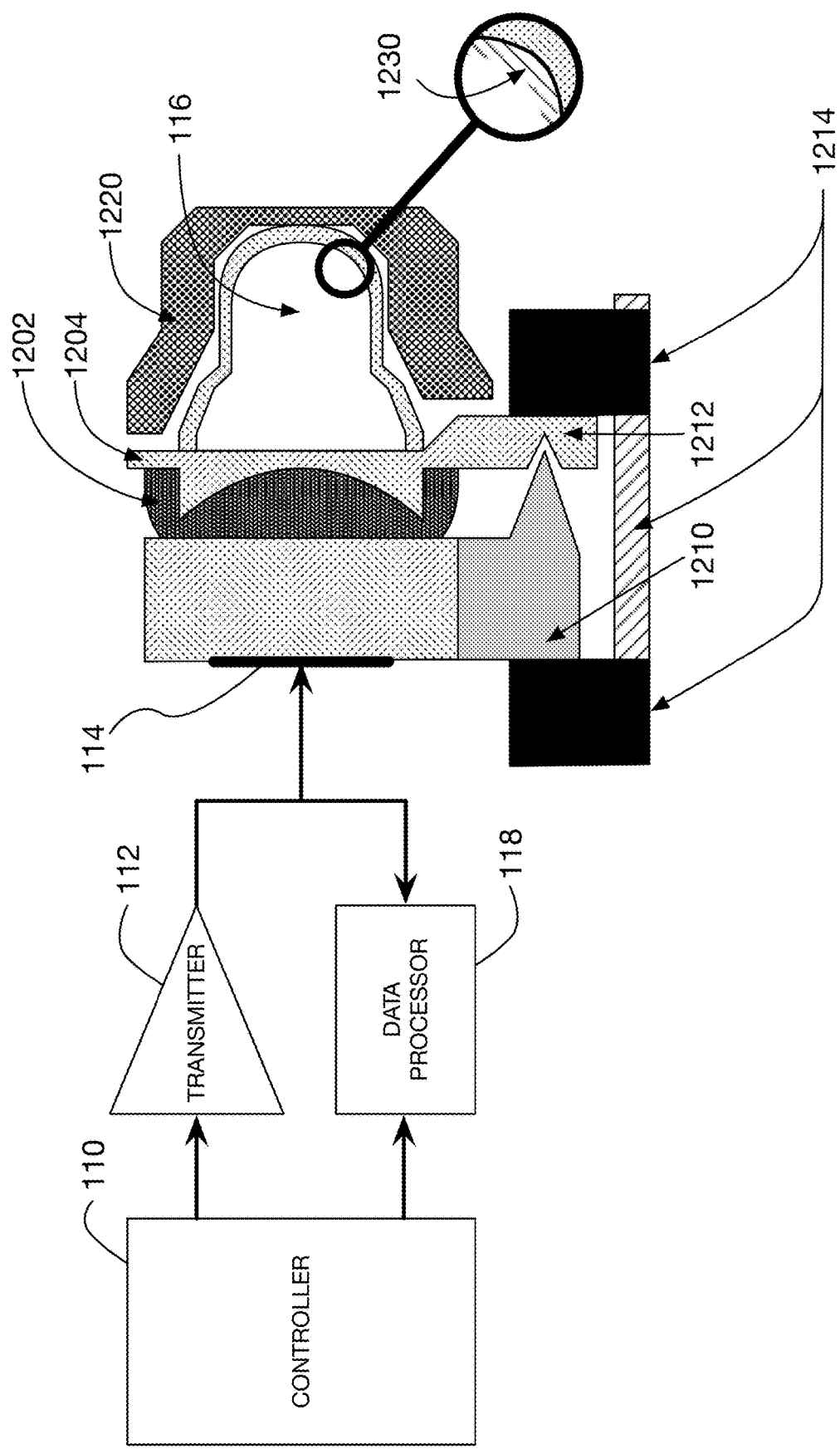
FIG. 12 depicts an example embodiment of the present disclosure incorporating numerous additional elements.

FIG. 12 depicts an alternative embodiment comprising a durable instrument and a consumable test cartridge. The controller 110, transmitter 112, transducer assembly 114, data processor 118, transducer alignment feature 1210, and clamping mechanism 1214 are incorporated in the instrument. The test chamber 116, couplant 1202, focusing element 1204, chamber alignment feature 1212, thermal control unit 1220, and surface modification 1230 are incorporated in the consumable.

In the embodiment of FIG. 12 the consumable component is brought into acoustic contact with the instrument by the action of a clamping mechanism 1214. In one embodiment the clamping mechanism is lead screw actuated by a stepper motor. Other embodiments may include, for example, a mechanically actuated lever or some other mechanical mechanism. In cases where the couplant 1202 is a fairly firm material, the clamping mechanism 1214 might require significant force to eliminate any air gaps and form good acoustic contact. In one embodiment the clamping mechanism 1214 applies about 110 Newtons of force for clamping a single resonant chamber 116. In an alternative embodiment, where a single consumable consists of multiple resonant chambers, a single clamping mechanism may be shared across channels. In this case the clamping mechanism may be required to apply more than 110 Newtons of force. For example, in an embodiment having four chambers, the clamping mechanism may apply about 440 Newtons of force.

In the embodiment of FIG. 12 alignment features 1210 and 1212 are associated with the transducer assembly 114 and the focusing component 1204. The alignment features 1210 and 1212 fit together so that the acoustic beam is precisely generated and accurately placed within the test chamber 116. In one embodiment the alignment feature 1210 incorporates four different components. Two of these are pins that each have an axis parallel with the ultrasound beam. One of these pins may fit into a hole as a component of transducer alignment feature 1212. The other pin may fit a slot as a component of chamber alignment feature 1212. In addition to the pin/hole and pin/slot alignment features, another embodiment may include at least one hard stops to control the degree of compression of the couplant 1202. In one embodiment the hard stops consist of rails above and below the couplant 1202 and associated with the focusing component 1204 that come into contact with the transducer assembly 114. Together these rails may force the focusing assembly 1204 to be parallel with the face of the transducer assembly 114.

In the embodiment of FIG. 12, the test chamber 116 is in thermal contact with a thermal control unit 1220. Since coagulation is a temperature-dependent process, the use of a thermal control unit serves to improve repeatability and increase the rate of coagulation so that clinicians receive results more rapidly. In one embodiment the temperature control unit is an aluminum block with an embedded thermistor and an electric heater. The thermistor acts as an input to a PID Controller (Proportional-Integral-Derivative Controller). In another embodiment the thermal control unit makes use of a Peltier device to enable both heating and cooling of the sample relative to its incoming temperature.

In the embodiment of FIG. 12, the interior surface of the test chamber 116 is formed or modified so as to have a surface 1230 conducive to clot adhesion. Such a treatment may be needed so that as the blood clots and platelets contract, the clot cannot pull away from the chamber wall. This may be advantageous because, should the clot pull away from chamber wall, the assumed properties upon which a computational or analytic model is built can be wrong. For example, instead of a uniform material extending all throughout the test chamber 116, a chamber with a retracted clot will include a serum layer filling a gap between the contracted clot and the resonant chamber wall. Such a gap will alter the resonant geometry of the resonant chamber, thereby biasing modulus measurements under these conditions. Even if clot retraction only opens a tiny gap between the clot and the chamber wall, the boundary conditions upon which our models are predicated will no longer be appropriate and therefore estimation of mechanical properties will be corrupted. Even when we restrict ourselves to characterizing the mechanical properties (not computing absolute properties) the characterization will be corrupted by the altered boundary conditions in the chamber. These errors can be eliminated by forming a chamber with a rough inner surface to which the clot can stay firmly adhered. Such a surface can be formed by patterning the injection mold used to form the chamber, or by roughening the interior surface after manufacture through a mechanism like bead blasting. Alternatively the interior surface can undergo plasma or corona treatment, which can both roughen the surface and modify its chemical properties to enhance clot adhesion. In another alternative embodiment the inner surface can be treated by adhering a protein like fibronectin, to which the clot can adhere.

Figure 13:
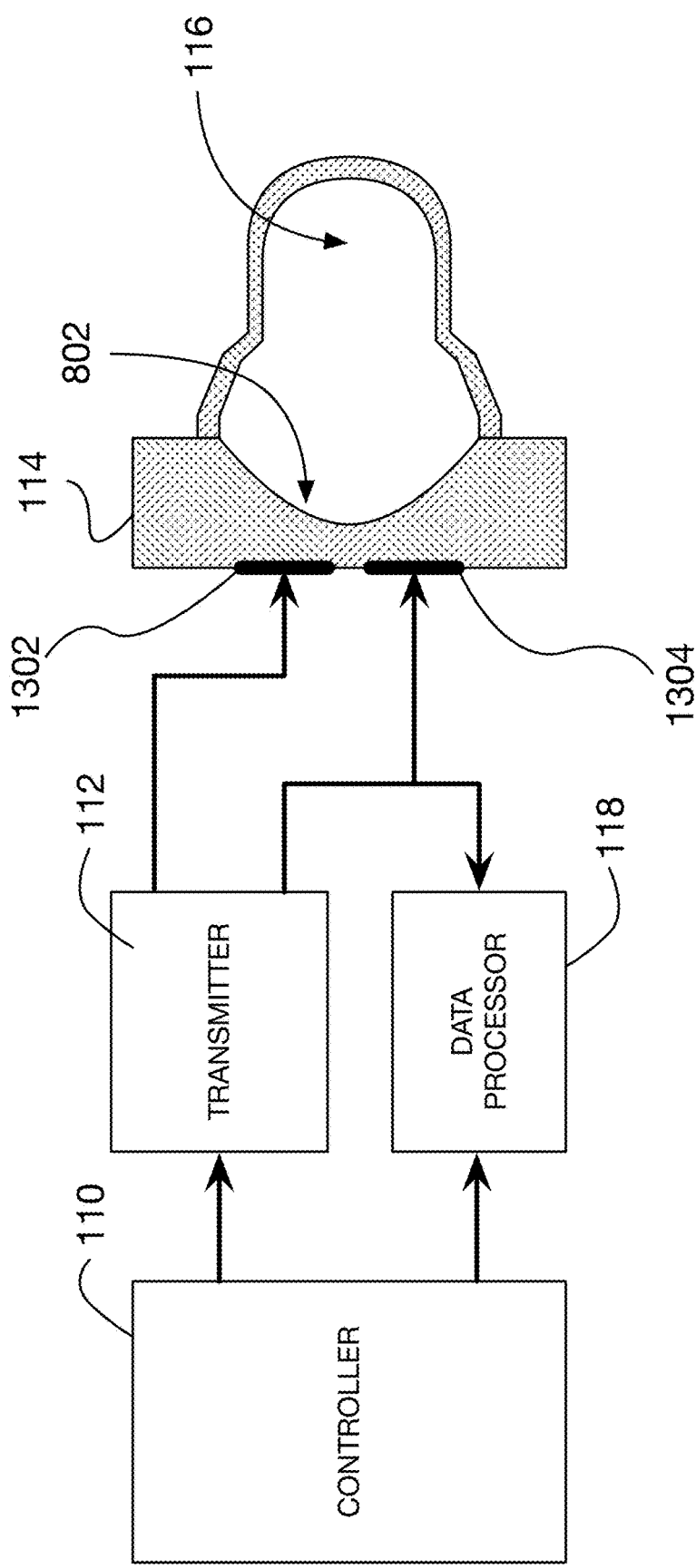
FIG. 13 depicts an example embodiment of the present disclosure wherein the transducer assembly comprises two separate transducer elements.

Another alternative embodiment of the present disclosure is shown in FIG. 13. In this embodiment the transducer assembly 114 comprises a focusing element 802, and two separate transducer elements 1302 and 1304. The first transducer element 1302 is connected to the transmitter but not the data processor and is intended to transmit forcing waveforms. The second transducer element 1304 is connected to both the transmitter and the data processor and is intended to transmit sensing waveforms and receive their echoes. The configuration of FIG. 13 may prove advantageous because, for example, the ultrasound beam shape most desirable for applying forcing waveforms may be different than that which is optimal for sensing. Furthermore, as the forcing waveforms are generally higher in energy than the sensing waveforms, this configuration likely reduces the requirements on protection circuitry associated with the data processor and improves sensitivity.

Figure 14:
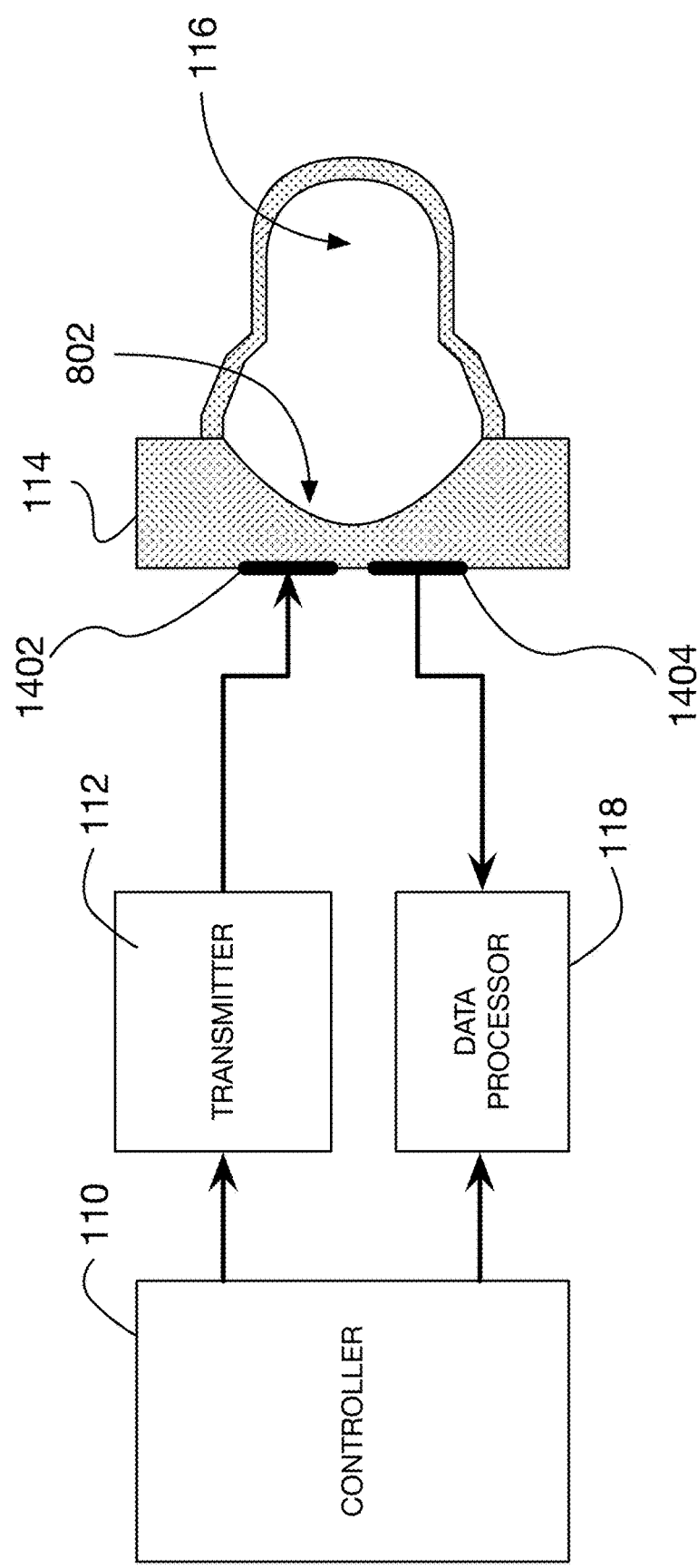
FIG. 14 depicts an embodiment of the present disclosure wherein the transducer assembly comprises two separate transducer elements with one dedicated to waveform transmission and the other dedicated to waveform reception.

Another alternative embodiment of the present disclosure is shown in FIG. 14. In this embodiment the transducer assembly 114 comprises a focusing element 802, and two separate transducer elements 1402 and 1404. The first transducer element 1402 is connected to the transmitter but not the data processor and is intended solely for waveform transmission. The second transducer element 1404 is connected to the data processor and is intended solely for echo reception. The configuration of FIG. 14 may prove advantageous because it will eliminate the need for protection circuitry associated with the data processor.

One advantage of the present disclosure over the prior art is a significant reduction in required blood volume for testing. For example, at least one prior-art method required a 60 ml sample of blood per test. In various embodiments described herein, only about 330 microliters per test chamber is required. Larger or smaller volumes of blood may be used as well, depending on the testing conditions. This reduced test chamber volume allows a patient to provide less blood while also benefiting from multiple tests in parallel within a single cartridge. In some embodiments, a single cartridge may comprise multiple test chambers that can be tested in parallel. In alternative embodiments in which the focusing element is incorporated in the transducer assembly the total blood volume may be reduced even further to as few as tens of microliters per test chamber.

In one embodiment, described above, the sensing waveform is designed so as to impart no significant acoustic radiation force upon the sample. In other embodiments, however, the sensing waveform may impart a small amount of radiation force. In these embodiments the measured displacements will include a superposition of resonant time-displacement curves. The dominant component of this superposition will be the resonant time-displacement curve resulting from the application of the forcing waveform. However, added to this curve will be smaller delayed responses from each of the sensing waveforms. In cases where the displacements due to the applied sensing waveforms have a significant effect, the ideal response can be reconstructed by deconvolving the inputs. The impact of small amounts of radiation force from the sensing waveforms might also be mitigated by lowering the rate of sensing waveform transmission.

The present disclosure has numerous applications beyond the measurement of coagulation in human blood. For example, in the veterinary sciences and in biomedical research it may be useful to quantify the process of blood clotting samples from non-human animals.

In the food industry there is strong interest in quantifying the mechanical properties of foods and food additive. In that domain it would be straightforward to fill a resonant chamber with the food to be tested. One might find it valuable to apply the present disclosure to monitor the aging of cheese or other dynamic processes. In one example, the present disclosure could be applied to measure aging of a cheese wheel. Large cheese wheels can be over 50 inches in diameter. Such a cheese wheel could be considered a resonant chamber in the context of the present disclosure. With dimensions approximately 300 times larger than the resonant test chamber considered in the detailed examples above, it may prove advantageous to scale the operating frequency similarly. This suggests that measurement of such a large object could require the use of lower frequency acoustic energy; possibly extending into the audible regime. The chamber of this application would be formed by the boundary of the cheese wheel itself with the surrounding air forming a free boundary, in contrast to the fixed boundary discussed above for blood.

In the art of tissue engineering there is an unmet need for measuring the mechanical changes that occur as cells grow, mature, and build extracellular matrices within certain tissue-engineered constructs. The present disclosure could be applied to that problem by growing cells within a resonant chamber. Alternatively the matrix upon which cells grow could be placed in a nutritive broth so the geometry of the matrix itself forms the resonant geometry. In this case the analytical or computational model would assume a free boundary, rather than the infinitely stiff boundary considered elsewhere in this application.

Example—Finite Difference Time Domain Model

The example model described below is a derivation of a Finite Difference Time Domain model for radiation force induced shear waves in cylindrical geometry. This formulation can be used to model time-displacements in the resonant chamber.

Our analysis begins with a velocity-stress formulation of the shear wave equation. Note that while this formulation considers velocity, results computed with this approach can be numerically integrated to yield displacements, so as to be consistent with experimental results. We expand upon traditional formulations by including a term to account for viscous losses.

$$\rho \frac{\partial}{\partial t} \vec{v}(\vec{x}, t) = \nabla \cdot \sigma(\vec{x}, t) + \vec{F}(\vec{x}, t) \quad (1)$$

$$\frac{\partial}{\partial t} \sigma(\vec{x}, t) = \left(\mu + \eta \frac{\partial}{\partial t}\right)\left[(\nabla \vec{v}(\vec{x}, t)) + (\nabla \vec{v}(\vec{x}, t))^T\right] \quad (2)$$

We expand equation 1 by expressing it in cylindrical coordinates and expanding the vector velocity into its constituent components.

$$\frac{\partial \sigma_{rr}}{\partial r} + \frac{1}{r}\frac{\partial \sigma_{r\theta}}{\partial \theta} + \frac{\partial \sigma_{rz}}{\partial z} + \frac{1}{r}(\sigma_{rr} - \sigma_{\theta\theta}) + F_r = \rho\frac{\partial v_r}{\partial t} \quad (3)$$

$$\frac{\partial \sigma_{r\theta}}{\partial r} + \frac{1}{r}\frac{\partial \sigma_{\theta\theta}}{\partial \theta} + \frac{\partial \sigma_{\theta z}}{\partial z} + \frac{2}{r}\sigma_{r\theta} + F_\theta = \rho\frac{\partial v_\theta}{\partial t} \quad (4)$$

$$\frac{\partial \sigma_{rz}}{\partial r} + \frac{1}{r}\frac{\partial \sigma_{\theta z}}{\partial \theta} + \frac{\partial \sigma_{zz}}{\partial z} + \frac{1}{r}\sigma_{rz} + F_z = \rho\frac{\partial v_z}{\partial t} \quad (5)$$

Further consideration of our problem allows significant simplification. First, we recognize that the only body force is the applied ultrasound radiation force. Assuming that force is entirely in the z direction, we can set $F_\theta=F_r=0$. Assuming that our test chamber and applied radiation force are entirely axisymmetric, we can set all dependencies upon θ equal to zero. Applying these simplifications to equations 3-5 yields:

$$\frac{\partial \sigma_{rz}}{\partial z} = \rho\frac{\partial^2 u_r}{\partial t^2} \quad (6)$$

$$0 = 0 \quad (7)$$

$$\frac{\partial \sigma_{rz}}{\partial r} + \frac{1}{r}\sigma_{rz} + F_z = \rho\frac{\partial^2 u_z}{\partial t^2} \quad (8)$$

We follow a similar strategy to expand equation 2, to yield:

$$\frac{\partial \sigma_{rz}}{\partial t} = \left(\mu + \eta\frac{\partial}{\partial t}\right)\left(\frac{\partial v_r}{\partial z} + \frac{\partial v_z}{\partial r}\right) \quad (9)$$

Collecting equations 6-9 we have:

$$\rho\frac{\partial v_r}{\partial t} = \frac{\partial \sigma_{rz}}{\partial z} \quad (10)$$

$$\rho\frac{\partial v_z}{\partial t} = \frac{\partial \sigma_{rz}}{\partial r} + \frac{1}{r}\sigma_{rz} + F_z \quad (11)$$

$$\frac{\partial \sigma_{rz}}{\partial t} = \left(\mu + \eta\frac{\partial}{\partial t}\right)\left(\rho\frac{\partial v_r}{\partial t} + \rho\frac{\partial v_z}{\partial t}\right) \quad (12)$$

Equations 10-12 form a system of partial differential equations that can be solved together to predict how radiation force will induce shear waves and how those induced shear waves will interact. This system of equations is particularly amenable to a finite difference solution using a staggered grid approach, similar to the Yee method. The finite difference representation of equations 10-12 are:

$$v_{r_{j,k}}^{i+1} = v_{r_{j,k}}^i + \frac{\Delta t}{\rho \Delta z}(\sigma_{rz_{j,k+\frac{1}{2}}}^i - \sigma_{rz_{j,k-\frac{1}{2}}}^i) \quad (13)$$

-continued $$v_{z_{j+\frac{1}{2},k+\frac{1}{2}}}^{i+1} = v_{z_{j+\frac{1}{2},k+\frac{1}{2}}}^i + \frac{\Delta t}{\rho}\left(\frac{1}{\Delta r}(\sigma_{rz_{j+1,k+\frac{1}{2}}}^i - \sigma_{rz_{j,k+\frac{1}{2}}}^i) + \frac{1}{2(j+\frac{1}{2})\Delta r}(\sigma_{rz_{j,k+\frac{1}{2}}}^i - \sigma_{rz_{j+1,k+\frac{1}{2}}}^i) + F_{z_{j+\frac{1}{2},k+\frac{1}{2}}}^i\right) \quad (14)$$

$$\sigma_{rz_{j,k+\frac{1}{2}}}^{i+1} = \sigma_{rz_{j,k+\frac{1}{2}}}^i + \frac{\mu\Delta t}{\Delta z}(v_{r_{j,k+1}}^i - v_{r_{j,k}}^i) + \frac{\mu\Delta t}{\Delta z}(v_{z_{j+\frac{1}{2},k++\frac{1}{2}}}^i - v_{z_{j-\frac{1}{2},k+\frac{1}{2}}}^i) + \frac{\eta}{\Delta z}(v_{r_{j,k+1}}^{i+1} - v_{r_{j,k+1}}^i - v_{r_{j,k}}^{i+1} + v_{r_{j,k}}^i) + \frac{\eta}{\Delta z}(v_{z_{j+\frac{1}{2},k+\frac{1}{2}}}^{i+1} - v_{z_{j+\frac{1}{2},k+\frac{1}{2}}}^i - v_{z_{j-\frac{1}{2},k+\frac{1}{2}}}^{i+1} + v_{z_{j-\frac{1}{2},k+\frac{1}{2}}}^i) \quad (15)$$

Figure 15:
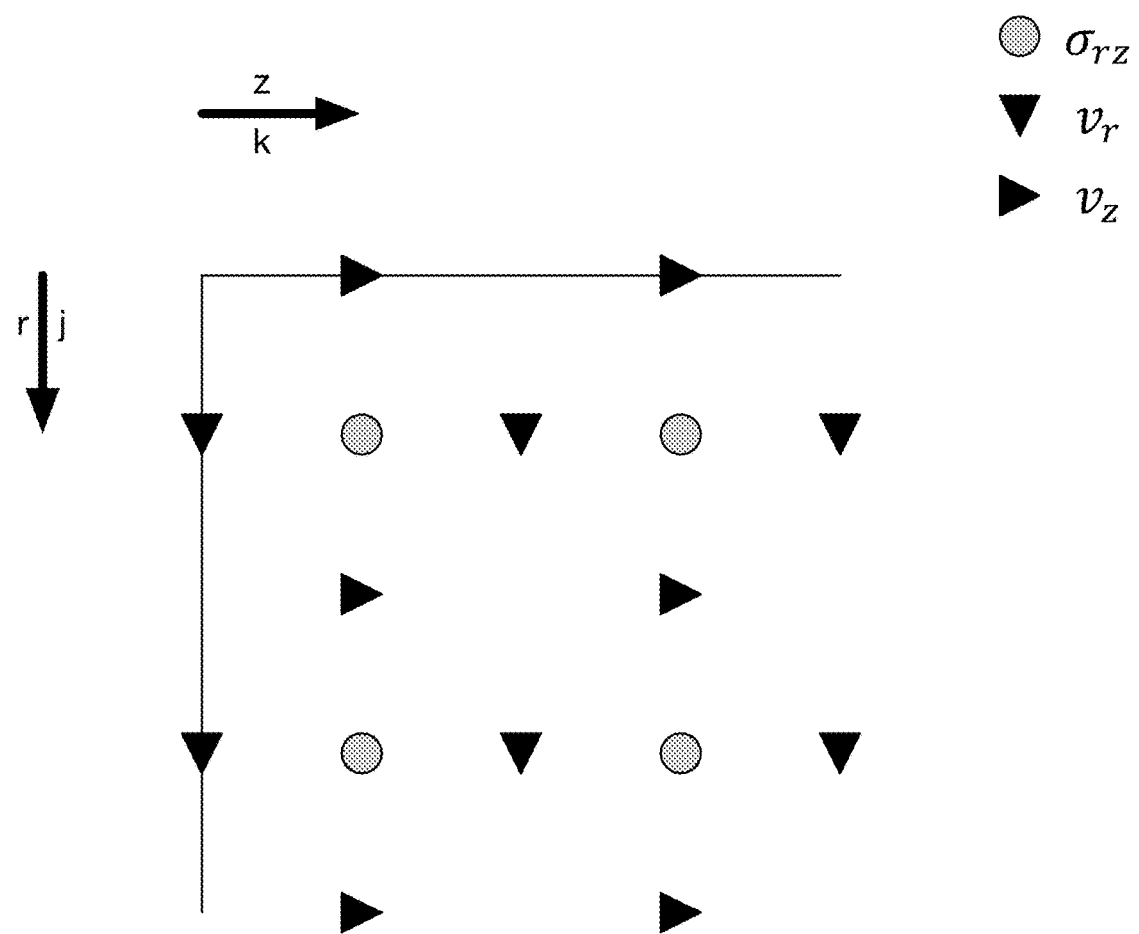
FIG. 15 shows the computational grid used for the Finite Difference Time Domain method described in the present disclosure.

The mathematical formulation described above can be implemented numerically using a staggered grid approach as shown in FIG. 15. Each computational cycle consists of two steps. In the first step the velocity components are computed using the finite difference equations above. In the next step the shear is computed using the finite difference equations.

Example—Analytical Modeling of Impulse-Induced Resonance

The example analytical model derived below represents the mechanical model of blood clot displacement in a cylindrical resonant chamber. The model qualitatively captures the observed behaviors in real-world experiments.

Our analysis is based upon the well-known Cauchy-Navier Equation for linear elasticity. We utilize a formulation incorporating viscoelastic material properties.

$$\left(\left(\lambda + \mu + (\eta_p + \eta_s)\frac{d}{dt}\right)\nabla(\nabla \cdot \vec{u}(\vec{x},t))\right) + \left(\left(\mu + \eta_s\frac{d}{dt}\right)\nabla^2 \vec{u}(\vec{x},t)\right) - \rho\frac{d^2}{dt^2}\vec{u}(\vec{x},t) = \vec{F}(\vec{x},t) \quad (16)$$

In our initial experiments we use a cylindrical test volume with radiation force applied to a smaller radius cylindrical volume with the same central axis as the test volume. This geometry ensures that there will be no variation in parameters with angle. We also assume an infinite length, which further simplifies the problem by eliminating variation in range. We apply these simplifications to the components of (16):

$$\nabla(\nabla \cdot \vec{u}(\vec{x},t)) = \nabla\left(\frac{1}{r}\frac{d}{dr}(ru_r) + \frac{1}{r}\frac{d}{d\phi}u_\phi + \frac{d}{dz}u_z\right) \quad (17)$$

Because of cylindrical symmetry and an infinite length we can assume that all derivatives with respect to φ and z are equal to zero. Thus (17) becomes:

$$\nabla(\nabla \cdot \vec{u}(\vec{x},t)) = \nabla\left(\frac{1}{r}\frac{d}{dr}(ru_r)\right) \quad (18)$$

We now take the gradient to yield:

$$\nabla(\nabla \cdot \vec{u}(\vec{x}, t)) = \left[\frac{d}{dr}\left(\frac{1}{r}\frac{d}{dr}(ru_r)\right) + \frac{d}{dr}\left(\frac{1}{r}\frac{d}{d\phi}u_\phi\right) + \frac{d^2}{drdz}(u_z)\right] \quad (19)$$
$$\hat{r} + \left[\frac{1}{r}\frac{d^2}{d\phi dr}(ru_r) + \frac{1}{r}\frac{d^2}{d\phi^2}u_\phi + \frac{1}{r}\frac{d^2}{d\phi dz}(u_z)\right]$$
$$\hat{\phi} + \left[\frac{d}{dz}\left(\frac{1}{r}\frac{d}{dr}(ru_r)\right) + \frac{d}{dz}\left(\frac{1}{r}\frac{d}{d\phi}u_\phi\right) + \frac{d^2}{drdz}(u_z)\right]\hat{z}$$

We again appreciate that all derivatives with respect to $\phi$ and z are equal to zero. Thus (19) can be simplified to:

$$\nabla(\nabla \cdot \vec{u}(\vec{x}, t)) = \left[\frac{d}{dr}\left(\frac{1}{r}\frac{d}{dr}(ru_r)\right)\right]\hat{r} + 0\hat{\phi} + 0\hat{z} \quad (20)$$

We consider another component of (16):

$$\nabla^2\vec{u}(\vec{x}, t) = \left[\nabla^2 u_r - \frac{1}{r^2}u_r - \frac{2}{r^2}\frac{d}{d\phi}u_\phi\right] \quad (21)$$
$$\hat{r} + \left[\nabla^2 u_\phi - \frac{1}{\phi^2}u_\phi - \frac{2}{r^2}\frac{d}{d\phi}u_r\right]\hat{\phi} + [\nabla^2 u_z]\hat{z}$$

Again, we recognize that all derivatives with respect to $\phi$ and z are equal to zero. Furthermore, the displacement component with respect to $\phi$ is also equal to zero. Thus (21) simplifies to:

$$\nabla^2\vec{u}(\vec{x}, t) = \left[\nabla^2 u_r - \frac{1}{r^2}u_r\right]\hat{r} + 0\hat{\phi} + [\nabla^2 u_z]\hat{z} \quad (22)$$

We expand the Laplacians to yield:

$$\nabla^2\vec{u}(\vec{x}, t) = \left[\frac{1}{r}\frac{d}{dr}\left(r\frac{d}{dr}u_r\right) + \frac{1}{r^2}\frac{d^2}{d\phi^2}u_r + \frac{d^2}{dz^2}u_r + \frac{1}{r^2}u_r\right]\hat{r} + \quad (23)$$
$$0\hat{\phi} + \left[\frac{1}{r}\frac{d}{dr}\left(r\frac{d}{dr}u_z\right) + \frac{1}{r^2}\frac{d^2}{d\phi^2}u_z + \frac{d^2}{dz^2}u_z\right]\hat{z}$$

Again, we recognize that the derivatives with respect to $\phi$ and z are equal to zero. Thus (23) becomes:

$$\nabla^2\vec{u}(\vec{x}, t) = \left[\frac{1}{r}\frac{d}{dr}\left(r\frac{d}{dr}u_r\right) + \frac{1}{r^2}u_r\right]\hat{r} + 0\hat{\phi} + \left[\frac{1}{r}\frac{d}{dr}\left(r\frac{d}{dr}u_z\right)\right]\hat{z} \quad (24)$$

The partial differential equation of (16) can be split into three different equations; one for each direction. We begin by considering the result in the z direction. Note that the displacement in the z direction is a function only of r and t as the $\phi$ and z dependencies are eliminated by radial symmetry and the infinite length of the model:

$$\left(\left(\lambda + \mu + (\eta_p + \eta_s)\frac{d}{dt}\cdot\right)\nabla(\nabla \cdot u_z(r, t))\right) + \quad (25)$$

-continued
$$\left(\left(\mu + \eta_s\frac{d}{dt}\cdot\right)\nabla^2 u_z(r, t)\right) - \rho\frac{d^2}{dt^2}u_z(r, t) = F_z(t)$$

Substituting (20) and (24) back into (25) yields:

$$\left(\left(\lambda + \mu + (\eta_p + \eta_s)\frac{d}{dt}\cdot\right)0\right) + \quad (26)$$
$$\left(\left(\mu + \eta_s\frac{d}{dt}\cdot\right)\frac{1}{r}\frac{d}{dr}\left(r\frac{d}{dr}u_z(r, t)\right)\right) - \rho\frac{d^2}{dt^2}u_z(r, t) = F_z(t)$$

Expanding (26) yields:

$$\left(\left(\mu + \eta_s\frac{d}{dt}\cdot\right)\frac{1}{r}\left(r\frac{d^2}{dr^2}u_z(r, t) + \frac{d}{dr}u_z(r, t)\right)\right) - \rho\frac{d^2}{dt^2}u_z(r, t) = F_z(t) \quad (27)$$

Simplifying further yields:

$$\left(\left(\mu + \eta_s\frac{d}{dt}\cdot\right)\left(\frac{d^2}{dr^2}u_z(r, t) + \frac{1}{r}\frac{d}{dr}u_z(r, t)\right)\right) - \rho\frac{d^2}{dt^2}u_z(r, t) = F_z(t) \quad (28)$$

Note that (28) includes no dependence upon the radial displacement. Thus the potential system of partial differential equations becomes a single partial differential equation.

Oscillatory Force:

We solve equation 28 by considering a solution of the form below, in which the displacement is oscillatory.

$$u_z(r, t) = S(r)e^{j\omega t} \quad (29)$$

We further assume that the applied force is also oscillatory.

$$F_z(r, t) = F(r)e^{j\omega t} \quad (30)$$

Substituting (29) into (28) yields:

$$\left(\left(\mu + \eta_s\frac{d}{dt}\cdot\right)\left(\frac{d^2}{dr^2}S(r)e^{j\omega t} + \frac{1}{r}\frac{d}{dr}S(r)e^{j\omega t}\right)\right) - \rho\frac{d^2}{dt^2}S(r)e^{j\omega t} = \quad (31)$$
$$F(r)e^{j\omega t}$$

Evaluating the derivatives with respect to time yields:

$$(\mu + j\omega\eta_s)\left(\frac{d^2}{dr^2}S(r)e^{j\omega t} + \frac{1}{r}\frac{d}{dr}S(r)e^{j\omega t}\right) + \rho\omega^2 S(r)e^{j\omega t} = F(r)e^{j\omega t} \quad (32)$$

We set aside the $e^{j\omega t}$ term, which occurs throughout (32) to yield:

$$(\mu + j\omega\eta_s)\left(\frac{d^2}{dr^2}S(r) + \frac{1}{r}\frac{d}{dr}S(r)\right) + \rho\omega^2 S(r) = F(r) \quad (33)$$

To simplify notation we replace $(\mu+j\omega\eta_s)$ with a general complex shear modulus of G so that (33) becomes:

$$G\left(\frac{d^2}{dr^2}S(r) + \frac{1}{r}\frac{d}{dr}S(r)\right) + \rho\omega^2 S(r) = F(r) \quad (34)$$

The solution of this equation depends upon the exact form of the forcing function. One simple form assumes a constant force F within some transmit beam radius $r_{tx}$, and a force of 0 outside that radius. For this simple forcing function the solution has two domains, one inside the radius $r_{tx}$ and one outside that radius. The solution is:

$$S_1(r) = c_1 J_0\left(\frac{\sqrt{\rho\omega^2}}{\sqrt{G}}r\right) + c_2 Y_0\left(\frac{\sqrt{\rho\omega^2}}{\sqrt{G}}r\right) + \frac{F}{\sqrt{\rho\omega^2}} \quad (35)$$

for $r \le r_{tx}$ $$S_2(r) = c_3 J_0\left(\frac{\sqrt{\rho\omega^2}}{\sqrt{G}}r\right) + c_4 Y_0\left(\frac{\sqrt{\rho\omega^2}}{\sqrt{G}}r\right) \text{ for } r > r_{tx}$$

Where $J_0$ is the zero$^{th}$ order Bessel Function of the first kind and $Y_0$ is the zero$^{th}$ order Bessel Function of the second kind We can further simplify this solution by considering our boundary conditions. The derivative of the solution at r=0 must be 0. Since $Y_0$ does not have a finite derivative at 0 we know that $c_2$=0. This leaves our solution as:

$$S_1(r) = c_1 J_0(Ar) + \frac{F}{\sqrt{\rho\omega^2}} \quad \text{for } r \le r_{tx} \quad (36)$$

$$S_2(r) = c_3 J_0(Ar) + c_4 Y_0(Ar) \quad \text{for } r > r_{tx}$$

Note that to simplify notation we have replaced $$\frac{\sqrt{\rho\omega^2}}{\sqrt{G}}$$

with A. We now solve for the arbitrary constants by considering the boundary conditions and continuity conditions of the problem. We assume that the clot is rigidly adhered to the chamber wall and therefore $S_2$(R)=0, where R is the radius of the test chamber. Furthermore, the two solutions must be continuous at their junction so that $S_1$ $(r_b)$=$S_2$ $(r_b)$. Finally, the two solutions must have continuous derivatives at their junction so that $S_1'(r_b)$=$S_2'(r_b)$. We can express these three conditions as shown below:

$$c_3 J_0(AR) + c_4 Y_0(AR) = 0 \quad (37)$$

$$c_1 J_0(Ar_b) + \frac{F}{\sqrt{\rho\omega^2}} - c_3 J_0(Ar_b) - c_4 Y_0(Ar_b) = 0$$

$$c_1 J_0'(Ar_b) - c_3 J_0'(Ar_b) - c_4 Y_0'(Ar_b) = 0$$

Recognizing that $J_0'(Ar)=AJ_1(Ar)$ and $Y_0'(Ar)=-AY_1(Ar)$, and reformulating the above expressions into a single system of linear equations yields:

$$\begin{bmatrix} 0 & J_0(AR) & Y_0(AR) \\ J_0(Ar_b) & -J_0(Ar_b) & -Y_0(Ar_b) \\ -AJ_1(Ar_b) & AJ_1(Ar_b) & AY_1(Ar_b) \end{bmatrix} \begin{bmatrix} c_1 \\ c_3 \\ c_4 \end{bmatrix} = \begin{bmatrix} 0 \\ -\frac{F}{\sqrt{\rho\omega^2}} \\ 0 \end{bmatrix} \quad (38)$$

This system of equations can be solved using Gaussian Elimination. We are primarily concerned within the region of force application, where $r \le r_{tx}$. Thus the coefficient of greatest interest is $c_1$. Solving for $c_1$ yields:

$$c_1 = \frac{F}{\sqrt{\rho\omega^2} J_0(AR)} \left(\frac{J_0(AR)Y_1(Ar_b) - Y_0(AR)J_1(Ar_b)}{Y_0(Ar_b)J_1(Ar_b) - J_0(Ar_b)Y_1(Ar_b)}\right) \quad (39)$$

$$c_3 = -\frac{F}{\sqrt{\rho\omega^2} J_0(AR)} \left(\frac{Y_0(AR)J_1(Ar_b)}{Y_0(Ar_b)J_1(Ar_b) - J_0(Ar_b)Y_1(Ar_b)}\right) \quad (40)$$

$$c_4 = \frac{F}{\sqrt{\rho\omega^2}} \left(\frac{J_1(Ar_b)}{Y_0(Ar_b)J_1(Ar_b) - J_0(Ar_b)Y_1(Ar_b)}\right) \quad (41)$$

The above expressions offer a rigorous solution to the analytical formulation presented here. Unfortunately these rigorous solutions are prone to numerical instability when the operands of the Bessel Functions become large. In these cases numerical errors in the evaluation of the Bessel Functions are reinforced by subtraction so that the evaluation of $c_1$, $c_3$, and $c_4$ may be effectively useless.

The numerical instabilities of (39), (40), and (41) can be mitigated by using simpler expressions for the Bessel Functions with large operands. We use the following simplifications for large operands.

$$J_0(x) \approx \sqrt{\frac{2}{\pi x}} \cos\left(x - \frac{\pi}{4}\right) \quad \text{for large } x \quad (42)$$

$$J_1(x) \approx \sqrt{\frac{2}{\pi x}} \cos\left(x - \frac{3\pi}{4}\right) \quad \text{for large } x \quad (43)$$

$$Y_0(x) \approx \sqrt{\frac{2}{\pi x}} \sin\left(x - \frac{\pi}{4}\right) \quad \text{for large } x \quad (44)$$

$$Y_1(x) \approx \sqrt{\frac{2}{\pi x}} \sin\left(x - \frac{3\pi}{4}\right) \quad \text{for large } x \quad (45)$$

By applying these expressions to equations 39-41, and then employing trigonometric identities, we are able to reformulate $c_1$, $c_3$, and $c_4$ so that they are numerically stable. Note that this reformulation is only valid for large operands, so an empirically determined transition between the two expressions must be employed.

The received signal is a weighted sum of the signals received from each of the annuli within the receive beam. Formally the signals may be considered complex exponentials and the resultant sum a complex exponential, which is then analyzed to determine the displacement. For small displacements such that the first terms of the Taylor Series are reasonable approximations to the complex exponential (cos(x)≈1 and (sin(x)≈x), the complex exponential can be ignored so that the estimated displacement will approximate the sum of displacements across the annuli.

Thus the estimated displacement is weighted sum of the actual displacements over an axisymmetric region. If the effective receive beam radius is less than the transmit beam radius then the estimated displacement is:

$$d_1 = 2\pi \int_0^{r_{rx}} r \cdot s_1(r) dr = 2\pi \int_0^{r_{rx}} r \cdot \left(c_1 J_0(Ar) + \frac{F}{\sqrt{\rho\omega^2}}\right) dr \quad (46)$$

The integral of (46) is readily computed with the knowledge that $$\int_0^x r(J_0(Ar)) dr = \frac{x}{A} J_1(ax).$$

$$d_1 = c_1 \frac{2\pi r_{rx}}{A} J_1(Ar_{rx}) + \frac{2\pi r_{rx}^2 F}{2\sqrt{\rho\omega^2}} \quad (47)$$

If however the receive beam is larger than the transmit beam, then the solution takes on the form:

$$d_2 = 2\pi \left( \int_0^{r_{tx}} r \cdot s_1(r) dr + \int_{r_{tx}}^{r_{rx}} r \cdot s_2(r) dr \right) \quad (48)$$

$$d_2 = 2\pi \left( \int_0^{r_{tx}} r \cdot \left(c_1 J_0(Ar) + \frac{F}{\sqrt{\rho\omega^2}}\right) dr + \int_{r_{tx}}^{r_{rx}} r \cdot (c_3 J_0(Ar) + c_4 Y_0(Ar)) dr \right) \quad (49)$$

$$d_2 = 2\pi \left( c_1 \frac{r_{tx}}{A} J_1(Ar_{tx}) + \frac{F r_{tx}^2}{2\sqrt{\rho\omega^2}} + \frac{c_3}{A}(r_{rx} J_1(Ar_{rx}) - r_{tx} J_1(Ar_{tx})) + \frac{c_4}{A}(r_{rx} Y_1(Ar_{rx}) - r_{tx} Y_1(Ar_{tx})) \right) \quad (50)$$

Displacement due to Oscillatory Force from a small beam:

In some cases it will be helpful to consider the oscillatory displacement in the limit of a very small ultrasound beam. We will consider equation 36 in the limit as $r_{tx}$ approaches zero.

$$\lim_{r_b \to 0} S_1(r) = \lim_{r_b \to 0} \left(c_1 J_0(Ar) + \frac{F}{\sqrt{\rho\omega^2}}\right) \text{ for } r \leq r_{tx} \quad (51)$$

$$c_1 = \frac{F}{\sqrt{\rho\omega^2} J_0(AR)} \left( \frac{J_0(AR) Y_1(Ar_b) - Y_0(AR) J_1(Ar_b)}{Y_0(Ar_b) J_1(Ar_b) - J_0(Ar_b) Y_1(Ar_b)} \right) \quad (52)$$

We recognize that the only term dependent upon $r_b$ is the constant, $c_1$. Thus we take the limit of $c_1$ as $r_b$ goes to zero.

$$\lim_{r_b \to 0} c_1 = \lim_{r_b \to 0} \frac{F}{\sqrt{\rho\omega^2} J_0(AR)} \left( \frac{J_0(AR) Y_1(Ar_b) - Y_0(AR) J_1(Ar_b)}{Y_0(Ar_b) J_1(Ar_b) - J_0(Ar_b) Y_1(Ar_b)} \right) \quad (53)$$

$$\lim_{r_b \to 0} c_1 = \frac{F}{\sqrt{\rho\omega^2}} \left(-1 + \frac{Y_0(AR)}{J_0(AR)}\right) \quad (54)$$

Thus the displacement is equal to:

$$\lim_{r_b \to 0} S_1(r) = \frac{F}{\sqrt{\rho\omega^2}} \left(-1 + \frac{Y_0(AR)}{J_0(AR)}\right) J_0(Ar) + \frac{F}{\sqrt{\rho\omega^2}} \text{ for } \quad (55)$$
$$r \leq r_{tx}$$

We simplify further by considering the displacement at the center, i.e. the beam location:

$$\lim_{r_b \to 0} S_1(0) = \frac{F}{\sqrt{\rho\omega^2}} \frac{Y_0(AR)}{J_0(AR)} \quad (56)$$

Where $= \frac{\sqrt{\rho\omega^2}}{\sqrt{G}}$.

By examining this expression we recognize that the displacement will be maximum, i.e. the system will be in resonance, when $J_0(AR)=0$. The first zero occurs at $J_0(2.4048)$. Thus the resonant frequency can be solved as follows:

$$\frac{\sqrt{\rho\omega^2}}{\sqrt{G}} R = 2.4048 \quad (57)$$

$$f = \frac{2.4048}{2\pi R} \frac{\sqrt{G}}{\sqrt{\rho}} \quad (58)$$

Constant Force:

The above analysis is valid only for oscillatory forces. In the static case, where the force is constant over time, we must perform a separate analysis. We begin by reconsidering equation (28), copied below for clarity $$\left(\left(\mu + \eta_s \frac{d}{dt}\right)\left(\frac{d^2}{dr^2} u_z(r,t) + \frac{1}{r}\frac{d}{dr} u_z(r,t)\right)\right) - \rho \frac{d^2}{dt^2} u_z(r,t) = F_z(t) \quad (59)$$

Since we are specifically interested in the static, or DC problem, we eliminate all the derivatives with respect to t, as these must be equal to zero. We also change notation to indicate that we are considering the static shear modulus, $$G_s \left(\frac{d^2}{dr^2} u_z(r) + \frac{1}{r}\frac{d}{dr} u_z(r)\right) = F_z \quad (60)$$

As with the oscillatory problem, the solution of this equation depends upon the exact form of the forcing function. One simple form assumes a constant force F within some transmit beam radius $r_{tx}$, and a force of 0 outside that radius. For this simple forcing function the solution has two domains, one inside the radius $r_{tx}$ and one outside that radius. The solution is:

$$S_1(r) = c_1 + \frac{F r^2}{4 G_s} \text{ for } r \leq r_{tx} \quad (61)$$

$$S_2(r) = c_3 + c_4 \log(r) \text{ for } r > r_{tx}$$

We now solve for the arbitrary constants by considering the boundary conditions and continuity conditions of the problem. We assume that the clot is rigidly adhered to the chamber wall and therefore $S_2(R)=0$, where R is the radius of the test chamber. Furthermore, the two solutions must be continuous at their junction so that $S_1(r_b)=S_2(r_b)$. Finally, the two solutions must have continuous derivatives at their junction so that $S_1'(r_b)=S_2'(r_b)$. Rather than repeat the analysis used for the oscillatory solution, we instead present the solution below:

$$c_1 = \frac{Fr_{tx}^2}{2G_s}\left(\log(r_{tx}) - \log(R) - \frac{r_{tx}}{2}\right) \quad (62)$$

$$c_3 = -\frac{Fr_{tx}^2}{2G_s}\log(R) \quad (63)$$

$$c_4 = \frac{Fr_{tx}^2}{2G_s} \quad (64)$$

The estimated displacement is the average of the actual displacement over the receive beam. If the effective receive beam radius is less than the transmit beam radius then the estimated displacement is:

$$d_1 = 2\pi \int_0^{r_{rx}} r \cdot s_1(r)dr = 2\pi \int_0^{r_{rx}} r \cdot \left(c_1 + \frac{Fr^2}{4G_s}\right)dr \quad (65)$$

The integral of (47) is readily computed.

$$d_1 = \pi r_{rx}^2 c_1 + \frac{\pi F r_{rx}^4}{8G_s} \quad (66)$$

If however the receive beam is larger than the transmit beam, then the solution takes on the form:

$$d_2 = 2\pi\left(\int_0^{r_{tx}} r \cdot s_1(r)dr + \int_{r_{tx}}^{r_{rx}} r \cdot s_2(r)dr\right) \quad (67)$$

$$d_2 = 2\pi\left(\frac{c_1 r_{tx}^2}{2} + \frac{Fr_{tx}^4}{16G_s} + \left(\frac{c_3 r^2}{2} + \frac{c_4 r^2}{2}\log(r) - \frac{c_4 r^2}{4}\right)\Big|_{r_{tx}}^{r_{rx}}\right) \quad (68)$$

$$d_2 = 2\pi\left(\frac{c_1 r_{tx}^2}{2} + \frac{Fr_{tx}^4}{16G_s} + \frac{c_3}{2}(r_{rx}^2 - r_{tx}^2) + \frac{c_4}{2}(r_{rx}^2\log(r_{rx}) - r_{tx}^2\log(r_{tx})) - \frac{c_4}{4}(r_{rx}^2 - r_{tx}^2)\right) \quad (69)$$

Viscoelastic Tissue Models:

Successful application of the presented model requires the selection of an appropriate viscoelastic model, as implemented through the complex, frequency dependent shear modulus G. We have explored both the Kelvin-Voigt model (Illustration 1) and the Jeffrey model (Illustration 2). The Kelvin-Voigt model is generally well suited to modeling clot behavior however it fails to capture certain poroelastic behaviors that may be observed in blood clots. In this sense the Jeffrey model is sometimes superior.

Illustration 1

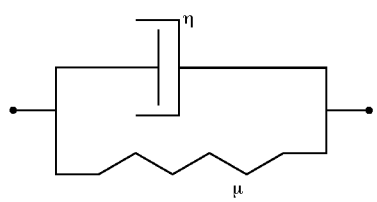

Kelvin-Voigt Model
$G = \mu + j\omega\eta$

Illustration 2

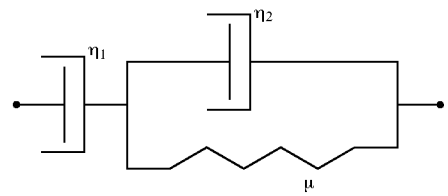

Jeffrey Model
$$G = -\omega\eta_1 \frac{\omega\eta_2 - i\mu}{\mu + i\omega(\eta_1+\eta_2)}$$

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present disclosure is not limited to the particular examples and implementations disclosed herein, but is intended to cover modifications within the spirit and scope thereof as defined by the appended claims and any and all equivalents thereof.

What is claimed is:

1. A device for estimating a mechanical property of a sample, comprising:
   a chamber configured to hold the sample;
   a transmitter configured to transmit a plurality of waveforms, including at least one forcing waveform;
   a transducer assembly operatively connected to the transmitter and configured to transform the transmit waveforms into ultrasound waveforms, the transducer assembly further configured to transmit and receive ultrasound waveforms into and out of the chamber, and the transducer assembly further configured to transform at least two received ultrasound waveforms into received electrical waveforms;
   a data processor configured to:
      receive the received electrical waveforms;
      estimate a difference in the received electrical waveforms that results at least partially from movement of the sample; and
      estimate a mechanical property of the sample by comparing at least one feature of the estimated difference to at least one predicted feature, wherein the at least one predicted feature is based on a model of an effect of the chamber wall; and
   a controller configured to control the timing of the ultrasound transmitter and data processor.

2. The device of claim 1, wherein the at least one predicted feature is based on a model of an aspect of the induced movement that is caused at least in part by a boundary effect of the chamber wall.

3. The device of claim 2, wherein the mechanical property is an indication of whether or not the chamber wall exhibits an effect on induced displacements.

4. The device of claim 1, wherein the at least one predicted feature is based on a model of an aspect of the induced movement that is caused at least in part by resonance within the chamber.

5. The device of claim 4, wherein the mechanical property is an indication of whether or not the sample can support mechanical resonance.

6. The device of claim 4, wherein the data processor is further configured to calculate a parameter indicating the strength of resonance and omit measurements with a strength of resonance falling below a predetermined threshold.

7. The device of claim 1, wherein the at least one predicted feature is based on a model of an aspect of the induced movement that is caused at least in part by reflection of an induced shear wave from the chamber wall.

8. The device of claim 7, wherein the mechanical property is an indication of whether or not the sample can support shear wave propagation.

9. The device of claim 1, wherein the at least one predicted feature is based on an analytical model.

10. The device of claim 4, wherein the at least one predicted feature comprises the period of resonance of the chamber.

11. The device of claim 1, wherein the at least one predicted feature is based on a computational model.

12. The device of claim 1, wherein the predicted features comprises a table of reference features based on the model.

13. The device of claim 1, wherein the data processor is further configured to calculate a correlation value between features of the estimated displacement and features that are based on a model, and omit data falling below a predetermined correlation threshold.

14. The device of claim 1, wherein the mechanical property is the shear modulus of the sample.

15. The device of claim 1, wherein the transducer assembly comprises a transducer used for both transmitting and receiving.

16. The device of claim 1, wherein the transducer assembly comprises a first transducer dedicated to transmitting ultrasound waveforms and a second transducer dedicated to receiving ultrasound waveforms.

17. The device of claim 1, wherein the transducer assembly comprises a transducer dedicated to transmitting forcing waveforms and a separate transducer dedicated to transmitting and receiving ultrasound waveforms associated with sensing.

18. The device of claim 1, wherein the data processor estimates the mechanical property based on an ensemble of sensing waveforms, the ensemble comprising at least 16 sensing waveforms.

19. The device of claim 1, wherein the data processor estimates differences in waveforms received from a plurality of forcing waveforms.

20. The device of claim 1, wherein the data processor comprises a received waveform digitizer.

21. The device of claim 1, wherein the sample is a blood clot.

22. The device of claim 1, wherein the data processor assumes a constant viscosity value for the sample.

23. The device of claim 1, wherein the interior surface of the chamber is formed or treated so as to promote adhesion of a forming blood clot.

24. The device of claim 1, further comprising a thermal control element in thermal communication with said chamber.

25. The device of claim 1, further comprising a focusing unit interposed between the transducer and chamber and configured to focus ultrasound waves transmitted into and received from said chamber.

26. The device of claim 1, wherein the chamber is separable from the transducer.

27. The device of claim 26, further comprising an ultrasonic couplant interposed between said transducer and said chamber so as to facilitate ultrasound propagation between said transducer and said chamber.

28. The device of claim 27, further comprising a clamping element configured to compress said ultrasonic couplant.

29. The device of claim 27, further comprising:
a transducer alignment feature associated with said transducer; and
a chamber alignment feature associated with said chamber,
wherein said transducer alignment feature and said chamber alignment feature fit together to align said transducer with said chamber.

30. A device for characterizing a mechanical property of a sample, comprising:
a resonant chamber configured to hold the sample;
a transmitter configured to transmit a plurality of waveforms, including at least one forcing waveform;
a transducer assembly operatively connected to the transmitter and configured to transform the transmit waveforms into ultrasound waveforms, the transducer assembly further configured to transmit and receive ultrasound waveforms into and out of the chamber, and the transducer assembly further configured to transform at least two received ultrasound waveforms into received electrical waveforms;
a data processor configured to:
receive the received electrical waveforms;
estimate a difference in the received waveforms that results at least partially from resonance of the sample; and
characterize a mechanical property of the sample from at least one feature of the estimated difference; and
a controller configured to control the timing of the ultrasound transmitter and data processor.

* * * * *